(12) United States Patent
Xu et al.

(10) Patent No.: US 11,475,569 B2
(45) Date of Patent: Oct. 18, 2022

(54) SYSTEMS AND METHODS FOR IMAGE PROCESSING

(71) Applicant: SHANGHAI UNITED IMAGING HEALTHCARE CO., LTD., Shanghai (CN)

(72) Inventors: Liang Xu, Shanghai (CN); Jing Yan, Shanghai (CN); Hanyu Wang, Shanghai (CN); Jie Niu, Shanghai (CN); Haihua Zhou, Shanghai (CN); Juan Feng, Shanghai (CN); Le Yang, Shanghai (CN); Na Zhang, Shanghai (CN); Yange Ma, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

(21) Appl. No.: 17/106,176

(22) Filed: Nov. 29, 2020

(65) Prior Publication Data

US 2021/0118139 A1 Apr. 22, 2021

Related U.S. Application Data

(63) Continuation of application No. PCT/CN2019/089388, filed on May 30, 2019.

(30) Foreign Application Priority Data

| May 30, 2018 | (CN) | 201810538825.7 |
| Aug. 29, 2018 | (CN) | 201810996464.0 |
| Dec. 20, 2018 | (CN) | 201811564078.0 |

(51) Int. Cl.
G06T 7/00 (2017.01)
G06T 7/194 (2017.01)
(Continued)

(52) U.S. Cl.
CPC .............. *G06T 7/0014* (2013.01); *A61B 6/06* (2013.01); *A61B 6/502* (2013.01); *A61B 6/547* (2013.01);
(Continued)

(58) Field of Classification Search
CPC ........... G06T 2207/10116; G06T 5/009; G06T 7/194; G06T 7/0012; G06T 7/13;
(Continued)

(56) References Cited

U.S. PATENT DOCUMENTS 5,633,511 A * 5/1997 Lee ........................ G06T 5/40
250/587
6,421,454 B1 7/2002 Burke et al.
(Continued)

FOREIGN PATENT DOCUMENTS

| CN | 101419712 A | 4/2009 |
| CN | 101609549 A | 12/2009 |

(Continued)

OTHER PUBLICATIONS

Computational Statistics and Data Analysis. Anatomical curve identification 2015 (Year: 2015).*
(Continued)

*Primary Examiner* — Nizar N Sivji
(74) *Attorney, Agent, or Firm* — Metis IP LLC

(57) ABSTRACT

A method may include obtaining a breast image of an object that is acquired by an imaging device; determining a projection curve based on the breast image; determining a first valley point and a second valley point of the projection curve; determining a peak point of the projection curve based the first valley point and the second valley point of the projection curve; determining a first valley location, a second valley location, and a peak location in the breast image based on the peak point, the first valley point, and the second valley point of the projection curve; and
(Continued)

determining a breast region in the breast image based on the first valley location, the second valley location, and the peak location.

19 Claims, 22 Drawing Sheets

(51) Int. Cl.
| | |
|---|---|
| G06T 7/13 | (2017.01) |
| G06T 7/70 | (2017.01) |
| A61B 6/06 | (2006.01) |
| A61B 6/00 | (2006.01) |
| G06T 5/00 | (2006.01) |

(52) U.S. Cl.
CPC ............... *G06T 5/005* (2013.01); *G06T 7/13* (2017.01); *G06T 7/194* (2017.01); *G06T 7/70* (2017.01); *G06T 2207/10116* (2013.01); *G06T 2207/30068* (2013.01)

(58) Field of Classification Search
CPC ............. G06T 2207/30068; G06T 7/11; G06T 7/0014; G06T 5/005; G06T 7/70; G06T 7/136; A61B 6/502; A61B 6/06; A61B 6/547; G06V 10/28; G06V 10/32
See application file for complete search history.

(56) References Cited

U.S. PATENT DOCUMENTS

| | | | | |
|---|---|---|---|---|
| 7,315,640 | B1* | 1/2008 | Brady | ............... G06T 5/003 382/128 |
| 8,144,153 | B1 | 3/2012 | Sullivan et al. | |
| 8,971,637 | B1* | 3/2015 | Rivard | ............... G06T 7/13 382/199 |
| 2002/0085679 | A1 | 7/2002 | Zastrow et al. | |
| 2004/0094167 | A1* | 5/2004 | Brady | ............... G06T 7/55 600/443 |
| 2006/0018431 | A1 | 1/2006 | Kanemitsu | |
| 2006/0140483 | A1 | 6/2006 | Jabri et al. | |
| 2007/0189448 | A1 | 8/2007 | Muller et al. | |
| 2008/0069416 | A1 | 3/2008 | Luo | |
| 2008/0218635 | A1 | 9/2008 | Tsuruoka | |
| 2009/0238433 | A1 | 9/2009 | Rao et al. | |
| 2011/0280465 | A1* | 11/2011 | Wehnes | ............... G06T 7/143 382/132 |
| 2014/0088415 | A1* | 3/2014 | Hielscher | ............. A61B 5/0073 600/425 |
| 2014/0307937 | A1* | 10/2014 | El-Hilo | ............... G06T 7/0012 382/132 |
| 2015/0010219 | A1 | 1/2015 | Behiels | |
| 2015/0036911 | A1* | 2/2015 | Brenner | ............... A61B 6/037 382/132 |
| 2015/0348238 | A1 | 12/2015 | Sasaki et al. | |
| 2016/0302742 | A1* | 10/2016 | Maidment | ............. A61B 6/5235 |
| 2017/0032535 | A1* | 2/2017 | Harding | ............... G06T 3/0093 |
| 2017/0270693 | A1* | 9/2017 | Yang | ............... G06T 11/003 |

FOREIGN PATENT DOCUMENTS

| | | | |
|---|---|---|---|
| CN | 103345732 | A | 10/2013 |
| CN | 103445795 | A | 12/2013 |
| CN | 104161531 | A | 11/2014 |
| CN | 104574327 | A | 4/2015 |
| CN | 104616249 | A | 5/2015 |
| CN | 104616252 | A | 5/2015 |
| CN | 105374025 | A | 3/2016 |
| CN | 105574820 | A | 5/2016 |
| CN | 106327511 | A | 1/2017 |
| CN | 106991648 | A | 7/2017 |
| CN | 107103605 | A | 8/2017 |
| CN | 107564021 | A | 1/2018 |
| CN | 107569248 | A | 1/2018 |
| CN | 107622501 | A | 1/2018 |
| CN | 107862691 | A | 3/2018 |
| CN | 107871319 | A | 4/2018 |
| CN | 108198147 | A | 6/2018 |
| CN | 108765421 | A | 11/2018 |
| CN | 108830813 | A | 11/2018 |
| CN | 108830816 | A | 11/2018 |
| CN | 108876741 | A | 11/2018 |
| CN | 109242840 | A | 1/2019 |
| CN | 109658354 | A | 4/2019 |
| EP | 0742536 | A1 | 11/1996 |
| EP | 2287632 | A1 | 2/2011 |

OTHER PUBLICATIONS

Automatic detection of small lung nodules on CT utilizing a local density maximum algorithm—2003 (Year: 2003).*
Enhancing Transparent Skin Surfaces with Ridge and Valley Lines—1995 (Year: 1995).*
FASU: A Full Automatic Segmenting System for Ultrasound Images—2002 (Year: 2002).*
Multiresolution Analysis of Ridges and Valleys in Grey-Scale Images—1993 (Year: 1993).*
Statistical models for manifold data with applications to the human face—2017 (Year: 2017).*
The Third Office Action in Chinese Application No. 201811564078.0 dated Jun. 10, 2021, 19 pages.
The Extended European Search Report in European Application No. 19810381.4 dated Jun. 4, 2021, 11 pages.
Ma, Hongqiang et al., Low-Light Image Enhancement Based on Deep Convolutional Neural Network, Acta Optica Sinica, 39(2): 1-10, 2018.
Xu, Cong et al., Processing Algorithm Theory Based on Wavelet Transform, Computer and Digital Engineering, 45(8): 1643-1646, 2017.
Chen, Xiaolong et al., Digital Medical Image Enhancement Based on Pyramid, Nuclear Electronics & Detection Technology, 2016, 5 pages.
Tang, Quan et al., Breast X-ray Image Enhancement Based on Dyadic Wavelet and PDE, Electronic Design Engineering, 26(5): 22-26, 2018.
Lv, Lizhi et al., Medical CT Image Enhancement Algorithm Based on Laplacian Pyramid and Wavelet Transform, Computer Science, 43(11): 300-303, 2016.
He, Zhiliang et al., Image Enhancement Method Based on Image Pyramid, Image & Multimedia Technology, 2014, 2 pages.
Cheng, Hong, Design and Research of Beam Limiter Subsystem of Medical X-ray Machine, China Excellent Doctoral Dissertation Full-text Database (Master) Engineering Science and Technology Series II, 2006, 61 pages.
Zheng, Weitao et al., Image Contrast Enhancement by Contourlet Transform and PCNN, IEEE, 2012, 5 pages.
Cai, Yong et al., Automatic Segmentation of Ultrasound Medical Images, Journal of Lanzhou Jiaotong University, 23(4): 61-64, 2004.
International Search Report in PCT/CN2019/089388 dated Aug. 27, 2019, 6 pages.
Written Opinion in PCT/CN2019/089388 dated Aug. 27, 2019, 6 pages.
First Office Action in Chinese Application No. 201810538825.7 dated Apr. 28, 2020, 13 pages.

\* cited by examiner

1200

| Obtaining a preset distance between the first coordinates of the first valley point and the second valley point, and preset positions of the first valley point and the second valley point in the projection curve, the preset distance and the preset positions being set based on breast characteristics | 1210 |

↓

| Determining whether there is any valley point or point whose second coordinate is 0 | 1220 |

↓

| Determining the first valley point and the second valley point in the projection curve based on the determination result, the preset distance, and the preset positions | 1230 |

FIG. 12A

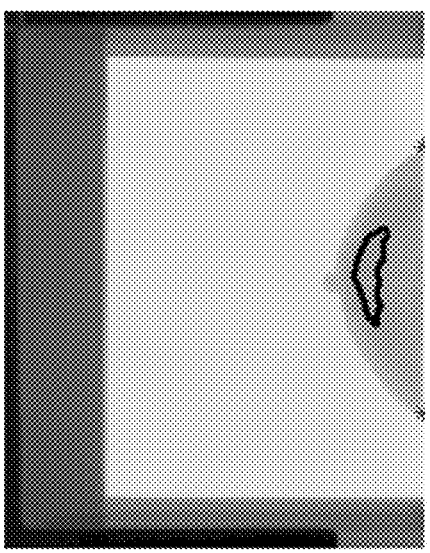

FIG. 12B

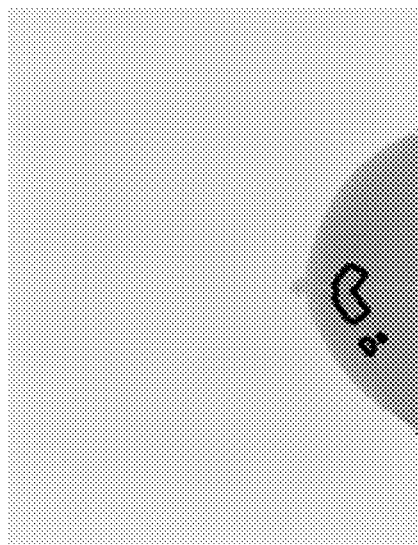

```
┌─────────────────────────────────────────────────────────────┐
│ Determining a first straight line from the peak location,   │ ⟋1810
│ the first straight line being perpendicular to a second     │
│ straight line connecting the first valley location and the  │
│ second valley location                                      │
└─────────────────────────────────────────────────────────────┘
                              ↓
┌─────────────────────────────────────────────────────────────┐
│ Determining an intersection of the first straight line and  │ ⟋1820
│ an edge of the breast image close to a chest wall of the    │
│ object                                                      │
└─────────────────────────────────────────────────────────────┘
                              ↓
┌─────────────────────────────────────────────────────────────┐
│ Determining the breast region in the breast image by        │ ⟋1830
│ connecting the first valley location, the second valley     │
│ location, and the intersection                              │
└─────────────────────────────────────────────────────────────┘
```

FIG. 18

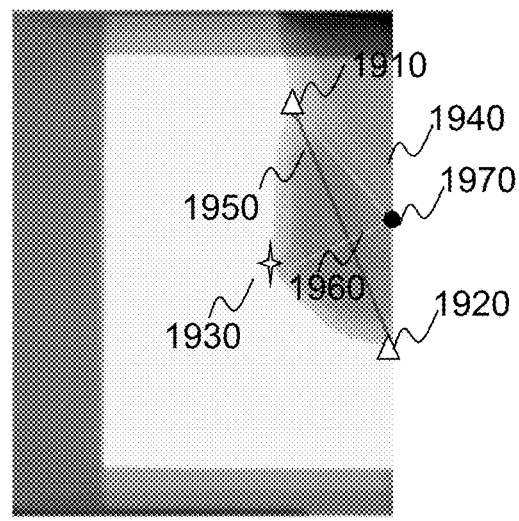

Obtaining a plurality of first decomposition coefficients of a sample image and a plurality of second decomposition coefficients of an enhanced image corresponding to the sample image by decomposing the sample image and the corresponding enhanced image — 2610

Determining the plurality of first decomposition coefficients and the plurality of second decomposition coefficients as a sample pair — 2620

Obtaining a sample image — 2710

Obtaining a plurality of decomposition coefficients of the sample image by decomposing the sample image — 2720

Obtaining a plurality of enhanced coefficients by perform enhancement to the decomposition coefficients of the sample image — 2730

Determining the plurality of decomposition coefficients of the sample image and the plurality of corresponding enhanced coefficients as a sample pair — 2740

FIG. 27

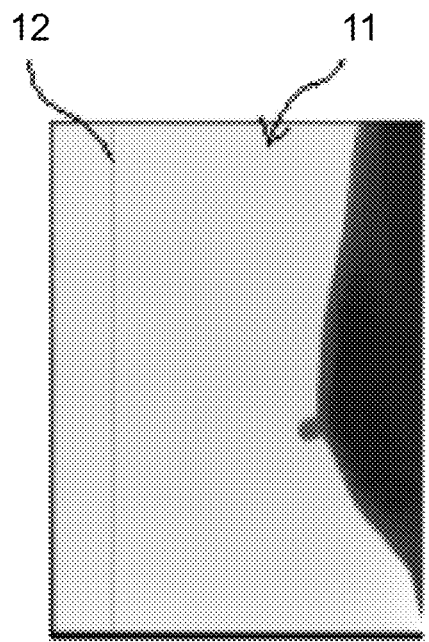 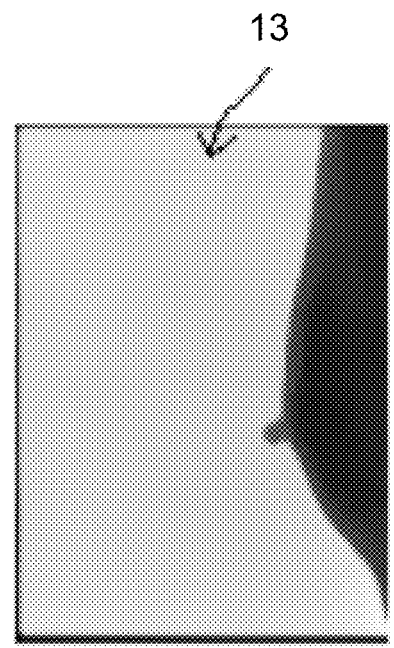
FIG. 31B  FIG. 31C
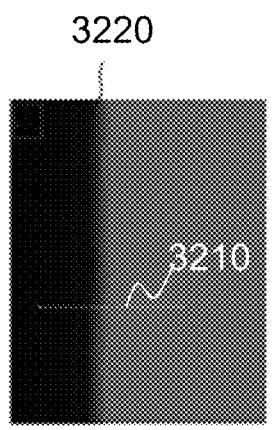 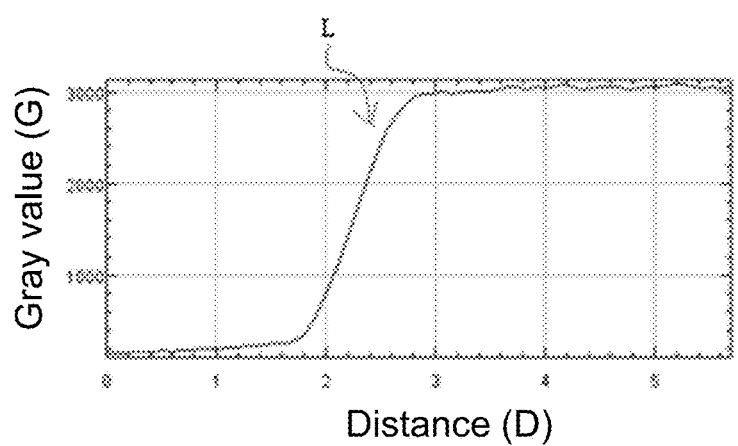
FIG. 32A  FIG. 32B

SYSTEMS AND METHODS FOR IMAGE PROCESSING

CROSS-REFERENCE TO RELATED APPLICATIONS

This application is a Continuation of International Application No. PCT/CN2019/089388 filed on May 30, 2019, which claims priority to Chinese Patent Application No. 201810538825.7 filed on May 30, 2018, Chinese Patent Application No. 201810996464.0 filed on Aug. 29, 2018, and Chinese Patent Application No. 201811564078.0 filed on Dec. 20, 2018, the contents of each of which are hereby incorporated by reference.

TECHNICAL FIELD

The present disclosure generally relates to image processing, and in particular, to systems and methods for image segmentation and/or image enhancement.

BACKGROUND

Medical imaging becomes more and more important in modern medicine. In certain cases, imaging processing, such as imaging segmentation and/or image enhancement, is performed on medical images to help doctors to make a diagnosis. Therefore, it is desirable to provide systems and method to realize more accurate and more efficient image segmentation and/or image enhancement.

SUMMARY

According to a first aspect of the present disclosure, a system may include one or more storage devices and one or more processors configured to communicate with the one or more storage devices. The one or more storage devices may include a set of instructions. When the one or more processors execute the set of instructions, the one or more processors may be directed to perform one or more of the following operations. The one or more processors may obtain a breast image of an object that is acquired by an imaging device; determine a projection curve based on the breast image; determine a first valley point and a second valley point of the projection curve; determine a peak point of the projection curve based the first valley point and the second valley point of the projection curve; determine a first valley location, a second valley location, and a peak location in the breast image based on the peak point, the first valley point, and the second valley point of the projection curve; and determine a breast region in the breast image based on the first valley location, the second valley location, and the peak location.

In some embodiments, the determining the projection curve based on the breast image includes: dividing the breast image into a body region and a background region, the body region including a breast; generating a binary image by designating pixel values of pixels in the body region as 1 and designating pixel values of pixels in the background region as 0; determining a chest-wall side of the binary image; and obtaining the projection curve by determining a plurality of sums each of which is a sum of pixel values of a row of pixels in the binary image, the row of pixels being arranged along a direction between the chest-wall side and a side of the binary image opposite to the chest-wall side.

In some embodiments, for each point on the projection curve, a first coordinate on a first coordinate axis of the point represents a position of a row of pixels in the binary image, and a second coordinate on a second coordinate axis of the point represents a sum of pixies values of the corresponding row of pixels.

In some embodiments, 4 the determining the first valley point and the second valley point of the projection curve includes: obtaining a preset distance between the first coordinates of the first valley point and the second valley point, and preset positions of the first valley point and the second valley point in the projection curve, the preset distance and the preset positions being set based on breast characteristics; determining whether there is any valley point or point whose second coordinate is 0 in the projection curve; and determining the first valley point and the second valley point in the projection curve based on the determination result, the preset distance, and the preset positions.

In some embodiments, the determining the first valley location, the second valley location, and the peak location in the breast image based on the peak point, the first valley point, and the second valley point of the projection curve includes: determining that the second coordinate of the first valley point or the second valley point is greater than the second coordinate of the peak point; in response to a determination that the second coordinate of the first valley point or the second valley point is greater than the second coordinate of the peak point, rotating the binary image so that a straight line connecting points in the rotated binary image corresponding to the first valley point and the second valley point is parallel to or coincides with the second coordinate axis; determining a new projection curve based on the rotated binary image; and updating the first valley point, the second valley point, and the peak point based on the new projection curve; and determining the first valley location, the second valley location, and the peak location in the breast image based on the updated first valley point, the updated second valley point, and the updated peak point.

In some embodiments, the determining the first valley location, the second valley location, and the peak location in the breast image based on the peak point, the first valley point, and the second valley point of the projection curve includes: determining that there is no valley point in the projection curve and there is at least one point whose second coordinate is 0 on only one side of the peak point of the projection curve; in response to a determination that there is no valley point in the projection curve and there is at least one point whose second coordinate is 0 on only one side of the peak point of the projection curve, rotating the binary image so that a straight line connecting points in the rotated binary image corresponding to the first valley point and the second valley point is parallel to or coincides with the second coordinate axis; determining a new projection curve based on the rotated binary image; updating the first valley point, the second valley point, and the peak point based on the new projection curve; and determining the first valley location, the second valley location, and the peak location in the breast image based on the updated first valley point, the updated second valley point, and the updated peak point.

In some embodiments, the determining the breast region in the breast image based on the first valley location, the second valley location, and the peak location includes: determining a first straight line from the peak location, the first straight line being perpendicular to a second straight line connecting the first valley location and the second valley location; determining an intersection of the first straight line and a chest-wall side of the breast image; and determining the breast region in the breast image by connecting the first valley location, the second valley location, and intersection.

According to another aspect of the present disclosure, a method may include one or more of the following operations. One or more processors may obtain a breast image of an object that is acquired by an imaging device; determine a projection curve based on the breast image; determining a first valley point and a second valley point of the projection curve; determine a peak point of the projection curve based the first valley point and the second valley point of the projection curve; determine a first valley location, a second valley location, and a peak location in the breast image based on the peak point, the first valley point, and the second valley point of the projection curve; and determine a breast region in the breast image based on the first valley location, the second valley location, and the peak location.

According to yet another aspect of the present disclosure, a system may include one or more storage devices and one or more processors configured to communicate with the one or more storage devices. The one or more storage devices may include a set of instructions. When the one or more processors execute the set of instructions, the one or more processors may be directed to perform one or more of the following operations. The one or more processors may obtain a pre-exposure breast image of a breast of an object that is acquired by an imaging device; determine a breast region in the pre-exposure breast image by processing the pre-exposure breast image based on the method provided in the present disclosure; determine a gland region in the determined breast region; determine a gray level of the gland region; obtain a preset relationship of a pre-exposure X-ray dose used to acquire the pre-exposure breast image, a compression thickness of the breast, the gray level of the gland region, and AEC parameters; and determine the AEC parameters based on the preset relationship, the X-ray dose, the compression thickness of the breast, and the gray level of the gland region.

According to yet another aspect of the present disclosure, a system may include one or more storage devices and one or more processors configured to communicate with the one or more storage devices. The one or more storage devices may include a set of instructions. When the one or more processors execute the set of instructions, the one or more processors may be directed to perform one or more of the following operations. The one or more processors may obtain a breast image of an object that is acquired by an imaging device; obtain a binary template including a direct exposure region of the breast image; obtain a binary gradient image by performing gradient transform and binarization to the breast image, the binary gradient image including one or more straight line features; determine a preliminary region based on the binary template and the binary gradient image; process at least one of the breast image, the binary template, and the binary gradient image to reduce an effect of overexposure or tissue of the object with high X-ray attenuation in the breast image on the one or more straight line features; identify the one or more straight line features in the binary gradient image based on the processing result; and determine an edge of a collimator of the imaging device in the preliminary region based on the identified one or more straight line features, the edge including at least one of the identified one or more straight line features each of which has a length longer than a length threshold and is out of the direct exposure region.

In some embodiments, the identifying the one or more straight line features in the binary gradient image includes: identify the one or more straight line features in the binary gradient image by determining one or more row projection values and one or more column projection values, each of the one or more row projection values being a sum of pixel values of a row of pixels in the binary gradient image, each of the one or more column projection values being a sum of pixel values of a column of pixels in the binary gradient image.

In some embodiments, the breast image includes a chest-wall side, a side opposite to the chest-wall side, an upper side, and a lower side; the determined edge of the collimator in the breast image includes the identified straight line features including a row of pixels associated with the upper side, a row of pixels associated with the lower side, and a column of pixels associated with the side opposite to the chest-wall side, the row projection value of the row of pixels associated with the upper side is a first projection value, the row projection value of the row of pixels associated with the lower side is a second projection value, and the column projection value of the column of pixels associated with the side opposite to the chest-wall side is a third projection value; and the length threshold includes a first length threshold, a second length threshold, and a third length threshold, the first projection value is greater than the first length threshold, the second projection value is greater than the second length threshold, and the third projection value is greater than the third length threshold.

In some embodiments, the binary gradient image includes a first sub-image, a second sub-image, a third sub-image, and a fourth sub-image; and the obtaining the binary gradient image by performing gradient transform and binarization to the breast image includes: processing the breast image by performing gradient transform and binarization to the breast image; obtaining the first sub-image based on a first gradient threshold and the processing result, the first sub-image representing a contour feature of the breast image; and obtaining the second sub-image associated with the upper side, the third sub-image associated with the lower side, and the third sub-image associated with the side opposite to the chest-wall side based on a second gradient threshold and the processing result, the first gradient threshold being greater than the second gradient threshold.

In some embodiments, the one or more processors may obtain a physical position of the collimator in the imaging device; project at least a part of the collimator on the breast image based on the physical position of the collimator; and determine the edge of the collimator in the breast image based on the projection.

In some embodiments, the obtaining the breast image of the object includes: obtain an original breast image of the object that is acquired by the imaging device; obtain a physical position of the collimator in the imaging device; project the collimator on the original breast image based on the physical position of the collimator; and obtain the breast image by cropping the original breast image along the projection of the collimator.

In some embodiments, the processing at least one of the breast image, the binary template, and the binary gradient image to reduce the effect of the overexposure or the tissue of the object with high X-ray attenuation in the breast image on the one or more straight line features includes: add a make-up part to at least one of the one or more straight line features in the preliminary region, the make-up part being in a region corresponding to tissue of the object with high X-ray attenuation.

In some embodiments, the adding the make-up part to the at least one of the one or more straight line features in the preliminary region includes: obtain a first low-gray template based on the breast image and a first gray threshold, the first low-gray template including a first region representing the tissue of the object with high X-ray attenuation; determine a second region by performing dilation to the first region using a dilation kernel to generate a second low-gray template, the second region being larger than the first region; obtain a third low-gray template by removing a region other than the preliminary region from the second low-gray template, the third low-gray template including a third region corresponding to the second region, the third region being smaller than the second region; and add the make-up part to the at least one of the one or more straight line features in the preliminary region by extending the at least one of the one or more straight line features to the third region.

In some embodiments, the processing at least one of the breast image, the binary template, and the binary gradient image to reduce the effect of the overexposure or the tissue of the object with high X-ray attenuation in the breast image on the one or more straight line features includes: perform erosion to the direct exposure region in the binary template using a first erosion kernel or a second erosion kernel, a size of the second erosion kernel being larger than that of the first erosion kernel.

In some embodiments, the performing the erosion to the direct exposure region in the binary template using the first erosion kernel or the second erosion kernel includes: obtain a high-gray template based on the breast image and a second gray threshold, the high-gray template including a first gray region in which gray values of pixels are greater than or equal to the second gray threshold; determine whether a ratio of a size of the first gray region in the high-gray template to a size of the direct exposure region in the binary template is greater than a ratio threshold; perform the erosion to the direct exposure region in the binary template based on a determination result.

In some embodiments, the determination result includes that the ratio of the size of the first gray region to the size of the direct exposure region is greater than the ratio threshold, and the performing the erosion to the direct exposure region in the binary template based on a determination result includes performing the erosion to the direct exposure region in the binary template using the second erosion kernel.

In some embodiments, the determination result includes that the ratio of the size of the first gray region to the size of the direct exposure region is less than the ratio threshold, and the performing the erosion to the direct exposure region in the binary template based on a determination result includes performing the erosion to the direct exposure region in the binary template using the first erosion kernel or performing no erosion to the direct exposure region.

According to yet another aspect of the present disclosure, a method may include one or more of the following operations. One or more processors may obtain a breast image of an object that is acquired by an imaging device; obtain a binary template including a direct exposure region of the breast image; obtain a binary gradient image by performing gradient transform and binarization to the breast image, the binary gradient image including one or more straight line features; determine a preliminary region based on the binary template and the binary gradient image; process at least one of the breast image, the binary template, and the binary gradient image to reduce an effect of overexposure or tissue of the object with high X-ray attenuation in the breast image on the one or more straight line features; identify the one or more straight line features in the binary gradient image based on the processing result; and determine an edge of a collimator of the imaging device in the preliminary region based on the identified one or more straight line features, the edge including at least one of the identified one or more straight line features each of which has a length longer than a length threshold and is out of the direct exposure region.

According to yet another aspect of the present disclosure, a method may include one or more of the following operations. One or more processors may obtain an original image; obtain a plurality of decomposition coefficients of the original image by decomposing the original image; obtain at least one enhancement coefficient by performing enhancement to at least one of the plurality of decomposition coefficients using a machine learning model; and obtain an enhanced image corresponding to the original image based on the decomposition coefficients and the at least one enhancement coefficient.

According to yet another aspect of the present disclosure, a system may include one or more storage devices and one or more processors configured to communicate with the one or more storage devices. The one or more storage devices may include a set of instructions. When the one or more processors execute the set of instructions, the one or more processors may be directed to perform one or more of the following operations. The one or more processors may obtain an original image; obtain a plurality of decomposition coefficients of the original image by decomposing the original image; obtain at least one enhancement coefficient by performing enhancement to at least one of the plurality of decomposition coefficients using a machine learning model; and obtain an enhanced image corresponding to the original image based on the decomposition coefficients and the at least one enhancement coefficient.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 12A is a flowchart illustrating an exemplary process for determining a first valley point and a second valley point of a projection curve according to some embodiments of the present disclosure;

FIGS. 12B-12C are schematic diagrams illustrating exemplary breast images showing a lateral view of a breast according to some embodiments of the present disclosure;

FIG. 18 is a flowchart illustrating an exemplary process for determining a breast region according to some embodiments of the present disclosure;

FIG. 19 is a schematic diagram illustrating an exemplary breast region in a breast image according to some embodiments of the present disclosure;

FIG. 26 is a flowchart illustrating an exemplary process for obtaining a training set according to some embodiments of the present disclosure;

FIG. 27 is a flowchart illustrating an exemplary process for obtaining a training set according to some embodiments of the present disclosure;

FIG. 31B is a schematic block diagram illustrating an exemplary breast image with a bad line according to some embodiments of the present disclosure;

FIG. 31C is a schematic block diagram illustrating an exemplary pre-processed breast image without a bad line according to some embodiments of the present disclosure;

FIG. 32A is a schematic diagram showing an exemplary edge of a collimator according to some embodiments of the present disclosure;

FIG. 32B is a schematic diagram of an exemplary gray value feature curve related to the edge of the collimator in FIG. 32A according to some embodiments of the present disclosure;

FIG. 37F is a schematic diagram of an exemplary make-up part of a straight line feature according to some embodiments of the present disclosure; and.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different level in ascending order. However, the terms may be displaced by another expression if they achieve the same purpose.

Figure 2:
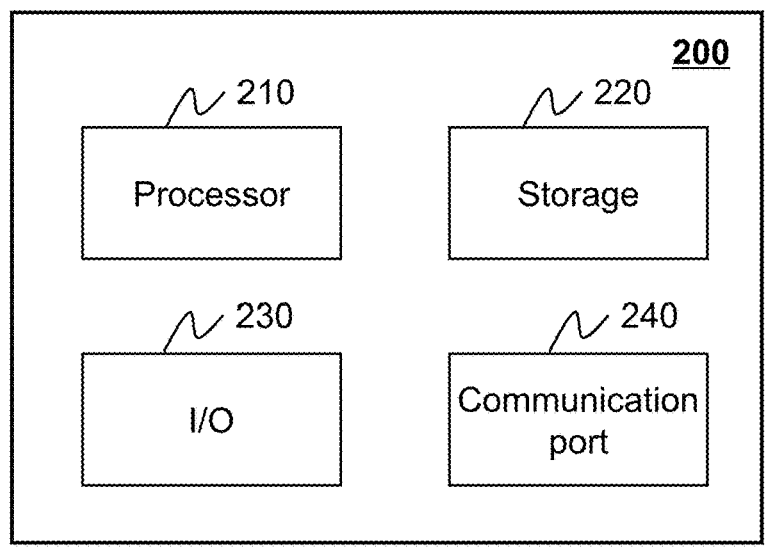
FIG. 2 is a schematic diagram illustrating exemplary hardware and/or software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included of connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for medical imaging and/or medical treatment. In some embodiments, the medical system may include an imaging system. The imaging system may include a single modality imaging system and/or a multi-modality imaging system. The single modality imaging system may include, for example, an X-ray imaging system (e.g., a computed tomography (CT) imaging system, a digital subtraction angiography (DSA) imaging system, a digital radiology (DR) imaging system, a computed radiology (CR) imaging system, etc.), an ultrasound imaging system (e.g., a color Doppler flow imaging (CDFI) system), a magnetic resonance imaging (MRI) system, or a nuclear medical imaging system (e.g., a positron emission tomography (PET) imaging system, a single photon emission computed tomography (SPECT) imaging system, etc.). The multi-modality imaging system may include, for example, a computed tomography-magnetic resonance imaging (MRI-CT) system, a positron emission tomography-magnetic resonance imaging (PET-MRI) system, a single photon emission computed tomography-magnetic resonance imaging (SPECT-MRI) system, a digital subtraction angiography-magnetic resonance imaging (DSA-MRI) system, a positron emission tomography-magnetic resonance imaging-computed tomography (PET-CT) imaging system, etc. In some embodiments, the medical system may include a treatment system. The treatment system may include a treatment plan system (TPS), image-guide radiotherapy (IGRT), etc. The image-guide radiotherapy (IGRT) may include a treatment device and an imaging device. The treatment device may include a linear accelerator, a cyclotron, a synchrotron, etc., configured to perform a radio therapy on a subject. The treatment device may include an accelerator of species of particles including, for example, photons, electrons, protons, or heavy ions. The imaging device may include an MRI scanner, a CT scanner (e.g., cone beam computed tomography (CBCT) scanner), a digital radiology (DR) scanner, an electronic portal imaging device (EPID), etc.

In some embodiments, the systems provided herein may be used for medical diagnosis, for example, red blood cell and white blood cell differential diagnosis, chromosome analysis, cancer cell recognition diagnosis, bone and joint soft tissue diagnosis, intracerebral hematoma, extracerebral hematoma, brain tumors, intracranial aneurysms, arteriovenous malformations, cerebral ischemia, intraspinal tumors, syringomyelia and hydrocephalus diagnosis, lumbar disc herniation, diagnosis of primary liver cancer, etc. In some embodiments, the systems provided herein may also be used for scenarios other than a medical diagnosis. For example, image enhancement in natural disaster prediction and forecasting in the field of remote sensing, environmental pollution monitoring, meteorological satellite cloud image processing, identification of ground military targets, and image recognition in security systems.

It should be noted that, in the present disclosure, an image, or a portion thereof (e.g., a region in the image) corresponding to an object (e.g., tissue, an organ, a tumor, etc.) may be referred to as an image, or a portion of thereof (e.g., a region) of or including the object, or the object itself. For instance, a region in an image that corresponds to or represents a breast may be described as that the region includes a breast. As another example, an image of or including a breast may be referred to a breast image, or simply breast. For brevity, that a portion of an image corresponding to or representing an object is processed (e.g., extracted, segmented, etc.) may be described as the object is processed. For instance, that a portion of an image corresponding to a breast is segmented from the rest of the image may be described as that the breast is segmented from the image.

Figure 1:
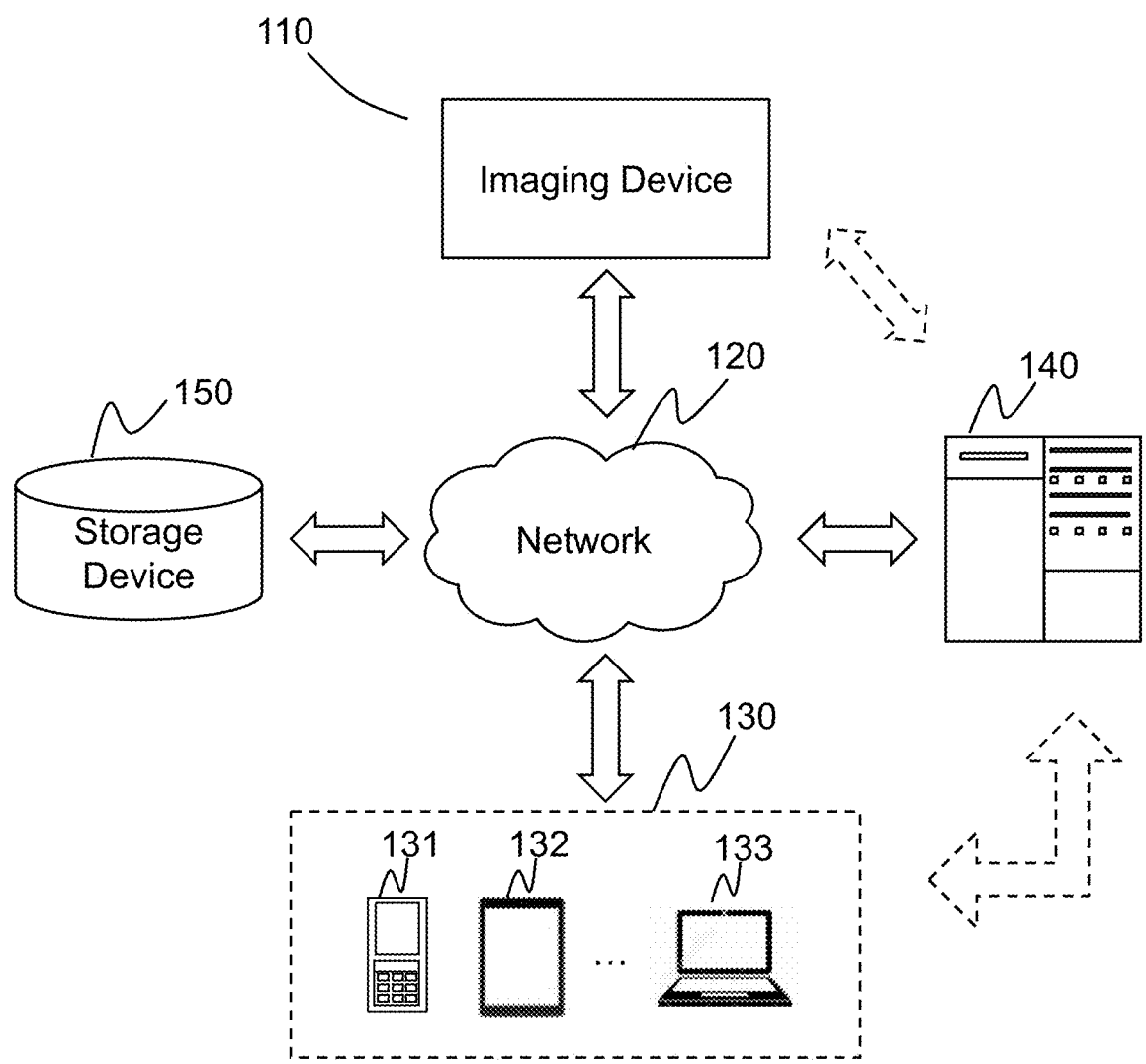
FIG. 1 is a schematic diagram illustrating an exemplary imaging system according to some embodiments of the present disclosure.

FIG. 1 is a schematic diagram illustrating an exemplary imaging system 100 according to some embodiments of the present disclosure. As illustrated, the imaging system 100 may include an imaging device 110, a network 120, a terminal 130, a processing device 140, and a storage device 150. The components of the imaging system 100 may be connected in one or more of various ways. Mere by way of example, as illustrated in FIG. 1, the imaging device 110 may be connected to the processing device 140 through the network 120. As another example, the imaging device 110 may be connected to the processing device 140 directly (as indicated by the bi-directional arrow in dotted lines linking the imaging device 110 and the processing device 140). As a further example, the storage device 150 may be connected to the processing device 140 directly or through the network 120. As still a further example, a terminal device (e.g., 131, 132, 133, etc.) may be connected to the processing device 140 directly (as indicated by the bi-directional arrow in dotted lines linking the terminal 130 and the processing device 140) or through the network 120.

In some embodiments, the imaging device 110 may be an image or video capture/acquiring device. In some embodiments, the imaging device 110 may include a medical imaging device, a camera, a laptop computer, an in-vehicle built-in device, a mobile device, etc., or any combination thereof. In some embodiments, the camera may include a surveillance camera used in a supermarket, a mall, a home, an office area, or the like, or any combination thereof. In some embodiments, the in-vehicle built-in device may include a laptop computer, a head up display (HUD), an on-board diagnostic (OBD) system, a driving recorder, a car navigation, or the like, or any combination thereof. In some embodiments, the mobile device may include a smartphone, a personal digital assistant (PDA), a tablet computer, a handheld game player, a smart glasses, a smart watch, a wearable device, a virtual reality, a display enhancement device, or the like, or any combination thereof.

If the imaging device 110 is the medical imaging device, the imaging device 110 may be used to scan an object located within its detection region and generate a plurality of scan data (e.g., digital signals) used to generate one or more images relating to the object. In the present disclosure, "subject" and "object" are used interchangeably. Mere by way of example, the object may include a patient, a man-made object, etc. As another example, the object may include a specific portion, organ, and/or tissue of a patient. For example, the object may include head, brain, neck, body, shoulder, arm, thorax, cardiac, stomach, blood vessel, soft tissue, knee, feet, or the like, or any combination thereof.

In some embodiments, the imaging device 110 may be used to scan a breast of the object (e.g., a patient). For example, the imaging device 110 may be an X-ray device or an ultrasound device. Taking the X-ray device as an example, the X-ray device may include a breast-holder tray on which the patient lays her breast, an X-ray tube, and a detector. The breast-holder tray may be placed on the top of the detector. The detector may be placed beneath the breast-holder tray. The X-ray tube may emit X-rays going through the breast. The detector may be located opposite to the X-ray tube so as to detect the X-rays that have crossed the patient's breast and the breast-holder tray. The detector may transform the light signals of the detected X-rays into digital signals and transmit the digital signals to the processing device 140 for further processing (e.g., generating a breast image). In some embodiments, the X-ray device may further include a compression pad. For reasons related both to the immobilizing of the breast and to image quality or intensity of X-rays delivered to the patient's breast, it is necessary to compress the patient's breast during the scan process. The compression force may be applied through the compression pad that compresses the breast on the breast-holder tray. In some embodiments, the X-ray device may further include a high-voltage generator configured to provide the voltage that is required for the X-ray tube to produce X-rays. In some embodiments, the X-ray device may further include a collimator configured to adjust an X-ray irradiation range. The collimator also can absorb some scattered X-rays, which may improve the image quality. The collimator may be located in front of the X-ray tube in the emitting direction of the X-rays.

The network 120 may include any suitable network that can facilitate the exchange of information and/or data for the imaging system 100. In some embodiments, one or more components of the imaging system 100 (e.g., the imaging device 110, the terminal 130, the processing device 140, or the storage device 150) may communicate information and/or data with one or more other components of the imaging system 100 via the network 120. For example, the processing device 140 may obtain scan data (e.g., digital signals) of a breast of an object (e.g., a patient) from the imaging device 110 via the network 120. In some embodiments, the network 120 may be any type of wired or wireless network, or a combination thereof. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the imaging system 100 may be connected to the network 120 to exchange data and/or information.

The terminal 130 include a mobile device 131, a tablet computer 132, a laptop computer 133, or the like, or any combination thereof. In some embodiments, the mobile device 131 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a smart bracelet, smart footgear, a pair of smart glasses, a smart helmet, a smart watch, smart clothing, a smart backpack, a smart accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google™ Glass, an Oculus Rift, a Hololens, a Gear VR, etc. In some embodiments, the terminal 130 may remotely operate the imaging device 110 and/or the processing device 140. In some embodiments, the terminal 130 may operate the imaging device 110 and/or the processing device 140 via a wireless connection. In some embodiments, the terminal 130 may receive information and/or instructions inputted by a user, and send the received information and/or instructions to the imaging device 110 or to the processing device 140 via the network 120. In some embodiments, the terminal 130 may receive data and/or information from the processing device 140. In some embodiments, the terminal 130 may be part of the processing device 140. In some embodiments, the terminal 130 may be omitted.

The processing device 140 may process data and/or information obtained from the imaging device 110, the terminal 130, and/or the storage device 150. For example, the processing device 140 may generate one or more medical images (e.g., breast images) by processing scan data (e.g., digital signals) from the imaging device 110. As another example, the processing device 140 may determine a breast region in a breast image. As still another example, the processing device 140 may determine automatic exposure control (AEC) parameters for scanning a breast using the imaging device 110 based on the determined breast region. As still another example, the processing device 140 may determine a collimator region in a breast image. As still another example, the processing device 140 may perform image enhancement to an image. In some embodiments, the processing device 140 may be a single server, or a server group. The server group may be centralized or distributed. In some embodiments, the processing device 140 may be local or remote. For example, the processing device 140 may access information and/or data stored in or acquired by the imaging device 110, the terminal 130, and/or the storage device 150 via the network 120. As another example, the processing device 140 may be directly connected to the imaging device 110 (as illustrated by the bidirectional arrow in dashed lines connecting the processing device 140 and the imaging device 110 in FIG. 1), the terminal 130 (as illustrated by the bidirectional arrow in dashed lines connecting the processing device 140 and the terminal 130 in FIG. 1), and/or the storage device 150 to access stored or acquired information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented on a computing device 200 having one or more components illustrated in FIG. 2 in the present disclosure.

The storage device 150 may store data and/or instructions. In some embodiments, the storage device 150 may store data obtained from the imaging device 110, the terminal 130 and/or the processing device 140. For example, the storage device 150 may store medical images (e.g., breast images) generated by the processing device 140. In some embodiments, the storage device 150 may store data and/or instructions that the processing device 140 may execute or use to perform exemplary methods described in the present disclosure. For example, the storage device 150 may store instructions that the processing device 140 may execute to perform operations including at least one of: generating one or more medical images (e.g., breast images), determining a breast region in a breast image, determining automatic exposure control (AEC) parameters for scanning a breast using the imaging device 110 based on the determined breast region, determining a collimator region in a breast image, and performing image enhancement to an image. In some embodiments, the storage device 150 may include a mass storage device, a removable storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components of the imaging system 100 (e.g., the imaging device 110, the processing device 140, the terminal 130, etc.). One or more components of the imaging system 100 may access the data or instructions stored in the storage device 150 via the network 120. In some embodiments, the storage device 150 may be directly connected to or communicate with one or more components of the imaging system 100 (e.g., the imaging device 110, the processing device 140, the terminal 130, etc.). In some embodiments, the storage device 150 may be part of the processing device 140.

In some embodiments, the imaging system 100 may further include one or more power supplies (not shown in FIG. 1) connected to one or more components of the imaging system 100 (e.g., the imaging device 110, the processing device 140, the terminal 130, the storage device 150, etc.).

Figure 3:
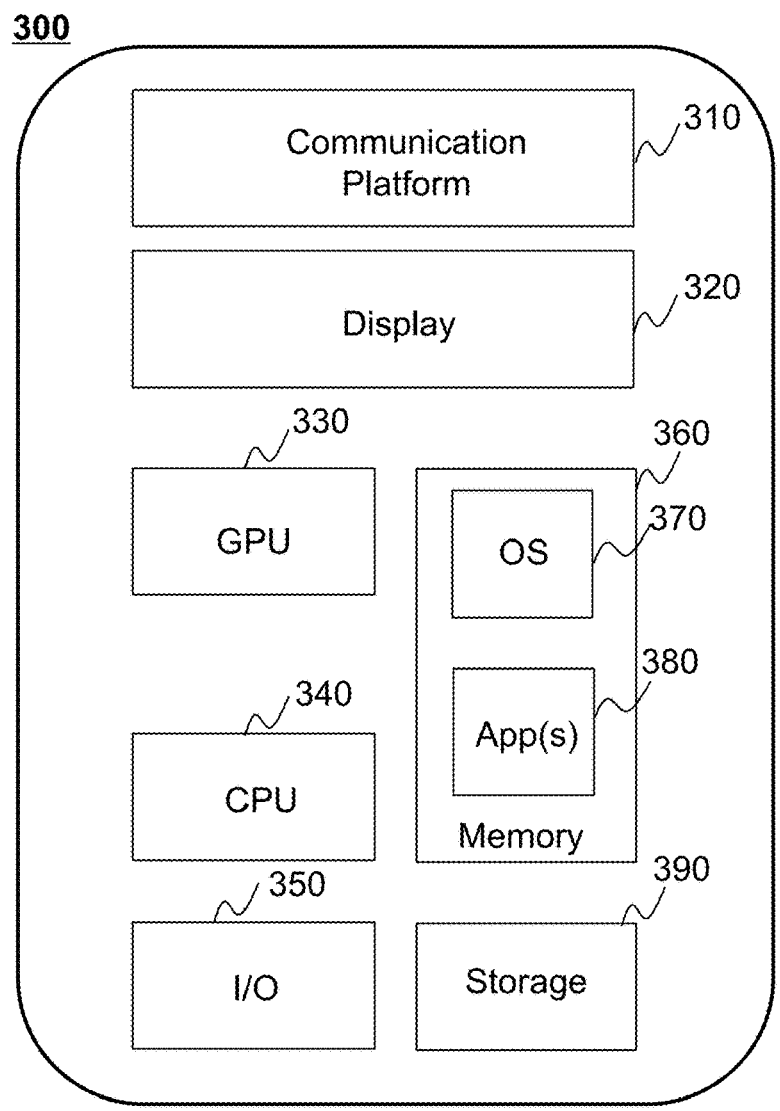
FIG. 3 is a schematic diagram illustrating exemplary hardware and/or software components of a mobile device according to some embodiments of the present disclosure.

FIG. 2 is a schematic diagram illustrating exemplary hardware and/or software components of a computing device on which the processing device 140 may be implemented according to some embodiments of the present disclosure. As illustrated in FIG. 3, the computing device 200 may include a processor 210, a storage 220, an input/output (I/O) 230, and a communication port 240.

The processor 210 may execute computer instructions (program code) and perform functions of the processing device 140 in accordance with techniques described herein. The computer instructions may include routines, programs, objects, components, signals, data structures, procedures, modules, and functions, which perform particular functions described herein. For example, the processor 210 may generate one or more medical images (e.g., breast images) by processing scan data (e.g., digital signals) from the imaging device 110. As another example, the processor 210 may determine a breast region in a breast image. As still another example, the processor 210 may determine automatic exposure control (AEC) parameters for scanning a breast using the imaging device 110 based on the determined breast region. As still another example, the processor 210 may determine a collimator region in a breast image. As still another example, the processor 210 may perform image enhancement to an image. In some embodiments, the processor 210 may include a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration purposes, only one processor is described in the computing device 200. However, it should be noted that the computing device 200 in the present disclosure may also include multiple processors, and thus operations of a method that are performed by one processor as described in the present disclosure may also be jointly or separately performed by the multiple processors. For example, if in the present disclosure the processor of the computing device 200 executes both operations A and B, it should be understood that operations A and step B may also be performed by two different processors jointly or separately in the computing device 200 (e.g., a first processor executes operation A and a second processor executes operation B, or the first and second processors jointly execute operations A and B).

The storage 220 may store data/information obtained from the imaging device 110, the terminal 130, the storage device 150, or any other component of the imaging system 100. In some embodiments, the storage 220 may include a mass storage device, a removable storage device, a volatile read-and-write memory, a read-only memory (ROM), or the like, or any combination thereof. For example, the mass storage device may include a magnetic disk, an optical disk, a solid-state drive, etc. The removable storage device may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store instructions that the processor 210 may execute to perform operations including at least one of: generating one or more medical images (e.g., breast images), determining a breast region in a breast image, determining automatic exposure control (AEC) parameters for scanning a breast using the imaging device 110 based on the determined breast region, determining a collimator region in a breast image, and performing image enhancement to an image.

The I/O 230 may input or output signals, data, or information. In some embodiments, the I/O 230 may enable user interaction with the processing device 140. In some embodiments, the I/O 230 may include an input device and an output device. Exemplary input devices may include a keyboard, a mouse, a touch screen, a microphone, a trackball, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected to a network (e.g., the network 120) to facilitate data communications. The communication port 240 may establish connections between the processing device 140 and the imaging device 110, the terminal 130, or the storage device 150. The connection may be a wired connection, a wireless connection, or a combination of both that enables data transmission and reception. The wired connection may include an electrical cable, an optical cable, a telephone wire, or the like, or any combination thereof. The wireless connection may include Bluetooth, Wi-Fi, WiMax, WLAN, ZigBee, mobile network (e.g., 3G, 4G, 5G, etc.), or the like, or a combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

FIG. 3 is a schematic diagram illustrating exemplary hardware and/or software components of a mobile device on which the terminal 130 may be implemented according to some embodiments of the present disclosure. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the imaging system 100 via the network 120.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to the blood pressure monitoring as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result the drawings should be self-explanatory.

Breast tissue is mainly composed of fat and glands. Because breast tissue is sensitive to X-rays, before the patient's breast is formally scanned, it is usually necessary to use a low dose of X-rays to scan the breast to acquire a pre-exposure breast image. One or more suitable exposure parameters used for a formal scan are obtained based on the analysis result of the pre-exposure image. During the process for analyzing the pre-exposure breast image, if the breast region in the breast image is accurately identified, a more accurate result of identifying the gland region may be obtained, and a more suitable exposure parameter for formal scan may be determined based on the gland region, which ensures that the formal exposure breast image is effective for medical diagnosis and reduces the X-ray dose accepted by the patient in the formal scan.

An aspect of the present disclosure may provide systems and/or method for determining a breast region in a breast image.

Figure 4:
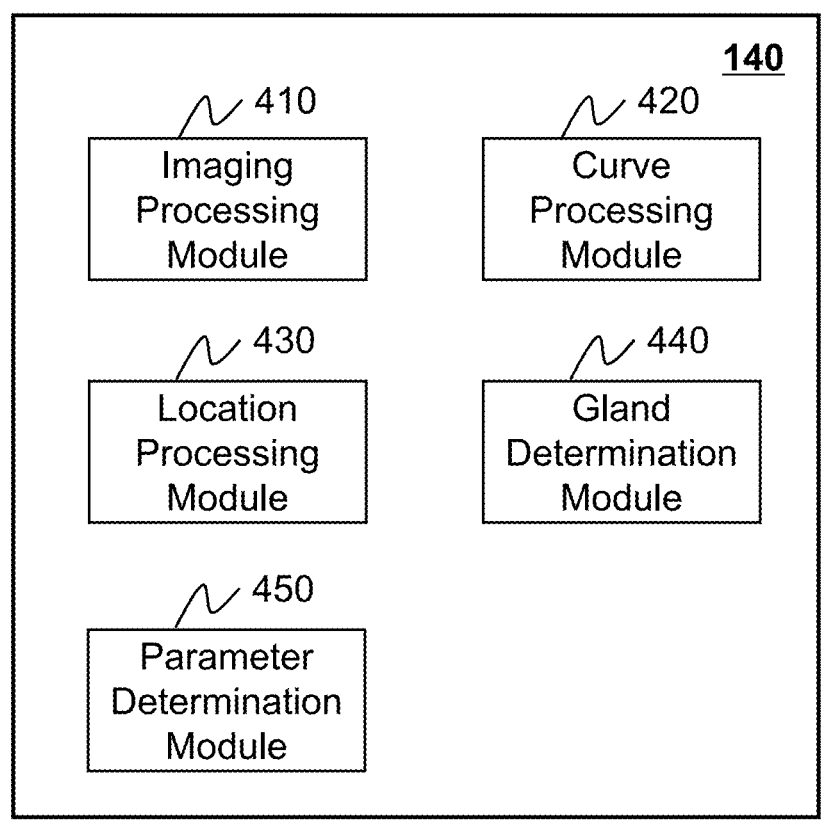
FIG. 4 is a schematic block diagram illustrating an exemplary processing device according to some embodiments of the present disclosure.

FIG. 4 is a schematic block diagram illustrating an exemplary processing device according to some embodiments of the present disclosure. The processing device 140 may include an imaging processing module 410, a curve processing module 420, a location processing module 430, a gland determination module 440, and a parameter determination module 450.

The imaging processing module 410 may be configured to obtain a breast image of an object that is acquired by an imaging device. The curve processing module 420 may be configured to determine a projection curve based on the breast image, determine a first valley point and a second valley point of the projection curve and determine a peak point of the projection curve based the first valley point and the second valley point of the projection curve. The location processing module 430 may be configured to determine a first valley location, a second valley location, and a peak location in the breast image based on the peak point, the first valley point, and the second valley point of the projection curve and determine a breast region in the breast image based on the first valley location, the second valley location, and the peak location. The gland determination module 440 may be configured to determine a gland region in the determined breast region. The parameter determination module 450 may be configured to determine a gray level of the gland region, obtain a preset relationship of a pre-exposure X-ray dose used to acquire the pre-exposure breast image, a compression thickness of the breast, the gray level of the gland region, and AEC parameters, and determine the AEC parameters based on the preset relationship, the X-ray dose, the compression thickness of the breast, and the gray level of the gland region.

The modules in the processing device 140 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. Two or more of the modules may be combined as a single module, and any one of the modules may be divided into two or more units. For example, the imaging processing module 410 may be divided into two units One of the two unit may be configured to obtain a binary image, and the other one of the two unit may be configured to obtain a projection curve based on the binary image.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 140 may further include a storage module (not shown in FIG. 4). The storage module may be configured to store data generated during any process performed by any component of in the processing device 140. As another example, each of the components of the processing device 140 may include a storage device.

Additionally or alternatively, the components of the processing device 140 may share a common storage device.

Figure 5:
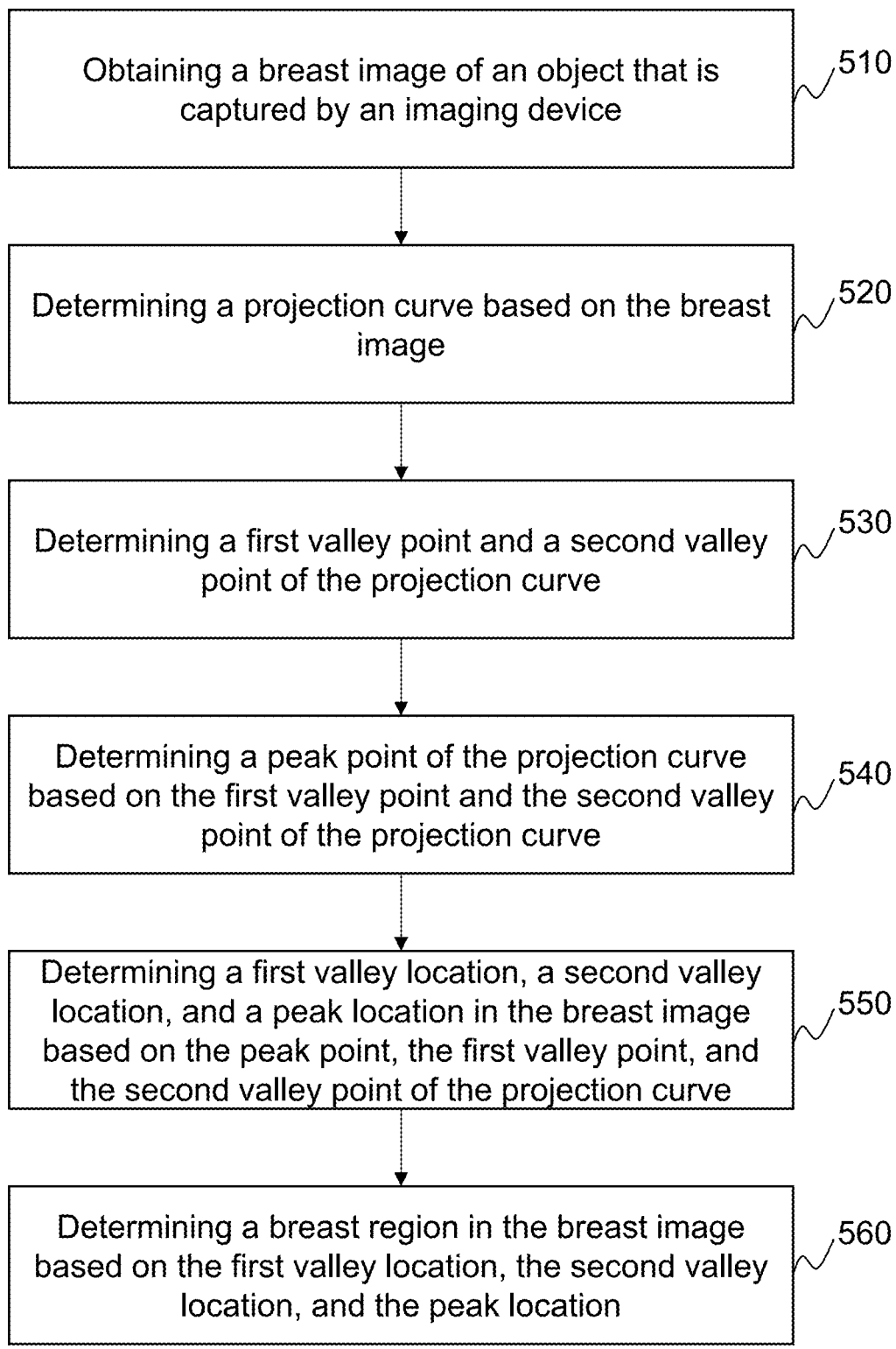
FIG. 5 is a flowchart illustrating an exemplary process for determining a breast region in a breast image according to some embodiments of the present disclosure.

FIG. 5 is a flowchart illustrating an exemplary process for determining a breast region in a breast image according to some embodiments of the present disclosure. In some embodiments, the process 500 may be implemented in the imaging system 100 illustrated in FIG. 1. For example, the process 500 may be stored in a storage medium (e.g., the storage device 150, or the storage 220 of the processing device 140) as a form of instructions, and can be invoked and/or executed by the processing device 140 (e.g., the processor 210 of the processing device 140, or one or more modules in the processing device 140 illustrated in FIG. 4). The operations of the illustrated process 500 presented below are intended to be illustrative. In some embodiments, the process 500 may be accomplished with one or more additional operations not described, and/or without one or more of the operations discussed. Additionally, the order in which the operations of the process 500 as illustrated in FIG. 5 and described below is not intended to be limiting.

Figure 14:
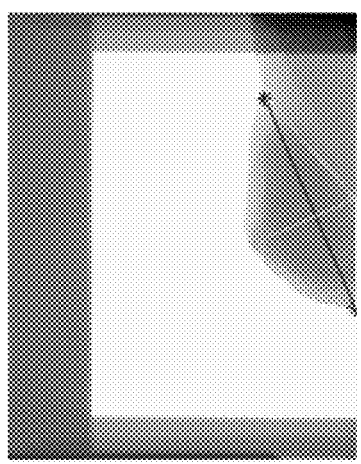
FIG. 14 is a schematic diagram illustrating an exemplary breast image showing a lateral view of a breast according to some embodiments of the present disclosure.

In 510, the processing device 140 (e.g., the image processing module 410) may obtain a breast image of an object that is acquired by an imaging device (e.g., the imaging device 110 of the imaging system 100 in FIG. 1). In some embodiments, the imaging device 110 used here may be an X-ray device. In some embodiments, the breast image may include a breast of the object (e.g., a patient). In some embodiments, the breast image may further include other portion (e.g., the thorax, an arm, etc.) of the object. In some embodiments, the breast image may show the top view (e.g., as shown in FIG. 12B) or the lateral view of the breast (e.g., as shown in FIG. 14).

Figure 7:
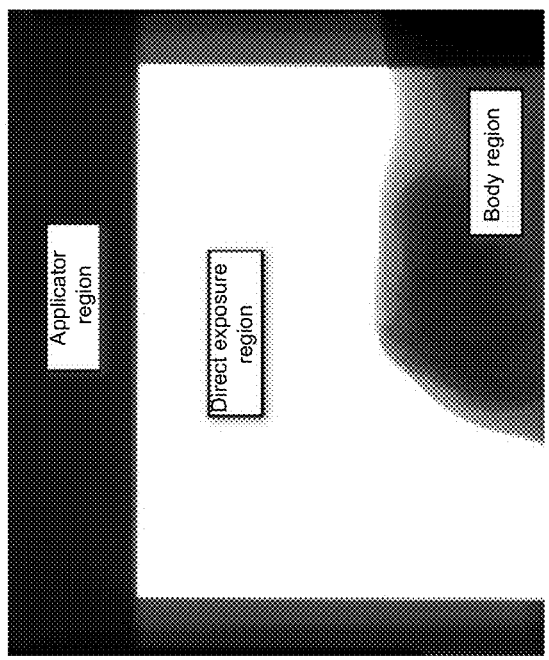
FIG. 7 is a schematic diagram illustrating an exemplary breast image according to some embodiments of the present disclosure.

In 520, the processing device 140 (e.g., the image processing module 410) may determine a projection curve based on the breast image. Merely by way of example, as shown in FIG. 7, the breast image 700 may include a body region including a breast of the object (e.g., a patient), a direct exposure region, and a collimator region. The collimator region in the breast image may correspond to at least a portion of the collimator in the imaging device 110. The direct exposure region may be a region imaged by the X-rays from the X-ray tube to the detector without penetrating any substance that attenuates the X-rays. For example, the direct exposure region may be a region imaged by the X-rays from the X-ray tube to the detector without penetrating any human body such as a portion of a breast. As another example, the direct exposure region may be a region imaged by the X-rays from the X-ray tube to the detector without penetrating any collimator and human body such as a portion of a breast. As still another example, when the X-rays penetrates an area which has nothing except air between the X-ray tube and the detector, the corresponding region imaged by the detector could be referred to as a direction exposure region hereinafter. As still another example, when the X-rays penetrates an area which has nothing except air, the compression pad, and/or the breast-holder tray between the X-ray tube and the detector, the corresponding region imaged by the detector could be referred to as a direction exposure region hereinafter.

Figure 9:
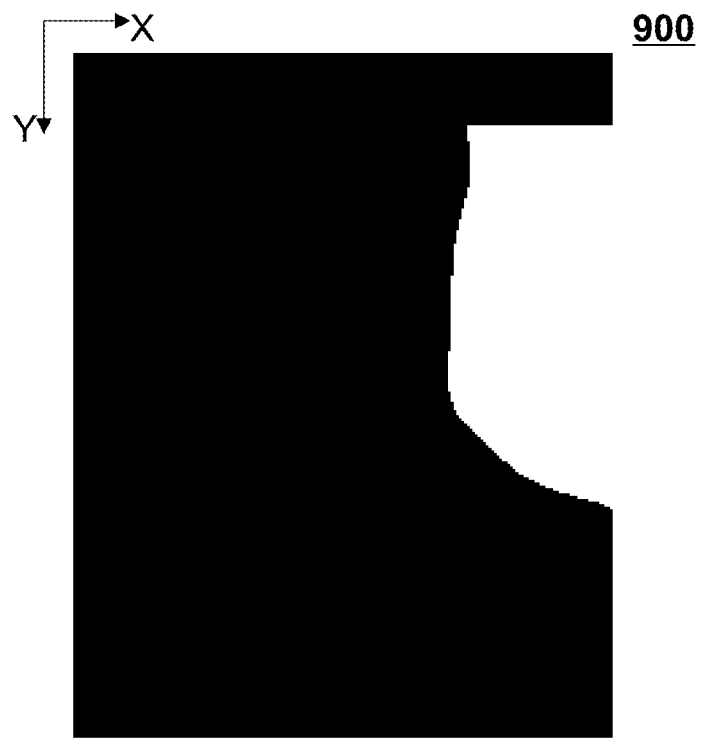
FIG. 9 is a schematic diagram illustrating an exemplary binary image according to some embodiments of the present disclosure.

The processing device 140 may identify the body region and obtain a binary image (e.g., as shown in FIG. 9) including the body region. The processing device 140 may obtain the projection curve by determining a plurality of sums each of which is a sum of pixel values of a row of pixels in the binary image. The row of pixels may be arranged along a direction (e.g., parallel to the X-axis in FIG. 9) perpendicular to the extension direction (e.g., parallel to the Y-axis in FIG. 9) of a chest-wall side of the binary image. The binary image may be a rectangle and have four sides. One of the four sides that is closest to the chest wall in the binary image may be the chest-wall side. As used herein, the chest wall may refer to the boundary of the thorax of the patient. For each point on the projection curve, a first coordinate on a first coordinate axis (e.g., the vertical coordinate axis of the projection curve 1000 in FIG. 10) of the point represents a position of a row of pixels in the binary image, and a second coordinate on a second coordinate axis (e.g., the horizontal coordinate axis of the projection curve 1000 in FIG. 10) of the point represents a sum of pixel values of the corresponding row of pixels. Details regarding the determination of the projection curve may be found elsewhere in the present disclosure (e.g., the description in connection with FIG. 6).

In 530, the processing device 140 (e.g., the curve processing module 420) may determine a first valley point and a second valley point of the projection curve. In some embodiments, the processing device 140 may determine the first alley point and the second valley point based on the shape of the projection curve. Details regarding the determination of the first valley point and the second valley point may be found elsewhere in the present disclosure (e.g., the description in connection with FIG. 12).

In 540, the processing device 140 (e.g., the curve processing module 420) may determine a peak point of the projection curve based on the first valley point and the second valley point of the projection curve. In some embodiments, the peak point may be located between the first valley point and the second valley point. In some embodiments, if there are more than one candidate peak points between the first valley point and the second valley point, the processing device 140 may determine the peak point based on the preset location of the peak point relative to the first valley point and the second valley point.

In 550, the processing device 140 (e.g., the location processing module 430) may determine a first valley location, a second valley location, and a peak location in the breast image based on the peak point, the first valley point, and the second valley point of the projection curve. In some embodiments, the first valley location, the second valley location, and the peak location in the breast image may correspond to the first valley point, the second valley point, and the peak valley point in the curve projection, respectively.

Taking the first valley location as an example, the processing device 140 may determine which pixel row in the binary image the first valley location is in based on the first coordinate of the first valley point. The processing device 140 may identify, in that pixel row, the first pixel of which the pixel value is not 0 along the X-axis direction in FIG. 9. The processing device 140 may determine the pixel in the breast image corresponding to the first pixel in the binary image as the first valley location.

In 560, the processing device 140 (e.g., the location processing module 430) may determine a breast region in the breast image based on the first valley location, the second valley location, and the peak location. In some embodiments, the first valley location and the second valley location may be deemed to represent two points at the junction of the breast and the chest wall of the object. The peak location may be deemed to represent the mammilla of the breast in the breast image. The processing device 140 may determine the breast region by connecting the first valley location, the second valley location, and the peak location. Details regarding the determination of the breast region may be found elsewhere in the present disclosure (e.g., the description in connection with FIG. 18).

In some embodiments, the breast region determined in operation 560 may be used for further processing, for example, processing the determined breast region to obtain a breast gland region, a breast lesion region, or other tissue regions of the breast.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 6:
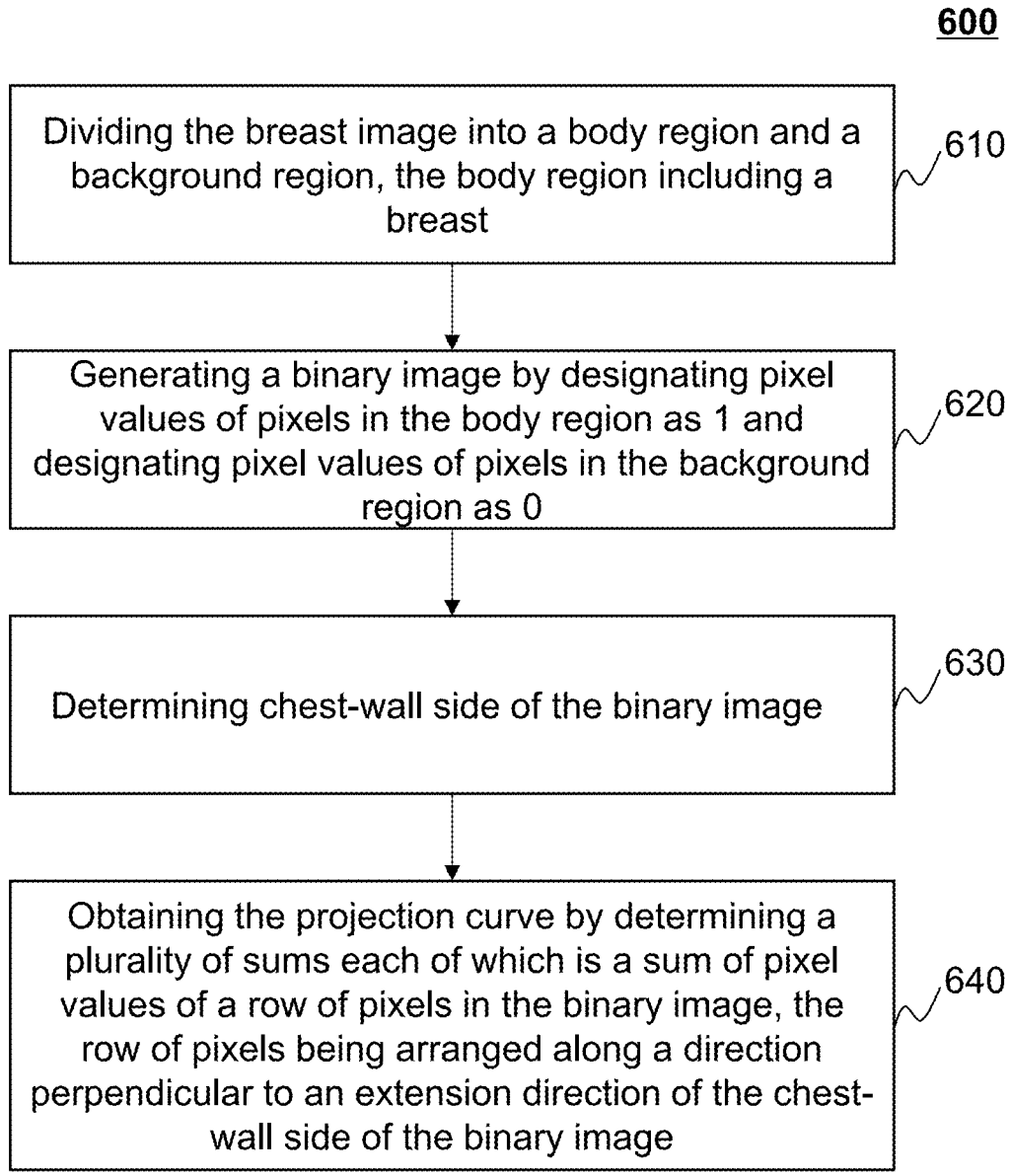
FIG. 6 is a flowchart illustrating an exemplary process for determining a projection curve according to some embodiments of the present disclosure.

FIG. 6 is a flowchart illustrating an exemplary process for determining a projection curve according to some embodiments of the present disclosure. In some embodiments, the process 600 may be implemented in the imaging system 100 illustrated in FIG. 1. For example, the process 600 may be stored in a storage medium (e.g., the storage device 150, or the storage 220 of the processing device 140) as a form of instructions, and can be invoked and/or executed by the processing device 140 (e.g., the processor 210 of the processing device 140, or one or more modules in the processing device 140 illustrated in FIG. 4). The operations of the illustrated process 600 presented below are intended to be illustrative. In some embodiments, the process 600 may be accomplished with one or more additional operations not described, and/or without one or more of the operations discussed. Additionally, the order in which the operations of the process 600 as illustrated in FIG. 6 and described below is not intended to be limiting. In some embodiments, operation 520 of the process 500 in FIG. 5 may be performed based on the process 600.

In 610, the processing device 140 (e.g., the image processing module 410) may divide the breast image into a body region and a background region. The body region may include a breast of the object. The background region may include a direct exposure region and a collimator region (e.g., as shown in FIG. 7) in the breast image.

Figure 8:
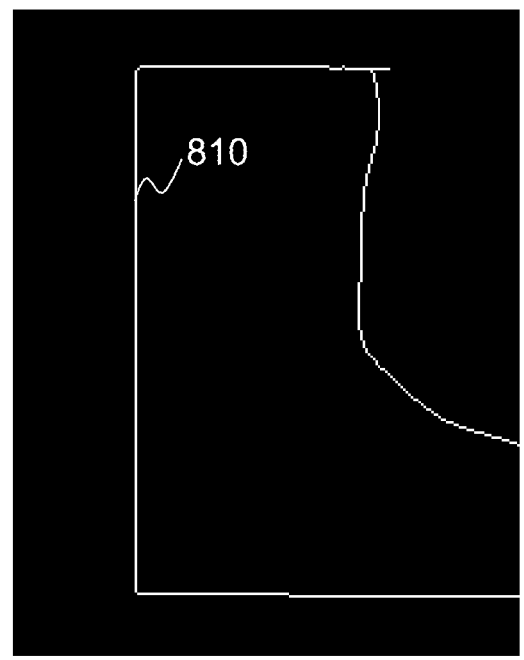
FIG. 8 is a schematic diagram illustrating an exemplary image obtained by performing edge detection according to some embodiments of the present disclosure.

The direct exposure region may be a region imaged by the X-rays from the X-ray tube to the detector without penetrating any substance that attenuates the X-rays. For example, the direct exposure region may be a region imaged by the X-rays from the X-ray tube to the detector without penetrating any human body such as a portion of a breast. As another example, the direct exposure region may be a region imaged by the X-rays from the X-ray tube to the detector without penetrating any collimator and human body such as a portion of a breast. As still another example, when the X-rays penetrates an area which has nothing except air between the X-ray tube and the detector, the corresponding region imaged by the detector could be referred to as a direction exposure region hereinafter. As still another example, when the X-rays penetrates an area which has nothing except air, the compression pad, and/or the breast-holder tray between the X-ray tube and the detector, the corresponding region imaged by the detector could be referred to as a direction exposure region hereinafter. As a result, the direct exposure region may be brighter than the body region and the collimator region in the breast image (e.g., a gray scale image) (e.g., as shown in FIG. 7). The processing device 140 may identify the direct exposure region and an undistinguished region based on pixel values (e.g., gray values) of pixels in the breast image. The undistinguished region may include the body region and the collimator region undistinguished with each other. The processing device 140 may identify the body region and the collimator region by performing edge detection to the undistinguished region (e.g., as shown in FIG. 8). The processing device 140 may combine the collimator region and the direct exposure region as the background region. The above process for determining the body region and the background region may be easier and provide a more accurate segmentation result. Details regarding the identification of the body region and the background region may be found elsewhere in the present disclosure (e.g., the description in connection with FIG. 11).

In 620, the processing device 140 (e.g., the image processing module 410) may generate a binary image by designating pixel values of pixels in the body region as 1 and designating pixel values of pixels in the background region as 0 (e.g., as shown in FIG. 9). In some embodiments, the processing device 140 may generate the binary image by processing the body region and the background region using one-hot encoding. For example, the processing device 140 may generate the binary image shown in FIG. 9 by performing binarization to the image shown in FIG. 8 using one-hot encoding.

In 630, the processing device 140 (e.g., the image processing module 410) may determine a chest-wall side of the binary image. The binary image may be a rectangle and have four sides. One of the four sides that is closest to the chest wall in the binary image may be the chest-wall side. For example, as shown in FIG. 9, the right side of the binary image 900 may be the chest-wall side.

Figure 10:
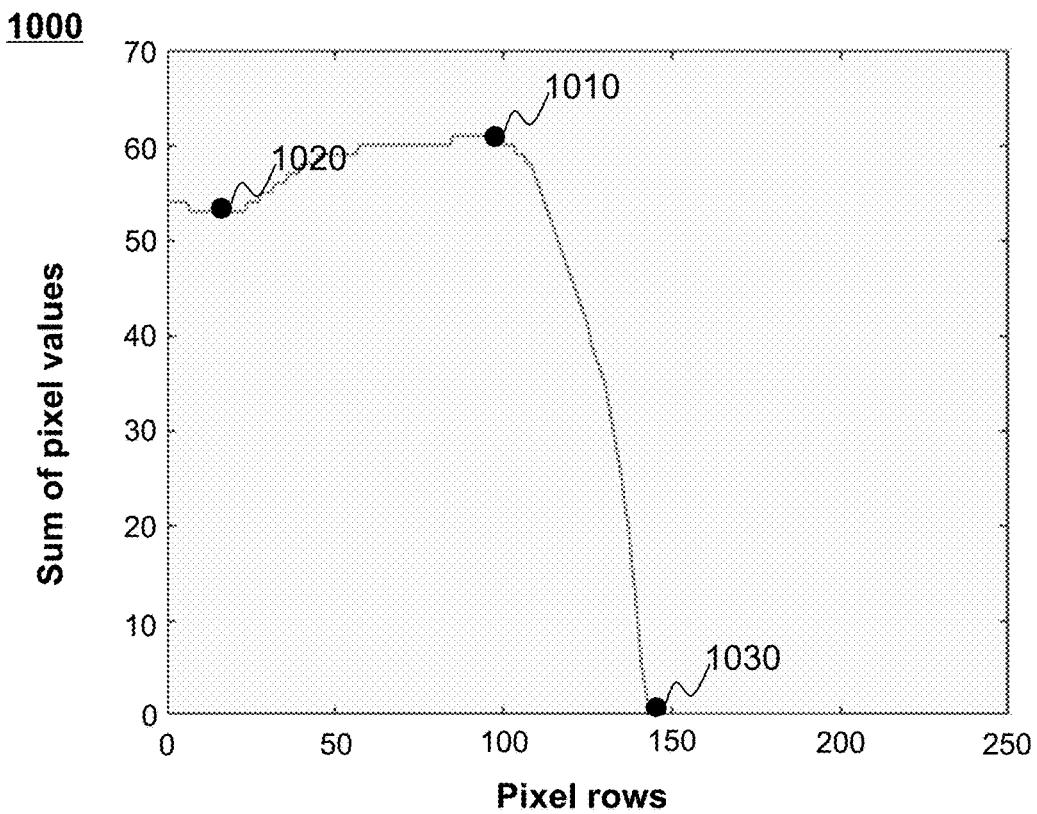
FIG. 10 is a schematic diagram illustrating an exemplary projection curve according to some embodiments of the present disclosure.

In 640, the processing device 140 (e.g., the image processing module 410) may obtain the projection curve (e.g., as shown in FIG. 10) by determining a plurality of sums each of which is a sum of pixel values of a row of pixels in the binary image. The row of pixels may be arranged along a direction (e.g., parallel to the X-axis in FIG. 9) perpendicular to the extension direction (e.g., parallel to the Y-axis in FIG. 9) of the chest-wall side of the binary image.

As shown in FIG. 10, for each point on the projection curve, a first coordinate on a first coordinate axis (e.g., the horizontal coordinate axis of the projection curve 1000 in FIG. 10) of the point may represent a position of a row of pixels in the binary image, and a second coordinate on a second coordinate axis (e.g., the vertical coordinate axis of the projection curve 1000 in FIG. 10) of the point may represent a sum of pixels values of the corresponding row of pixels. For example, the first coordinate of the point 1010 in the projection curve 1000 in FIG. 10 may indicate the $100^{th}$ row of pixels in the binary image 900 along the Y-axis direction in FIG. 9. The second coordinate of the point 1010 in the projection curve 1000 in FIG. 10 may indicate that the sum of pixel values of the $100^{th}$ row of pixels in the binary image is 61.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 11:
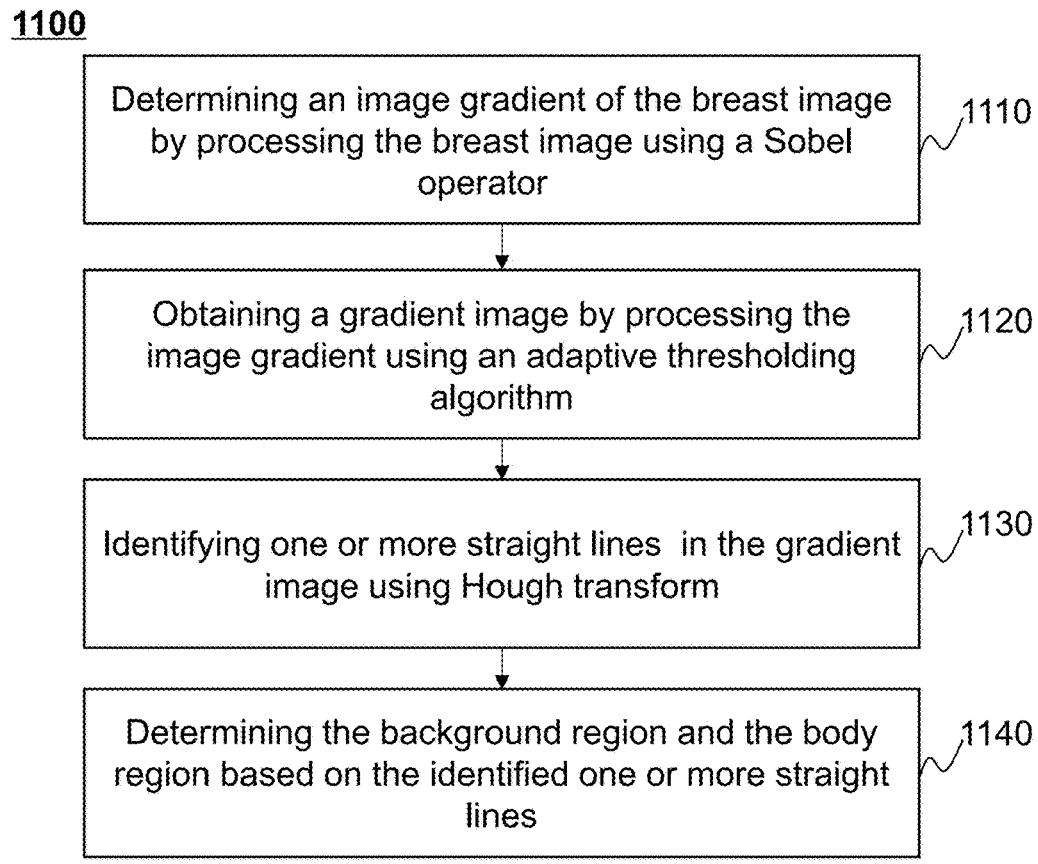
FIG. 11 is a flowchart illustrating an exemplary process for determining a body region and a background region according to some embodiments of the present disclosure.

FIG. 11 is a flowchart illustrating an exemplary process for determining a body region and a background region according to some embodiments of the present disclosure. In some embodiments, the process 1100 may be implemented in the imaging system 100 illustrated in FIG. 1. For example, the process 1100 may be stored in a storage medium (e.g., the storage device 150, or the storage 220 of the processing device 140) as a form of instructions, and can be invoked and/or executed by the processing device 140 (e.g., the processor 210 of the processing device 140, or one or more modules in the processing device 140 illustrated in FIG. 4). The operations of the illustrated process 1100 presented below are intended to be illustrative. In some embodiments, the process 1100 may be accomplished with one or more additional operations not described, and/or without one or more of the operations discussed. Additionally, the order in which the operations of the process 1100 as illustrated in FIG. 11 and described below is not intended to be limiting. In some embodiments, operation 610 of the process 600 in FIG. 6 may be performed based on the process 1100.

In 1110, the processing device 140 (e.g., the image processing module 410) may determine an image gradient of the breast image by processing the breast image using a Sobel operator.

In 1120, the processing device 140 (e.g., the image processing module 410) may obtain a gradient image (e.g., as shown in FIG. 8) by processing the image gradient using an adaptive thresholding algorithm.

In 1130, the processing device 140 (e.g., the image processing module 410) may identify one or more straight lines (e.g., 810 in FIG. 8) in the gradient image using Hough transform.

In 1140, the processing device 140 (e.g., the image processing module 410) may determine the background region and the body region based on the identified one or more straight lines.

In some embodiments, the process 1100 for determining the body region and the background region may be easier and provide a more accurate segmentation result.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

FIG. 12A is a flowchart illustrating an exemplary process for determining a first valley point and a second valley point of a projection curve according to some embodiments of the present disclosure. In some embodiments, the process 1200 may be implemented in the imaging system 100 illustrated in FIG. 1. For example, the process 1200 may be stored in a storage medium (e.g., the storage device 150, or the storage 220 of the processing device 140) as a form of instructions, and can be invoked and/or executed by the processing device 140 (e.g., the processor 210 of the processing device 140, or one or more modules in the processing device 140 illustrated in FIG. 4). The operations of the illustrated process 1200 presented below are intended to be illustrative. In some embodiments, the process 1200 may be accomplished with one or more additional operations not described, and/or without one or more of the operations discussed. Additionally, the order in which the operations of the process 1200 as illustrated in FIG. 12A and described below is not intended to be limiting. In some embodiments, operation 530 of the process 500 in FIG. 5 may be performed based on the process 1200.

In 1210, the processing device 140 (e.g., the curve processing module 420) may obtain a preset distance between the first coordinates of the first valley point and the second valley point, and preset positions of the first valley point and the second valley point in the projection curve. The preset distance and the preset positions may be set based on breast characteristics.

In some embodiment, the preset distance may be a range of values. The preset position may be a certain region. In some embodiments, the preset distance and the preset position may be constant or adjustable depending on different objects (e.g., patients).

In 1220, the processing device 140 (e.g., the curve processing module 420) may determine whether there is any valley point or point whose second coordinate is 0.

In 1230, the processing device 140 (e.g., the curve processing module 420) may determine the first valley point and the second valley point in the projection curve based on the determination result, the preset distance, and the preset positions. The first valley point and the second valley point may satisfy the preset distance and the preset positions. For example, the distance between the first coordinates of the first valley point and the second valley point may be within the preset distance. As another example, the first valley point and the second valley point may be within the preset positions.

The first valley point and the second valley point may represent locations at the junction of the breast and the chest wall of the object in the breast image. However, since the mammilla is a convex structure on the breast, in the projection curve, there may be one or more valley points nearby the peak point that representing the mammilla. In the process 1200, the preset distance and the preset positions may be used to prevent such valley points nearby the peak point that representing the mammilla from being determined as the first valley point and the second valley point.

The projection curve may be divided into two sections by a peak of the projection curve, for example, a first section close to the origin of the coordinate system of the projection curve and a second section away from the origin of the coordinate system of the projection curve.

In the first embodiments, if there is no valley point in the projection curve and both of the two sides of the projection curve have at least one point whose second coordinates is 0, the processing device 140 may determine two points whose second coordinates are 0 as the first valley point and the second valley point. The two points may be in the two sides of the projection curve, respectively. The distance between the first coordinates of the two points may satisfy the preset distance. The first valley point and the second valley point may be located in the preset positions. The first embodiment may correspond to the breast image showing the top view of the breast (e.g., the breast image including only the breast shown in FIG. 12B and/or the breast image including the breast and tissue, such as 1240, other than the breast of the object shown in FIG. 12C).

In the second embodiment, if there is no valley point in the projection curve and only one side of the projection curve has at least one point whose second coordinates is 0, the processing device 140 may determine the point whose first coordinate is 1 as the first valley point and a point whose second coordinate is 0 as the second valley point. The distance between the first coordinates of the two points may satisfy the preset distance. The first valley point and the second valley point may be located in the preset positions.

In the third embodiment, if there is one valley point in the projection curve, the processing device 140 may determine whether the valley point is an effective valley point that is located in the preset positions. In response to a determination that the valley point is the effective valley point, the processing device 140 may determine the valley point as the first valley point and determine a point whose second coordinate is 0 as the second valley point. The distance between the first coordinates of the two points may satisfy the preset distance. The first valley point and the second valley point may be located in the preset positions. In response to a determination that the valley point is not the effective valley point, the processing device 140 may determine the first valley point and the second valley point based on the first or second embodiment.

For example, as shown in FIG. 10, point 1020 (20, 53) and point 1030 (145, 0) may be determined as the first valley point and the second valley point.

In the fourth embodiments, if there are two or more valley points in the projection curve, the processing device 140 may determine whether the two or more valley points are effective valley points that are located in the preset positions. In response to a determination that there are two or more effective valley points, the processing device 140 may determine two of the two or more effective valley points as the first valley point and the second valley point. The distance between the first coordinates of the two points may satisfy the preset distance. In response to a determination that there is at most one effective valley point, the processing device 140 may determine the first valley point and the second valley point based on the first, second, or third embodiment.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

In some embodiments, in the breast image showing the lateral view of the breast (e.g., as shown in FIG. 14 and/or FIG. 17), the area of tissue other than the breast of the object may be larger than that of the breast, which may make the determination of the breast region inaccurate. In this case, the processing device 140 may take measures (e.g., perform the process 1300 in FIG. 13 or the process 1600 in FIG. 16) to reduce the tissue other than the breast during the process for determining the projection curve.

Figure 13:
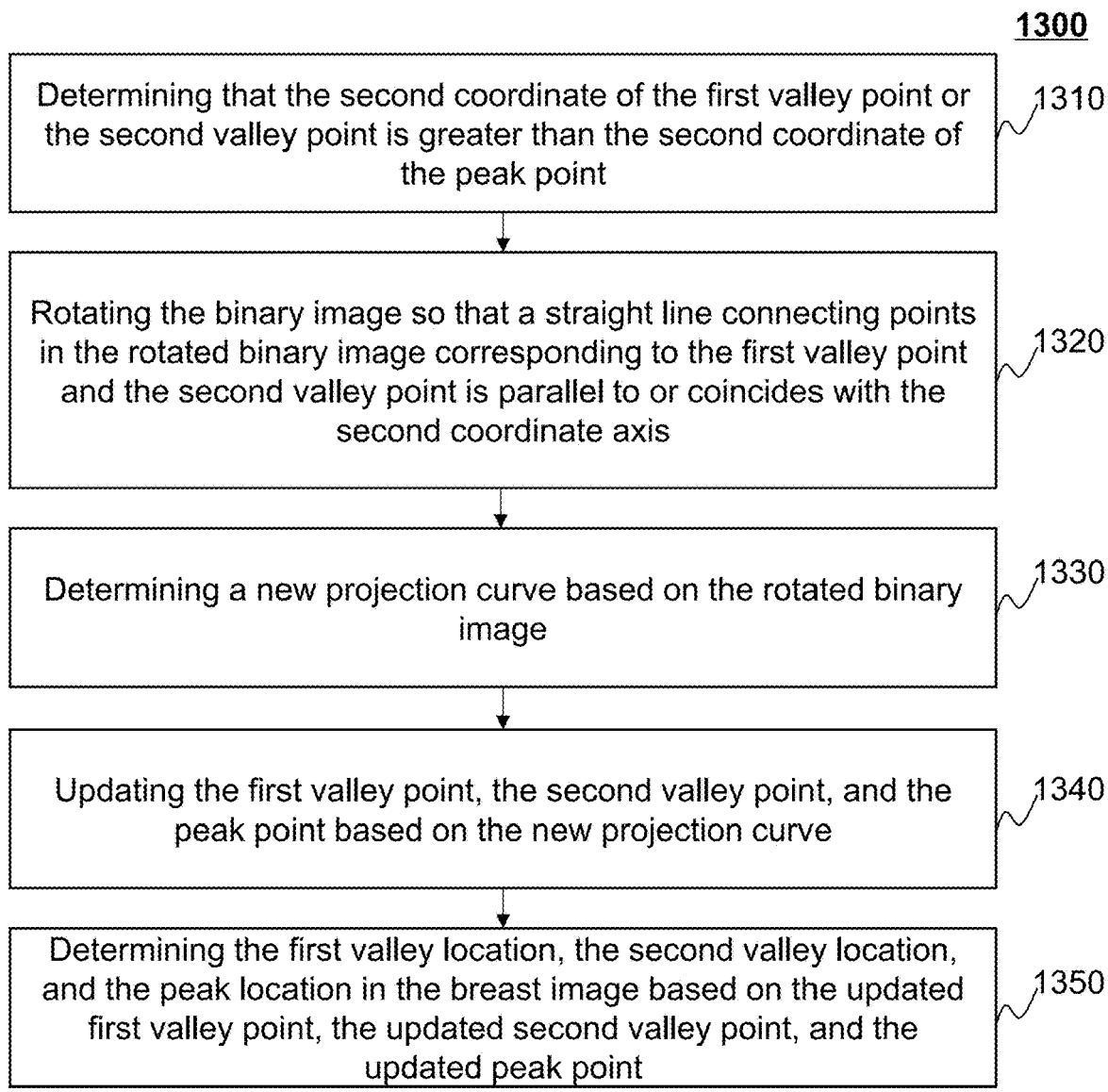
FIG. 13 is a flowchart illustrating an exemplary process for determining a first valley location, a second valley location, and a peak location according to some embodiments of the present disclosure.

FIG. 13 is a flowchart illustrating an exemplary process for determining a first valley location, a second valley location, and a peak location according to some embodiments of the present disclosure. In some embodiments, the process 1300 may be implemented in the imaging system 100 illustrated in FIG. 1. For example, the process 1300 may be stored in a storage medium (e.g., the storage device 150, or the storage 220 of the processing device 140) as a form of instructions, and can be invoked and/or executed by the processing device 140 (e.g., the processor 210 of the processing device 140, or one or more modules in the processing device 140 illustrated in FIG. 4). The operations of the illustrated process 1300 presented below are intended to be illustrative. In some embodiments, the process 1300 may be accomplished with one or more additional operations not described, and/or without one or more of the operations discussed. Additionally, the order in which the operations of the process 1300 as illustrated in FIG. 13 and described below is not intended to be limiting. In some embodiments, the operation 550 of the process 500 in FIG. 5 may be performed based on the process 1300.

In 1310, the processing device 140 (e.g., the curve processing module 420) may determine that the second coordinate of the first valley point or the second valley point is greater than the second coordinate of the peak point. The determination result may indicate that there is too much tissue other than the breast of the object in the breast image (e.g., as shown in FIG. 14), which may make the determination of the breast region inaccurate.

In 1320, the processing device 140 (e.g., the curve processing module 420) may rotate the binary image so that a straight line connecting points in the rotated binary image corresponding to the first valley point and the second valley point is parallel to or coincides with the Y-axis in FIG. 9.

Figure 15:
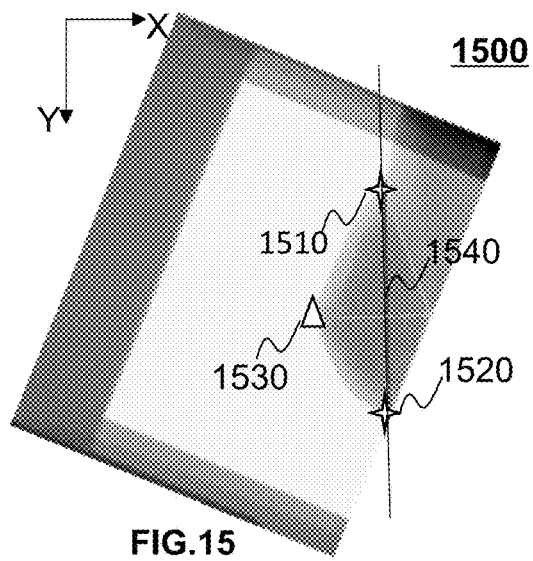
FIG. 15 is a schematic diagram illustrating an exemplary breast image corresponding to a rotated binary image according to some embodiments of the present disclosure.

In 1330, the processing device 140 (e.g., the curve processing module 420) may determine a new projection curve based on the rotated binary image. For example, the breast image 1500 shown in FIG. 15 may correspond to a rotated binary image. Points 1510-1530 in the breast image 1500 may correspond to the first valley point, the second valley point, and the peak point. When determining the new projection curve based on the rotated binary image, the processing device 140 may determine, without considering pixels in the right side of line 1540 connecting the points 1510 and 1520, a plurality of sums each of which is a sum of pixel values of a row of pixels in the rotated binary image. The row of pixels may be arranged along the X-axis direction in FIG. 15 in the rotated binary image. The X-axis and Y-axis in FIG. 15 may be similar to the X-axis and Y-axis in FIG. 9. In this way, the new projection curve of the breast image showing the lateral view of the breast may be determined without considering or by considering a small portion of tissue other than the breast in the breast image, which may make the determination of the breast region more accurate. The new projection curve may be similar to that of the breast image showing the top view of the breast (e.g., as shown in FIG. 12B and/or FIG. 12C).

In 1340, the processing device 140 (e.g., the curve processing module 420) may update the first valley point, the second valley point, and the peak point based on the new projection curve. In some embodiments, the processing device 140 may update the first valley point, the second valley point, and the peak point based on the new projection curve by performing a process similar to the process 1200 in FIG. 12.

In 1350, the processing device 140 (e.g., the curve processing module 420) may determine the first valley location, the second valley location, and the peak location in the breast image based on the updated first valley point, the updated second valley point, and the updated peak point.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 16:
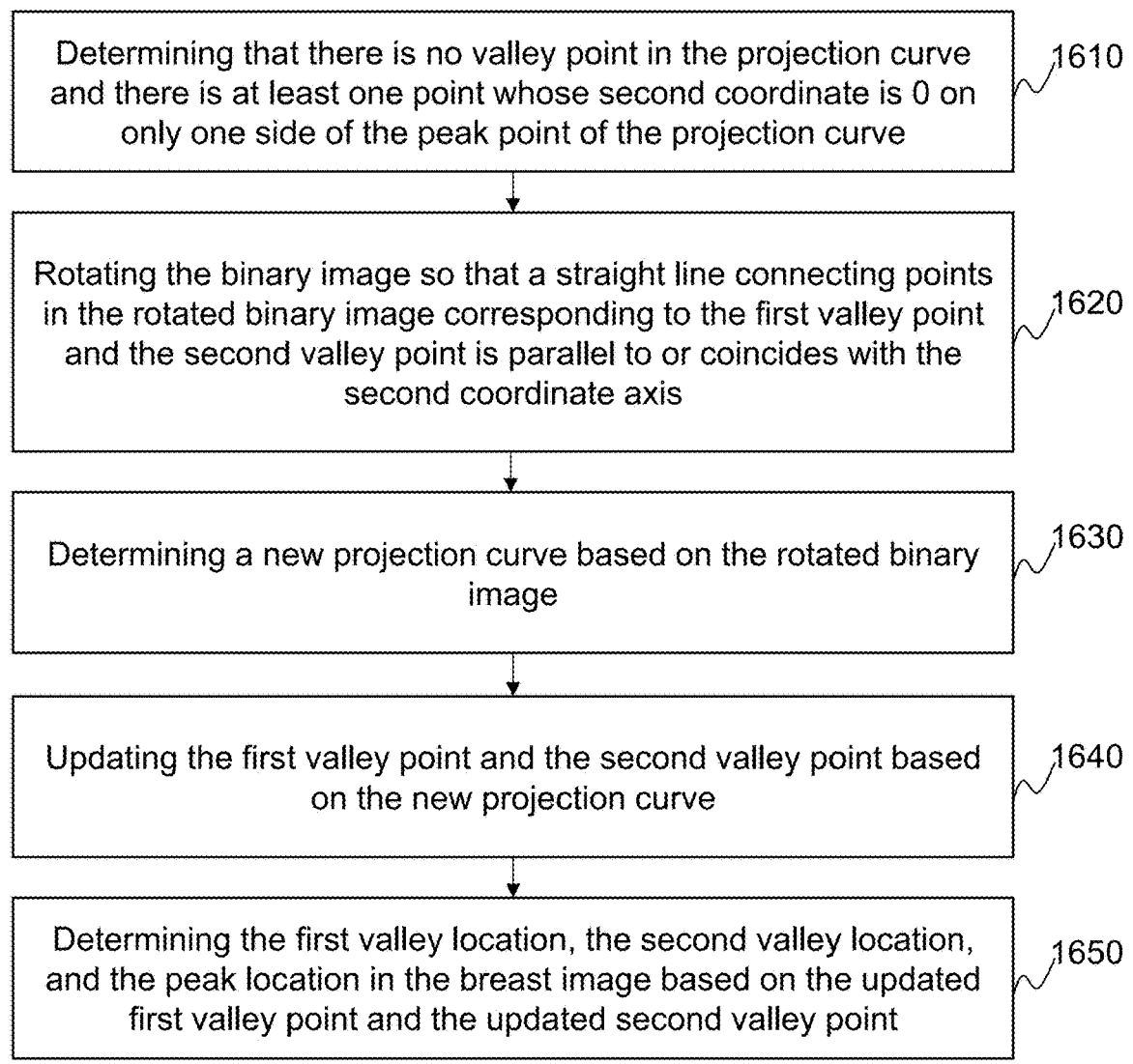
FIG. 16 is a flowchart illustrating an exemplary process for determining a first valley location, a second valley location, and a peak location according to some embodiments of the present disclosure.

FIG. 16 is a flowchart illustrating an exemplary process for determining a first valley location, a second valley location, and a peak location according to some embodiments of the present disclosure. In some embodiments, the process 1600 may be implemented in the imaging system 100 illustrated in FIG. 1. For example, the process 1600 may be stored in a storage medium (e.g., the storage device 150, or the storage 220 of the processing device 140) as a form of instructions, and can be invoked and/or executed by the processing device 140 (e.g., the processor 210 of the processing device 140, or one or more modules in the processing device 140 illustrated in FIG. 4). The operations of the illustrated process 1600 presented below are intended to be illustrative. In some embodiments, the process 1600 may be accomplished with one or more additional operations not described, and/or without one or more of the operations discussed. Additionally, the order in which the operations of the process 1600 as illustrated in FIG. 16 and described below is not intended to be limiting. In some embodiments, the operation 550 of the process 500 in FIG. 5 may be performed based on the process 1600.

Figure 17:
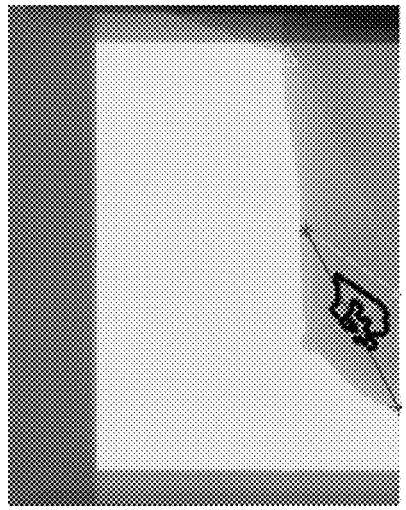
FIG. 17 is a schematic diagram illustrating an exemplary breast image showing a lateral view of a breast according to some embodiments of the present disclosure.

In 1610, the processing device 140 (e.g., the curve processing module 420) may determine that there is no valley point in the projection curve and there is at least one point whose second coordinate is 0 in only one side of the peak point of the projection curve. The determination result may indicate that there is too much tissue other than the breast of the object in the breast image (e.g., as shown in FIG. 17), which may make the determination of the breast region inaccurate.

In 1620, the processing device 140 (e.g., the curve processing module 420) may rotate the binary image so that a straight line connecting points in the rotated binary image corresponding to the first valley point and the second valley point is parallel to or coincides with the Y-axis in FIG. 9.

In 1630, the processing device 140 (e.g., the curve processing module 420) may determine a new projection curve based on the rotated binary image.

In 1640, the processing device 140 (e.g., the curve processing module 420) may update the first valley point, the second valley point, and the peak point based on the new projection curve.

In 1650, the processing device 140 (e.g., the curve processing module 420) may determine the first valley location, the second valley location, and the peak location in the breast image based on the updated first valley point, the updated second valley point, and the updated peak point.

The operations 1620-1650 may be performed similar to the operations 1320-1350, respectively.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

FIG. 18 is a flowchart illustrating an exemplary process for determining a breast region according to some embodiments of the present disclosure. In some embodiments, the process 1800 may be implemented in the imaging system 100 illustrated in FIG. 1. For example, the process 1800 may be stored in a storage medium (e.g., the storage device 150, or the storage 220 of the processing device 140) as a form of instructions, and can be invoked and/or executed by the processing device 140 (e.g., the processor 210 of the processing device 140, or one or more modules in the processing device 140 illustrated in FIG. 4). The operations of the illustrated process 1800 presented below are intended to be illustrative. In some embodiments, the process 1800 may be accomplished with one or more additional operations not described, and/or without one or more of the operations discussed. Additionally, the order in which the operations of the process 1800 as illustrated in FIG. 18 and described below is not intended to be limiting. In some embodiments, operation 560 of the process 500 in FIG. 5 may be performed based on the process 1800.

In 1810, the processing device 140 (e.g., the location processing module 430) may determine a first straight line (e.g., line 1960 in FIG. 19) from the peak location (e.g., point 1930 in FIG. 19). The first straight line may be perpendicular to a second straight line (e.g., line 1950 in FIG. 19) connecting the first valley location and the second valley location (e.g., points 1910 and 1920 in FIG. 19).

In 1820, the processing device 140 (e.g., the location processing module 430) may determine an intersection (e.g., point 1970 in FIG. 19) of the first straight line and the chest-wall side (e.g., the right side 1940 in FIG. 19) of the breast image.

In 1830, the processing device 140 (e.g., the location processing module 430) may determine the breast region in the breast image by connecting the first valley location, the second valley location, and the intersection.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 20:
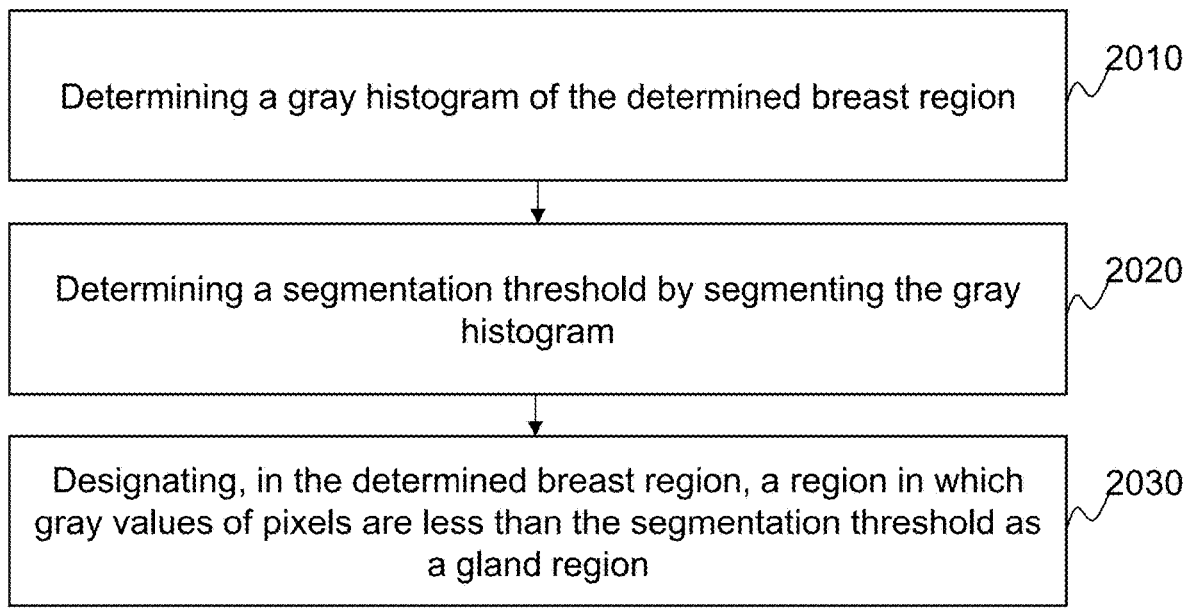
FIG. 20 is a flowchart illustrating an exemplary process for determining a gland region according to some embodiments of the present disclosure.

FIG. 20 is a flowchart illustrating an exemplary process for determining a gland region according to some embodiments of the present disclosure. In some embodiments, the process 2000 may be implemented in the imaging system 100 illustrated in FIG. 1. For example, the process 2000 may be stored in a storage medium (e.g., the storage device 150, or the storage 220 of the processing device 140) as a form of instructions, and can be invoked and/or executed by the processing device 140 (e.g., the processor 210 of the processing device 140, or one or more modules in the processing device 140 illustrated in FIG. 4). The operations of the illustrated process 2000 presented below are intended to be illustrative. In some embodiments, the process 2000 may be accomplished with one or more additional operations not described, and/or without one or more of the operations discussed. Additionally, the order in which the operations of the process 2000 as illustrated in FIG. 20 and described below is not intended to be limiting. In some embodiments, the process 2000 may be performed after the process 500 in FIG. 5.

Figure 21:
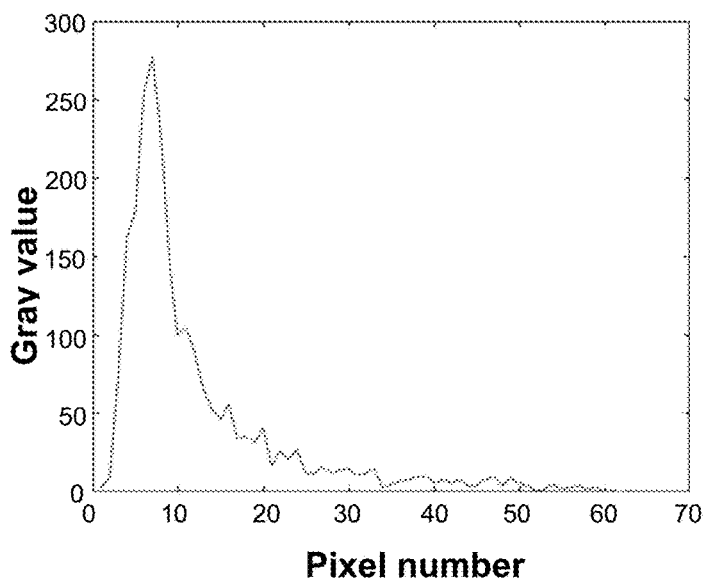
FIG. 21 is a schematic diagram illustrating an exemplary gray histogram of a breast region in a breast image according to some embodiments of the present disclosure.

In 2010, the processing device 140 (e.g., the gland determination module 440) may determine a gray histogram of the breast region determined in operation 560 of the process 500 in FIG. 5. For example, as shown in FIG. 21, for each point in the gray histogram, a first coordinate on a first coordinate axis (e.g., the vertical coordinate axis of the gray histogram in FIG. 21) of the point may represent a gray value, and a second coordinate on a second coordinate axis (e.g., the horizontal coordinate axis of the gray histogram in FIG. 21) of the point may represent the number (or a count) of pixels with the gray value.

In 2020, the processing device 140 (e.g., the gland determination module 440) may determine a segmentation threshold by segmenting the gray histogram. In some embodiments, the processing device 140 may determine the segmentation threshold using an Otsu algorithm.

Figure 22:
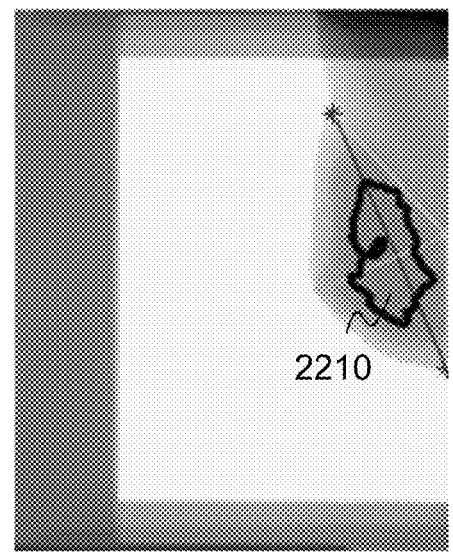
FIG. 22 is a schematic diagram illustrating an exemplary gland region in a breast image according to some embodiments of the present disclosure.

In 2030, the processing device 140 (e.g., the gland determination module 440) may designate, in the determined breast region, a region in which gray values of pixels are less than the segmentation threshold as a gland region (e.g., region 2210 in FIG. 22).

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 23:
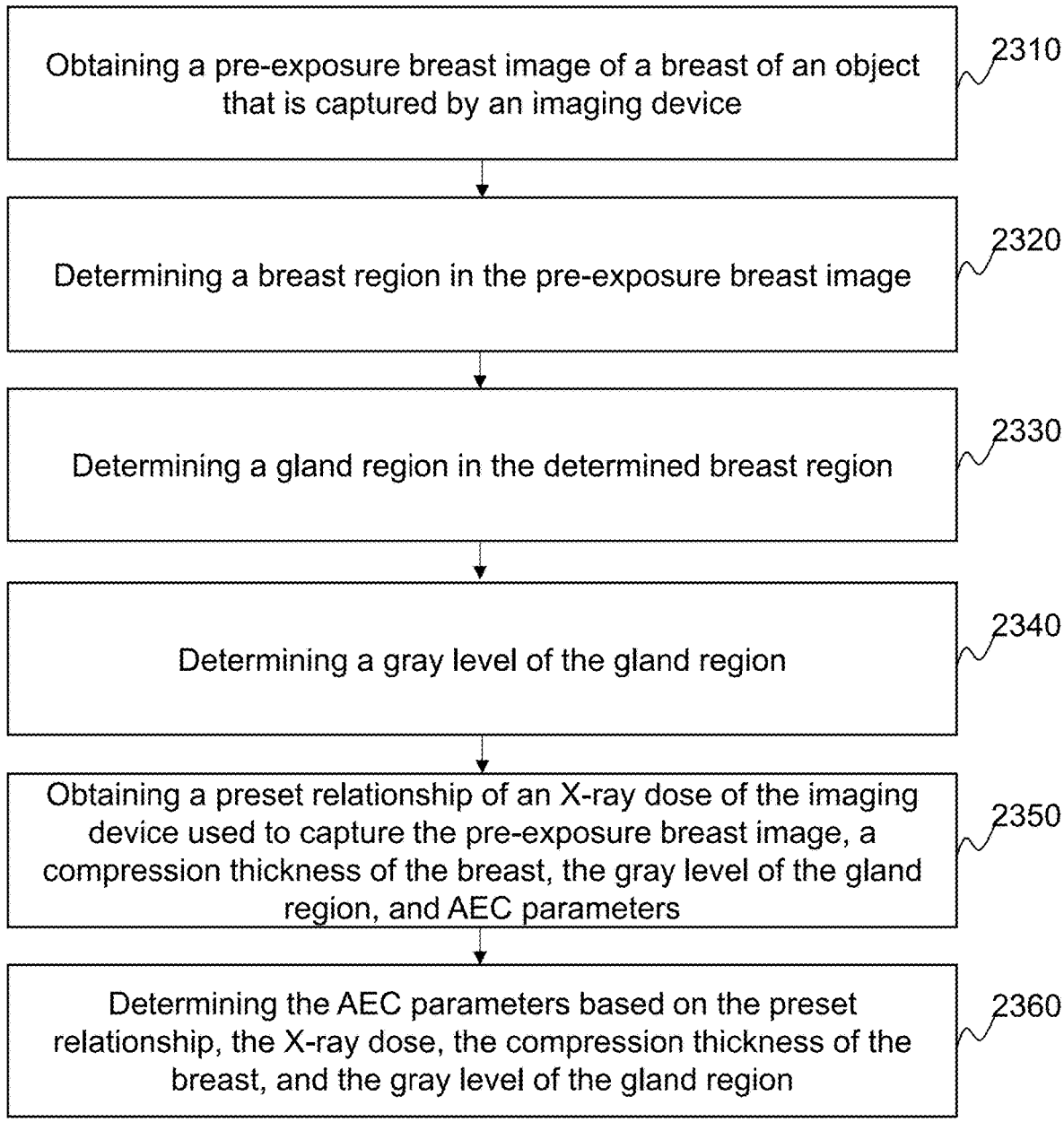
FIG. 23 is a flowchart illustrating an exemplary process for determining AEC parameters of an imaging device according to some embodiments of the present disclosure.

FIG. 23 is a flowchart illustrating an exemplary process for determining AEC parameters of an imaging device according to some embodiments of the present disclosure. In some embodiments, the process 2300 may be implemented in the imaging system 100 illustrated in FIG. 1. For example, the process 2300 may be stored in a storage medium (e.g., the storage device 150, or the storage 220 of the processing device 140) as a form of instructions, and can be invoked and/or executed by the processing device 140 (e.g., the processor 210 of the processing device 140, or one or more modules in the processing device 140 illustrated in FIG. 4). The operations of the illustrated process 2300 presented below are intended to be illustrative. In some embodiments, the process 2300 may be accomplished with one or more additional operations not described, and/or without one or more of the operations discussed. Additionally, the order in which the operations of the process 2300 as illustrated in FIG. 23 and described below is not intended to be limiting.

In 2310, the processing device 140 (e.g., the parameter determination module 450) may obtain a pre-exposure breast image of a breast of an object that is acquired by an imaging device (e.g., the imaging device 110). The imaging device 110 may be an X-ray device. In some embodiments, before acquiring a formal breast image of a breast, the imaging system 100 may acquire a pre-exposure breast image of the breast by scanning the breast using a relatively low dose of X-rays (also referred to as a pre-exposure dose of X-rays). The pre-exposure breast image may be used to estimate AEC parameters of the imaging device 110 used for acquiring the formal breast image of the breast.

Before the breast is scanned by the imaging device 110, the breast may be compressed to a certain thickness and be fixed to the breast-holder tray by the compression pad of the imaging device 110.

In some embodiments, the processing device 140 may determine the pre-exposure dose of X-rays based on the breast. According to whether the glandular tissue content in the breast is greater than 75%, the breast may be divided into two categories: non-dense breast and dense breast. When the dense breast is scanned to obtain the pre-exposure breast image, a relatively high dose of X-rays may be used in order to obtain good image quality. When the non-dense breast is scanned to obtain the pre-exposure breast image, a relatively low dose of X-rays may be used in order to avoid overexposure. Optionally, the pre-exposure dose of X-rays corresponding to the dense breast may be set as: X-rays of 30 kV-35 kV and 20 mA-50 mA (where kV (kilo-volts) and mA (milliampere) represent the dose of X-rays); the pre-exposure dose of X-rays corresponding to the non-dense breast may be set as: X-rays of 25 kv-29 kv and 5 mAs-19 mAs, which can reduce or avoid the under-exposure or over-exposure and improve the image quality.

In 2320, the processing device 140 (e.g., the parameter determination module 450) may determine a breast region in the pre-exposure breast image. The processing device 140 may determine the breast region based on the process for determining the breast region disclosed in the present disclosure (e.g., the process 500 in FIG. 5).

In 2330, the processing device 140 (e.g., the parameter determination module 450) may determine a gland region in the determined breast region. The processing device 140 may determine the breast region based on the process 2000 in FIG. 20.

In 2340, the processing device 140 (e.g., the parameter determination module 450) may determine a gray level of the gland region.

In 2350, the processing device 140 (e.g., the parameter determination module 450) may obtain a preset relationship of the pre-exposure X-ray dose, a compression thickness of the breast, the gray level of the gland region, and AEC parameters.

In 2360, the processing device 140 (e.g., the parameter determination module 450) may determine the AEC parameters based on the preset relationship, the pre-exposure dose, the compression thickness of the breast, and the gray level of the gland region.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

With the rapid development of image processing technology, image enhancement technology has been widely used in biomedical engineering, aerospace and aviation technology, communication engineering and other fields. In the image enhancement process, the multi-resolution analysis algorithm is usually used for image decomposition processing. Commonly used enhancement algorithms include Gauss-Laplace pyramid decomposition, wavelet decomposition, and so on. But the algorithm is to adjust the coefficients of each decomposition layer by designing some equations and parameters, and finally reconstructed into an enhanced image. These adjusted parameters are very numerous, and the decomposition layers that need to be adjusted are also very numerous, and the parameter adjustment is performed manually, and the processing process is complicated and cumbersome.

Another aspect of the present disclosure may provide systems and/or method for image enhancement using a machine learning model.

Figure 24:
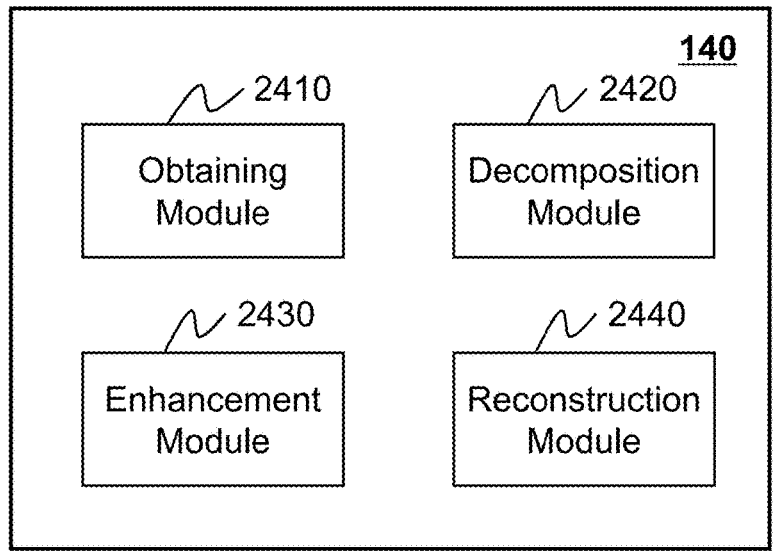
FIG. 24 is a schematic block diagram illustrating an exemplary processing device according to some embodiments of the present disclosure.

FIG. 24 is a schematic block diagram illustrating an exemplary processing device according to some embodiments of the present disclosure. The processing device 140 may include an obtaining module 2410, a decomposition module 2420, an enhancement module 2430, and a reconstruction module 2440.

The obtaining module 2410 may be configured to obtain an original image. The decomposition module 2420 may be configured to obtain a plurality of decomposition coefficients of the original image by decomposing the original image. The enhancement module 2430 may be configured to obtain at least one enhancement coefficient by performing enhancement to at least one of the plurality of decomposition coefficients using a machine learning model. The reconstruction module 2440 may be configured to obtain an enhanced image corresponding to the original image based on the decomposition coefficients and the at least one enhancement coefficient.

The modules in the processing device 140 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. Two or more of the modules may be combined as a single module, and any one of the modules may be divided into two or more units.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 140 may further include a storage module (not shown in FIG. 24). The storage module may be configured to store data generated during any process performed by any component of in the processing device 140. As another example, each of the components of the processing device 140 may include a storage device. Additionally or alternatively, the components of the processing device 140 may share a common storage device.

Figure 25:
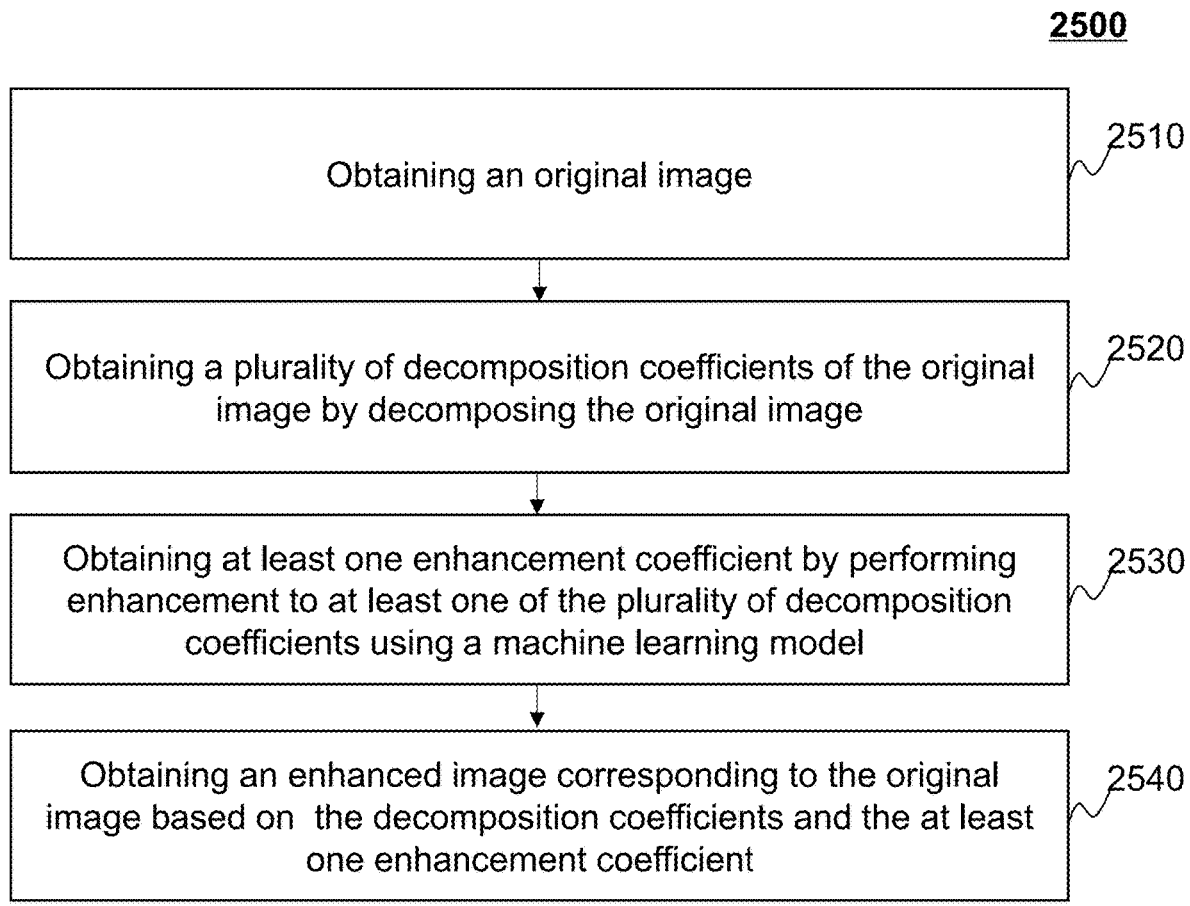
FIG. 25 is a flowchart illustrating an exemplary process for image enhancement according to some embodiments of the present disclosure.

FIG. 25 is a flowchart illustrating an exemplary process for image enhancement according to some embodiments of the present disclosure. In some embodiments, the process 2500 may be implemented in the imaging system 100 illustrated in FIG. 1. For example, the process 2500 may be stored in a storage medium (e.g., the storage device 150, or the storage 220 of the processing device 140) as a form of instructions, and can be invoked and/or executed by the processing device 140 (e.g., the processor 210 of the processing device 140, or one or more modules in the processing device 140 illustrated in FIG. 24). The operations of the illustrated process 2500 presented below are intended to be illustrative. In some embodiments, the process 2500 may be accomplished with one or more additional operations not described, and/or without one or more of the operations discussed. Additionally, the order in which the operations of the process 2500 as illustrated in FIG. 25 and described below is not intended to be limiting.

In 2510, the processing device 140 (e.g., the obtaining module 2410) may obtain an original image. In some embodiments, the original image may be a three-dimensional (3D) image and/or a two-dimensional (2D) image. In some embodiments, the original image may include an image of at least one organ or tissue. The organs include, but are not limited to, the brain, lungs, heart, kidneys, liver, or the like. The tissue may include, but is not limited to, epithelial tissue, connective tissue, neural tissue, muscle tissue, or the like. In some embodiments, the original image may include multiple images of the same type, such as MR images, CT images, PET-CT images, PET-MR images, or the like. In some embodiments, the original image may include multiple images of different types. Taking the brain MR image as an example, the original image may include multiple images including a T1 weighted image, a T2-weighted image, a fluid attenuated inversion recovery (FLAIR) sequence image of the brain, or the like.

In some embodiments, the processing device 140 may perform a pre-processing operation on the original image. The pre-processing operation may include: adjusting display parameters of the original image based on a preset value condition, and obtaining a new image by transforming the display parameters of the original image. The display parameter of an image refers to the numerical information that is included in the image and may be used to adjust the display effect of the image. In some embodiments, the display parameter may include the resolution, size, direction of the image, brightness, contrast, length-width ratio, color, or the like. The value condition may be a range of values preset according to the corresponding display parameter, and the range of values may be set in advance according to the specific application situation, for example, the size of the image may be set to 512×512. By pre-processing the original image, it is possible to improve the image quality for image enhancement, speed up the processing speed of the image enhancement, and improve the accuracy of the image enhancement.

In 2520, the processing device 140 (e.g., the decomposition module 2420) may obtain a plurality of decomposition coefficients of the original image by decomposing the original image. In some embodiments, the original image may be decomposed using a multi-resolution analysis algorithm to obtain a plurality of decomposition coefficients of the original image. The multi-resolution analysis algorithm may include a Gauss-Laplace pyramid decomposition algorithm, a wavelet decomposition algorithm, or the like.

In some embodiments, the Gauss-Laplace pyramid decomposition algorithm may be used to decompose the original image.

Figure 28:
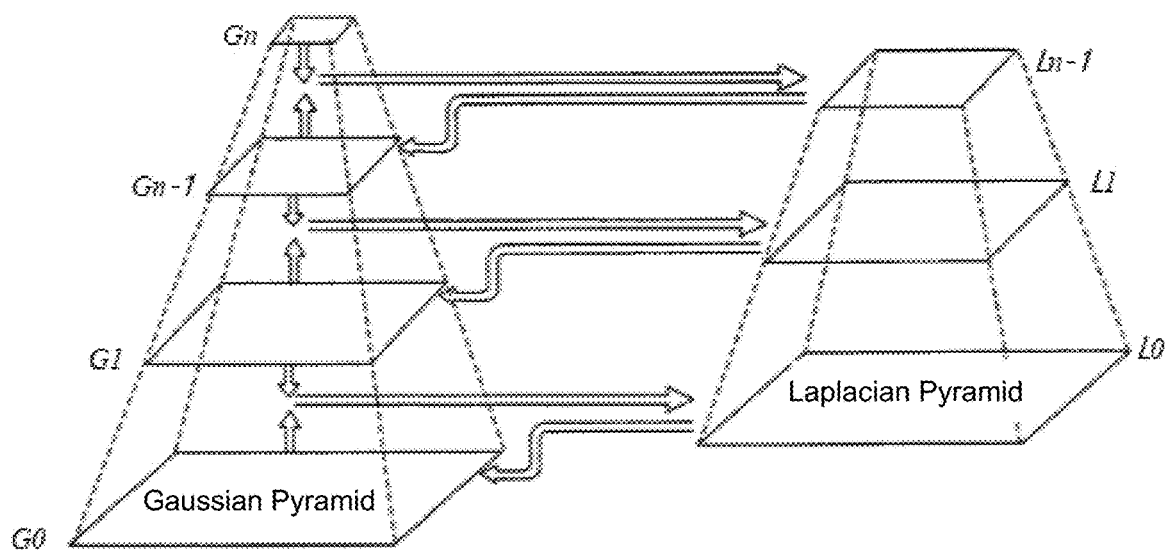
FIG. 28 is a schematic diagram of an exemplary Gauss-pyramid decomposition algorithm according to some embodiments of the present disclosure.

FIG. 28 is a schematic diagram of an exemplary Gauss-pyramid decomposition algorithm according to some embodiments of the present disclosure.

As shown in FIG. 28, the Gauss-Laplace pyramid decomposition algorithm may include: performing Gaussian decomposition to the original image, and obtaining a Gaussian pyramid of the multi-layer Gaussian sub-image $G_j$ of the original image and a Laplacian pyramid of the multi-layer Laplacian sub-image $L_j$.

In some embodiments, obtaining the Gaussian pyramid may include the following operations. The original image may be used as the $0^{th}$ layer $G_0$ of the Gaussian pyramid. The first layer sub-image $G_1$ may be obtained by performing low-pass filtering and downsampling to the original image. Then, the second layer sub-image $G_2$ may be obtained by performing low-pass filtering and downsampling to the first layer sub-image $G_1$. The above operation may be performed successively until the $n^{th}$ layer sub-image $G_n$ is obtained, thereby obtaining a Gaussian pyramid having a multi-layer Gaussian sub-image $G_j$ ($0<=j<=n$). The number of decomposition layers n may be the number of layers of the Gaussian pyramid, which may be set in advance. In some embodiments, the number of decomposition layers n may be obtained according to the feature of the original image. In some embodiments, the number of decomposition layers n may depend on the location information that needs to be enhanced in the image. When the original image is a medical image, for an organ or tissue with a relatively high density, the number of decomposition layers may be 5-7 layers, and for an organ or tissue with a relatively low density, for example, soft tissue, the number of decomposition layers may be 7-10 layers. In some embodiments, the low-pass filtering may be performed to the image using a 5*5 Gaussian convolution kernel. In some embodiments, downsampling the image may include sampling the image in a step of 2.

In some embodiments, obtaining the Laplacian pyramid may include the following operations. Starting from the top of the Gaussian pyramid, that is, the $n^{th}$ layer, a Gaussian sub-image $G_{n-1}'$ may be obtained by performing up-sampling and low-pass filtering to the Gaussian sub-image $G_n$ in the $n^{th}$ layer. The Gaussian sub-image $G_{n-1}'$ may have a same resolution as the Gaussian sub-image $G_{n-1}$ originally in the $(n-1)^{th}$ layer. The difference between $G_{n-1}$ and $G_{n-1}'$ may be the Laplacian sub-image $L_{n-1}$ of the $(n-1)^{th}$ layer. A Gaussian sub-image $G_{n-2}'$ may be obtained by performing up-sampling and low-pass filtering to the Gaussian sub-image $G_{n-1}$ in the $(n-1)^{th}$ layer. The Gaussian sub-image $G_{n-2}'$ may have a same resolution as the Gaussian sub-image $G_{n-2}$ originally in the $(n-2)^{th}$ layer. The difference between $G_{n-2}$ and $G_{n-2}'$ may be the Laplacian sub-image $L_{n-2}$ of the $(n-2)^{th}$ layer. The above operation may be performed successively until the Laplacian sub-image $L_0$ of the $0^{th}$ layer is obtained, thereby obtaining a Laplacian pyramid having a multi-layer Laplacian sub-image $L_j$ ($0<=j<=(n-1)$). In some embodiments, the up-sampling of the image may include inserting a new element between the pixels using a suitable interpolation algorithm based on the original image pixels. The interpolation algorithm may include a conventional interpolation, an interpolation based on edge image, a region-based image interpolation, or the like. In some embodiments, the up-sampling of the image may include interpolating the image in a step of two.

In some embodiments, the Gaussian sub-image $G_j$ ($0<=j<=n$) and the Laplacian sub-image $L_j$ ($0<=j<=(n-1)$) may be the decomposition coefficient obtained based on the Gauss-Laplace pyramid decomposition algorithm.

In some embodiments, the original image may be decomposed using a wavelet decomposition algorithm.

Figure 29:
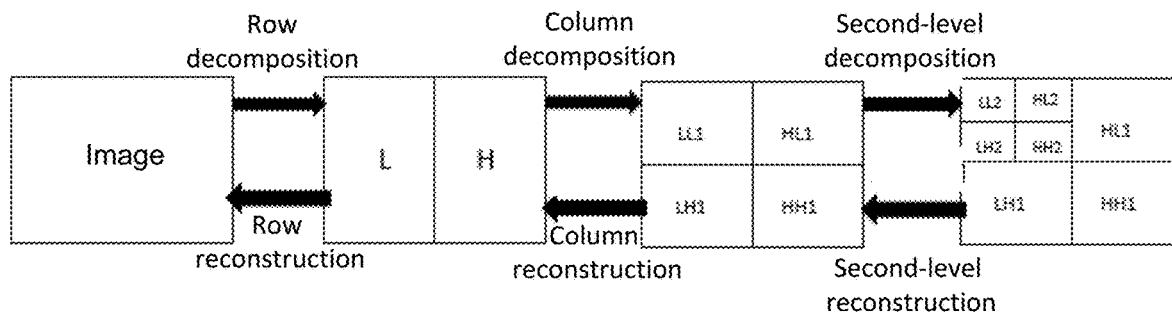
FIG. 29 is a schematic diagram of an exemplary wavelet decomposition algorithm according to some embodiments of the present disclosure.

FIG. 29 is a schematic diagram of an exemplary wavelet decomposition algorithm according to some embodiments of the present disclosure.

As shown in FIG. 29, the wavelet decomposition algorithm may include the following operations. Firstly, the low frequency component L and the high frequency component H of the original image in the horizontal direction may be obtained by decomposing the original image using the discrete wavelet transform algorithm. Then, sub-images $LL_1$, $LH_1$, $HL_1$, and $HH_1$ of the original image may be obtained by performing column decomposition to the transformed data using the discrete wavelet transform algorithm. Performing a row decomposition and a column decomposition to an image may be a first-level decomposition to the image. The sub-image $LL_1$ may be low-frequency components in the horizontal and vertical directions. The sub-image $LH_1$ may be a low-frequency component in the horizontal direction and a high-frequency component in the vertical direction. The sub-image HU may be a high-frequency component in the horizontal direction and a low-frequency component in the vertical direction. The sub-image $HH_1$ may be high-frequency components in the horizontal and vertical directions. In some embodiments, a two-level decomposition may be performed to the low-frequency component $LL_1$, that is, sub-images $LL_2$, $HL_2$, $LH_2$, and $HH_2$ may be obtained by performing row decomposition and column decomposition to the low-frequency component $LL_1$ using the discrete wavelet transform algorithm. By analogy, sub-images $LL_{(k+1)}$, $HL_{(k+1)}$, $LH_{(k+1)}$, and $HH_{(k+1)}$ may be obtained by performing $(k+1)^{th}$ decomposition to the sub-image $LL_k$ ($1<=k$). In some embodiments, the decomposition level m may be preset according to specific application conditions, for example, the decomposition level m may be set to 2. In some embodiments, the wavelet function used in the wavelet transform algorithm may include a Moret wavelet function, a Mexican Hat wavelet function, a Meyer wavelet function, a Haar wavelet function, a db6 wavelet function, a sym6 wavelet function, or the like.

In some embodiments, the sub-images $LL_k$, $HL_k$, $LH_k$, and $HH_k$ ($1<=k$) may be the decomposition coefficients obtained based on the wavelet decomposition algorithm.

In 2530, the processing device 140 (e.g., the enhancement module 2430) may obtain at least one enhancement coefficient by performing enhancement to at least one of the plurality of decomposition coefficients using a machine learning model.

In some embodiments, a coefficient enhancement model may be used to obtain at least one enhancement coefficient by processing the decomposition coefficients of the original image. In some embodiments, a part of the decomposition coefficients of the original image may be processed to obtain corresponding enhancement coefficients. In some embodiments, all of the decomposition coefficients of the original image may be processed to obtain corresponding enhancement coefficients. In some embodiments, the decomposition coefficients may be input into the coefficient enhancement model one by one to obtain corresponding enhancement coefficients. In some embodiments, all of the decomposition coefficients may be input together into the coefficient enhancement model to obtain the corresponding enhancement coefficients.

In some embodiments, the machine learning model may be a trained deep learning model. A neural network model may include a deep belief network model, a Visual Geometry Group (VGG) convolutional neural network, OverFeat, Region-Convolutional Neural Network (R-CNN), spatial pyramid pooling network (SPP-Net), Fast R-CNN, Faster R-CNN, Region-based Fully Convolution Network (R-FCN), Deeply Supervised Object Detector (DSOD), or the like.

In some embodiments, the machine learning model may be a coefficient enhancement model. The coefficient enhancement model may be obtained based on the following training operations. A training set may be obtained. The training set may include a plurality of sample pairs. The sample pair may include a sample image and an enhanced image corresponding to the sample image. The preliminary model may be trained using the training set to obtain a coefficient enhancement model. Details regarding model training may be found elsewhere in the present disclosure (e.g., the description in connection with FIG. 4 and/or FIG. 5).

In some embodiments, the processing device 140 or an external device communicating with the imaging system 100 may provide the trained model.

In some embodiments, when the sample images in the training set are decomposed using the Gauss-Laplacian pyramid decomposition algorithm, the coefficient enhancement model may perform enhancement to the Laplacian sub-image $L_j$ ($0<=j<=(n-1)$) in the decomposition coefficients to obtain an enhancement coefficient $L_j'$ ($0<=j<=(n-1)$). In some embodiments, the Gaussian sub-image $G_j$ ($0<=j<=n$) in the decomposition coefficients may also be enhanced by the coefficient enhancement model. In some embodiments, both of the Laplacian sub-image $L_j$ ($0<=j<=(n-1)$) and the Gaussian sub-image $G_j$ ($0<=j<=n$) in the decomposition coefficients may be enhanced by the coefficient enhancement model.

In some embodiments, when the sample images in the training set are decomposed using the wavelet decomposition algorithm, the coefficient enhancement model may perform enhancement to one or more of the decomposition coefficients $LL_k$, $HL_k$, $LH_k$, $HH_k$ to obtain one or more of the corresponding enhancement coefficients $LL_k$, $HL_k$, $LH_k$, $HH_k$.

In 2540, the processing device 140 (e.g., the reconstruction module 2440) may obtain an enhanced image corresponding to the original image based on the decomposition coefficients and the at least one enhancement coefficient.

In some embodiments, the decomposition coefficients that are reconstructed may have been enhanced, or some of the decomposition coefficients that are reconstructed may have been enhanced.

In some embodiments, when the Gauss-Laplace pyramid decomposition algorithm is used to decompose the original image, the image reconstruction may include performing reconstruction using the enhanced Laplacian sub-images and/or the enhanced Gaussian sub-images to obtain an enhanced image corresponding to the original image. In some embodiments, some or all of the decomposition coefficients obtained by the Gauss-Laplacian pyramid decomposition algorithm may be replaced with the enhanced sub-images, and image reconstruction may be performed to obtain an enhanced image corresponding to the original image.

In some embodiments, when the original image is decomposed using the wavelet decomposition algorithm, image reconstruction may include performing discrete wavelet inverse transform on each column of image data composed of enhancement coefficients $LL_k'$, $HL_k'$, $LH_k'$, $HH_k'$, and performing discrete wavelet inverse transform on each row of the image data. In this way, the enhanced image corresponding to the original image may be obtained.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

FIG. 26 is a flowchart illustrating an exemplary process for obtaining a training set according to some embodiments of the present disclosure.

In some embodiments, the process 2600 may be implemented in the imaging system 100 illustrated in FIG. 1. For example, the process 2600 may be stored in a storage medium (e.g., the storage device 150, or the storage 220 of the processing device 140) as a form of instructions, and can be invoked and/or executed by the processing device 140 (e.g., the processor 210 of the processing device 140, or one or more modules in the processing device 140 illustrated in FIG. 24). The operations of the illustrated process 2600 presented below are intended to be illustrative. In some embodiments, the process 2600 may be accomplished with one or more additional operations not described, and/or without one or more of the operations discussed. Additionally, the order in which the operations of the process 2600 as illustrated in FIG. 26 and described below is not intended to be limiting. In some embodiments, the process 2600 may be used to obtain the training set configured to training a preliminary model to obtain the machine learning model.

As shown in FIG. 26, the process 2600 for obtaining the training set may include:

Operation 2610: obtaining a plurality of first decomposition coefficients of a sample image and a plurality of second decomposition coefficients of an enhanced image corresponding to the sample image by decomposing the sample image and the corresponding enhanced image; and.

Operation 2620: determining the plurality of first decomposition coefficients and the plurality of second decomposition coefficients as a sample pair.

In some embodiments, the sample image may be a three-dimensional (3D) image and/or a two-dimensional (2D) image. In some embodiments, the sample image may include an image of at least one organ or tissue. The organs include, but are not limited to, the brain, lungs, heart, kidneys, liver, or the like. The tissue may include, but is not limited to, epithelial tissue, connective tissue, neural tissue, muscle tissue, or the like. In some embodiments, the sample image may include multiple images of the same type, such as MR images, CT images, PET-CT images, PET-MR images, or the like. In some embodiments, the sample image may include multiple images of different types. Taking the brain MR image as an example, the sample image may include multiple images including a T1 weighted image, a T2-weighted image, a fluid attenuated inversion recovery (FLAIR) sequence image of the brain, or the like.

In some embodiments, the processing device 140 may perform a pre-processing operation on the sample image. The pre-processing operation may include: adjusting display parameters of the sample image based on a preset value condition, and obtaining a new image by transforming the display parameters of the sample image. The display parameter of an image refers to the numerical information that is included in the image and may be used to adjust the display effect of the image. In some embodiments, the display parameter may include the resolution, size, direction of the image, brightness, contrast, length-width ratio, color, or the like. The value condition may be a range of values preset according to the corresponding display parameter, and the range of values may be set in advance according to the specific application situation, for example, the size of the image may be set to 512×512. By pre-processing the sample image, it is possible to improve the quality of images used for model training, speed up the training speed, and improve the training accuracy. The distribution condition may be a preset condition that needs to satisfy based on different display parameters, for example, an average distribution, a random distribution, and a Gaussian distribution, etc. In some embodiments, according to the preset distribution condition of the display parameters, the display parameters of the sample image may be processed to obtain a new sample image, thereby obtaining more sample images, which may realize data amplification, and add training data for training the neural network model.

In some embodiments, the enhanced image may be deemed as an image obtained after any one of the image processing algorithms performed on the original image. The image processing algorithms may include, but are not limited to, denoising, scaling, binarization, grayscale, brightness adjustment, blurring, equalization, filtering, image segmentation, or the like. In some embodiments, the enhancement may be further understood as adding some information or transformed data to the original image by certain means, selectively highlighting the feature of interest in the image or suppressing (masking) some unwanted features in the image, so that the image and the visual response characteristic are matched. The sample image may be processed by performing a histogram equalization algorithm, a gamma conversion algorithm, an exponential image enhancement algorithm, a logarithmic image enhancement algorithm, or the like, or any combination thereof to obtain an enhanced image corresponding to the sample image. The present disclosure does not impose any restriction on the type of enhancement processing, and any image obtained by the processing of the original image to change original image's rendering effect may be determined as the enhanced image.

In some embodiments, the sample image and the enhanced image of the sample image may be decomposed using a multi-resolution analysis algorithm to obtain a plurality of decomposition coefficients of the sample image and a plurality of decomposition coefficients of the enhanced image. The multi-resolution analysis algorithm may include a Gauss-Laplace pyramid decomposition algorithm, a wavelet decomposition algorithm, or the like.

In some embodiments, the Gauss-Laplace pyramid decomposition algorithm may be used to decompose the sample image and the enhanced image corresponding to the sample image. The Gauss-Lapras Gaussian pyramid decomposition algorithm has been described in FIG. 28, and will not be described here.

In some embodiments, Gaussian decomposition may be performed on the sample image $G^1$ to obtain a Gaussian pyramid of the multi-layer Gaussian sub-image $G^1_j$ of the sample image and a Laplacian pyramid of the multi-layer Laplacian sub-image $L^1_j$. In some embodiments, the enhanced image $G^{1'}$ corresponding to the sample image may be Gaussian-decomposed to obtain a Gaussian pyramid of the multi-layer Gaussian sub-image $G^{1'}$ of the sample image and a Laplacian pyramid of the multi-layer Laplacian sub-image $L^{1'}_j$.

In some embodiments, the number of decomposition layers n may be obtained according to the feature of the sample image, for example, the number of decomposition layers n may be set to 3.

In some embodiments, the Gaussian sub-image $G^1$ ($0<=j<=n$) and the Laplacian sub-image $L^1$ ($0<=j<=(n-1)$) may be used as the decomposition coefficients obtained after the sample image $G^1$ is subjected to the Gauss-Laplacian pyramid decomposition algorithm. Alternatively, only the Laplacian sub-image $L^1$ ($0<=j<=(n-1)$) may be used as the decomposition coefficient obtained after the sample image $G^1$ is subjected to the Gauss-Laplacian pyramid decomposition algorithm. Both of the Gaussian sub-image $G^{1'}$ ($0<=j<=n$) and the Laplacian sub-image $L^{1'}$ ($0<=j<=(n-1)$) may be used as decomposition coefficients obtained by the Gauss-Laplace pyramid decomposition method of the enhanced image $G^{1'}$ corresponding to the sample image. Alternatively, only the Laplacian sub-image $L^{1'}$ ($0<=j<=(n-1)$) may be taken as the decomposition coefficient obtained after the Gauss-Laplace pyramid decomposition algorithm is performed on the enhanced image $G^{1'}$ corresponding to the sample image.

In some embodiments, the wavelet image decomposition algorithm may be used to decompose the sample image. The wavelet decomposition algorithm has been described in FIG. 29, and will not be described here.

In some embodiments, the sample image $G^2$ may be subjected to wavelet decomposition processing to obtain sub-images $LL^2_{(k+1)}$, $HL^2_{(k+1)}$, $LH^2_{(k+1)}$, and $HH^2_{(k+1)}$. In some embodiments, the decomposition level m may be preset according to specific application conditions, for example, the decomposition level m may be set to 2.

In some embodiments, the enhanced image $G^{2'}$ corresponding to the sample image may be subjected to wavelet decomposition processing to obtain sub-images $LL^{2'}_{(k+1)}$, $HL^{2'}_{(k+1)}$, $LH^{2'}_{(k+1)}$, and $HH^{2'}_{(k+1)}$. In some embodiments, the decomposition level m may be preset according to specific application conditions, for example, the decomposition level m may be set to 2.

In some embodiments, the sub-images $LL^2_k$, $HL^2_k$, $LH^2_k$, and $HH^2_k$ ($1<=k$) may be decomposition coefficients obtained after the sample image $G^2$ undergoes the wavelet decomposition algorithm. In some embodiments, the sub-images $LL^{2'}_{(k+1)}$, $HL^{2'}_{(k+1)}$, $LH^{2'}_{(k+1)}$, $HH^{2'}_{(k+1)}$ may be decomposition coefficients obtained after the enhancement image $G^{2'}$ corresponding to the sample image is subjected to the wavelet decomposition algorithm.

In some embodiments, a sample pair may include: a combination of a sample image and an enhanced image corresponding to the sample image, or may include: a plurality of decomposition coefficients of a sample image and a plurality of decomposition coefficients of the enhanced image corresponding to the sample image. For example, one sample pair may include the Gaussian sub-image $G^1_j$ of the sample image $G^1$ ($0<=j<=n$), the Laplacian sub-image $L^1_j$ ($0<=j<=(n-1)$), the Gaussian sub-image $G^{1'}_j$ of the enhanced image corresponding to the sample image $G^1$ ($0<=j<=n$), the Laplacian sub-image $L^{1'}_j$ ($0<=j<=(n-1)$). As another example, a sample pair may include the Laplacian sub-image $L^1_j$ of the sample image $G^1$ ($0<=j<=(n-1)$), the Laplacian sub-image $L^{1'}_j$ of the enhanced image corresponding to the sample image $G^1$ ($0<=j<=(n-1)$).

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

FIG. 27 is a flowchart illustrating an exemplary process for obtaining a training set according to some embodiments of the present disclosure.

In some embodiments, the process 2700 may be implemented in the imaging system 100 illustrated in FIG. 1. For example, the process 2700 may be stored in a storage medium (e.g., the storage device 150, or the storage 220 of the processing device 140) as a form of instructions, and can be invoked and/or executed by the processing device 140 (e.g., the processor 210 of the processing device 140, or one or more modules in the processing device 140 illustrated in FIG. 24). The operations of the illustrated process 2700 presented below are intended to be illustrative. In some embodiments, the process 2700 may be accomplished with one or more additional operations not described, and/or without one or more of the operations discussed. Additionally, the order in which the operations of the process 2700 as illustrated in FIG. 27 and described below is not intended to be limiting. In some embodiments, the process 2700 may be used to obtain the training set configured to training a preliminary model to obtain the machine learning model.

As shown in FIG. 27, the process 2700 for obtaining the training set may include:

Operation 2710: obtaining a sample image;

Operation 2720: obtaining a plurality of decomposition coefficients of the sample image by decomposing the sample image;

Operation 2730: obtaining a plurality of enhanced coefficients by performing enhancement to the decomposition coefficients of the sample image; and.

Operation 2740: determining the plurality of decomposition coefficients of the sample image and the plurality of corresponding enhanced coefficients as a sample pair.

Details regarding the sample image may be found elsewhere in the present disclosure (e.g., the description in connection with FIG. 26).

In some embodiments, a pre-processing operation may be performed on the sample image. Details regarding the pre-processing may be found elsewhere in the present disclosure (e.g., the description in connection with FIG. 26).

In some embodiments, the sample image may be decomposed using a multi-resolution analysis algorithm to obtain a plurality of decomposition coefficients of the sample image. The multi-resolution analysis algorithm may include a Gauss-Laplace pyramid decomposition algorithm, a wavelet decomposition algorithm, or the like.

In some embodiments, the Gauss-Laplace pyramid decomposition algorithm may be used to decompose the sample image. The Gauss-Lapras Gaussian pyramid decomposition algorithm has been described in detail in FIG. 28, and will not be described here.

In some embodiments, Gaussian decomposition may be performed on the sample image $G^3$ to obtain a Gaussian pyramid of the multi-layer Gaussian sub-image $G^3_j$ of the sample image $G^3$ and a Laplacian pyramid of the multi-layer Laplacian sub-image $L^3_j$.

In some embodiments, the number of decomposition layers n may be obtained according to the feature of the sample image, for example, the number of decomposition layers n may be set to 3.

In some embodiments, the Gaussian sub-image $G^3_j$ ($0<=j<=n$) and the Laplacian sub-image $L^3_j$ ($0<=j<=(n-1)$) may be the decomposition coefficients obtained after the sample image $G^3$ is decomposed by the Gauss-Laplacian pyramid algorithm.

In some embodiments, only the Laplacian sub-image $L^3_j$ ($0<=j<=(n-1)$) may be taken as the decomposition coefficient obtained after the sample image $G^3$ is subjected to the Gauss-Laplacian pyramid decomposition algorithm.

In some embodiments, the wavelet image decomposition algorithm may be used to decompose the sample image. The wavelet decomposition algorithm has been described in detail in FIG. 29, and will not be described here.

In some embodiments, the sample image $G^4$ may be subjected to wavelet decomposition processing to obtain sub-images $LL^4_{(k+1)}$, $HL^4_{(k+1)}$, $LH^4_{(k+1)}$, and $HH^4_{(k+1)}$. In some embodiments, the decomposition level m may be preset according to specific application conditions, for example, the decomposition level m may be set to 2.

In some embodiments, the sub-images $LL^4_k$, $HL^4_k$, $LH^4_k$, and $HH^4_k$ ($1<=k$) may be decomposition coefficients obtained after the sample image $G^4$ is subjected to the wavelet decomposition algorithm.

In some embodiments, the enhanced image may be deemed as an image obtained after any one of the image processing algorithms performed on the original image. The image processing algorithms may include, but are not limited to, denoising, scaling, binarization, grayscale, brightness adjustment, blurring, equalization, filtering, image segmentation, or the like. In some embodiments, the enhancement may be further understood as adding some information or transformed data to the original image by certain means, selectively highlighting the feature of interest in the image or suppressing (masking) some unwanted features in the image, so that the image and the visual response characteristic are matched. The sample image may be processed by performing a histogram equalization algorithm, a gamma conversion algorithm, an exponential image enhancement algorithm, a logarithmic image enhancement algorithm, or the like, or any combination thereof to obtain an enhanced image corresponding to the sample image. In some embodiments, a single threshold enhancement algorithm, a dual threshold enhancement algorithm, an adaptive enhancement algorithm, or the like, or any combination thereof may be performed on the decomposition coefficients to obtain enhancement coefficients. For example, the gray value of the decomposition coefficient may be normalized to obtain a normalized decomposition coefficient, and the normalized decomposition coefficient may be subjected to a power function transformation. The contrast equalization process may be performed to obtain the enhancement coefficient after the equalization process, which may be set according to the specific application situation. As another example, the power function may be a square function. In some embodiments, the wavelet decomposition may be performed on the decomposition coefficient to obtain the enhancement coefficient. The wavelet denoising processing may include wavelet transform modulus maximum value denoising algorithm, wavelet coefficient correlation denoising algorithm, wavelet transform threshold denoising algorithm, or the like. In some embodiments, the enhancement may be performed on one or more of the decomposition coefficients corresponding to the sample image to obtain one or more of the enhancement coefficients. For more enhancements, see the prior art: (1) Research on image enhancement processing algorithm based on wavelet transform, Xiang Cong, Tao Yongpeng, Computer and Digital Engineering, No. 8, 2017; (2) Digital Medicine Image Enhancement Based on Pyramid Method, Chen Xiaolong, Chen Gang, Wang Yi, No. 5, 2015; (3) Mammography based on binary wavelet and PDE image enhancement, Tang Quan, Huang Yunqi, Electronic Design Engineering, No. 5, 2018. The present disclosure does not impose any restriction on the type of enhancement processing, and any image obtained by the processing of the original image to change original image's rendering effect may be determined as the enhanced image.

In some embodiments, the training set may include decomposition coefficients and corresponding enhancement coefficients, or sample images and corresponding enhanced images.

In some embodiments, when the Gaussian sub-image $G^3_j$ ($0<=j<=n$) and the Laplacian sub-image $L^3_j$ ($0<=j<=(n-1)$) may be the decomposition coefficients of the sample image $G^3$. The Laplacian sub-image $L^3_j$ may be subjected to enhancement processing to obtain enhancement coefficients $L^3_j{}'$ ($0<=j<=(n-1)$) and $G^3_j{}'$ ($0<=j<=n$). The training set may include the Gaussian sub-image $G^3_j$ ($0<=j<=n$), the Laplacian sub-image $L^3_j$ ($0<=j<=(n-1)$), the enhancement coefficient $L^3_j{}'$ ($0<=j<=(n-1)$) and $G^3_j{}'$ ($0<=j<=n$).

In some embodiments, when the Laplacian sub-image $L^3_j$ ($0<=j<=(n-1)$) may be the decomposition coefficient of the sample image $G^3$. The Laplacian sub-image $L^3_j$ may be subjected to enhancement processing to obtain an enhancement coefficient $L^3_j{}'$ ($0<=j<=(n-1)$). The training set may include the Laplacian sub-image $L^3_j$ ($0<=j<=(n-1)$) and the enhancement coefficient $L^3_j{}'$ ($0<=j<=(n-1)$).

In some embodiments, when the sub-images $LL^4_k$, $HL^4_k$, $LH^4_k$, and $HH^4_k$ ($1<=k$) may be the decomposition coefficients of the sample image $G^4$. The enhancement processing may be performed on one or more of the sub-pictures $LL^4_k$, $HL^4_k$, $LH^4_k$, and $HH^4_k$ to obtain corresponding enhancement coefficients $LL^4_k$, $HL^4_k$, $LH^4_k$, and $HH^4_k$. The training set may include enhancement coefficients $LL^4_k$, $HL^4_k$, $LH^4_k$, and $HH^4_k$ corresponding to the sub-images $LL^4_k$, $HL^4_k$, $LH^4_k$, and $HH^4_k$ ($1<=k$).

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

A coefficient enhancement model may be obtained by performing machine learning on the sample images and the enhanced images processed by image enhancement. It is possible to perform an independent adaptive enhancement process for each image through the coefficient enhancement model, which reduces the difficulty of adjusting the enhancement effect and improves the image quality. It should be noted that different embodiments may have different beneficial effects. In different embodiments, the beneficial effects that may be produced may be any combination of one or more of the above, and may be any other beneficial effects that may be obtained.

During the image acquiring operation on the compressed breast tissue, there may be a collimator region in the acquired breast image, and since the collimator is a substance with high X-ray attenuation, there will be a high attenuation region in the corresponding location of the breast image. The high attenuation region increases the complexity and difficulty for processing the breast image, thereby reducing the processing effect of the breast image. Conventionally, the high attenuation region corresponding to the collimator in the breast image is removed by cropping the acquired breast image according to the mechanical feedback coordinates of the collimator. However, due to defects such as mechanical position errors, the collimator region remains in the cropped breast image.

In order to solve the traditional deficiencies based on mechanical feedback coordinates, yet another aspect of the present disclosure may provide systems and/or methods for determining a collimator region in a breast image.

Figure 30:
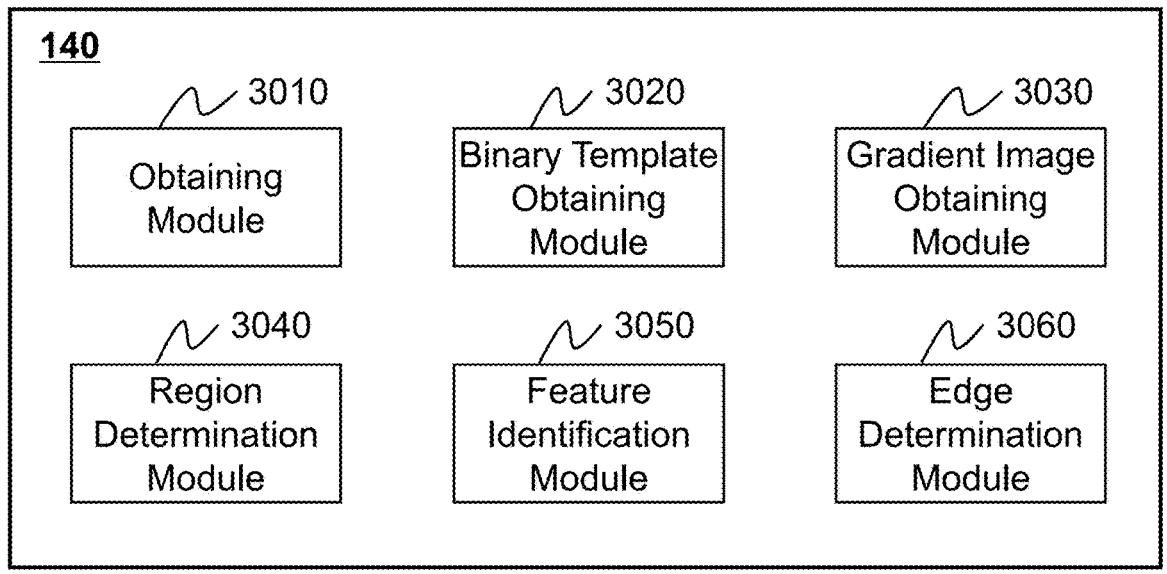
FIG. 30 is a schematic block diagram illustrating an exemplary processing device according to some embodiments of the present disclosure.

FIG. 30 is a schematic block diagram illustrating an exemplary processing device according to some embodiments of the present disclosure. The processing device 140 may include an obtaining module 3010, a binary template obtaining module 3020, a gradient image obtaining module 3030, a region determination module 3040, a feature identification module 3050, and an edge determination module 3060.

The obtaining module 3010 may be configured to obtain a breast image of an object that is acquired by an imaging device. The binary template obtaining module 3020 may be configured to obtain a binary template including a direct exposure region of the breast image. The gradient image obtaining module 3030 may be configured to obtain a binary gradient image by performing gradient transform and binarization to the breast image, the binary gradient image including one or more straight line features. The region determination module 3040 may be configured to determine a preliminary region based on the binary template and the binary gradient image. The edge determination module 3060 may be configured to process at least one of the breast image, the binary template, and the binary gradient image to reduce an effect of overexposure or tissue of the object with high X-ray attenuation in the breast image on the one or more straight line features. The feature identification module 3050 may be configured to identify the one or more straight line features in the binary gradient image based on the processing result. The edge determination module 3060 may be further configured to determine an edge of a collimator of the imaging device in the preliminary region based on the identified one or more straight line features, the edge including at least one of the identified one or more straight line features each of which has a length longer than a length threshold and is out of the direct exposure region.

The modules in the processing device 140 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. Two or more of the modules may be combined as a single module, and any one of the modules may be divided into two or more units.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 140 may further include a storage module (not shown in FIG. 30). The storage module may be configured to store data generated during any process performed by any component of in the processing device 140. As another example, each of the components of the processing device 140 may include a storage device. Additionally or alternatively, the components of the processing device 140 may share a common storage device.

Figure 31A:
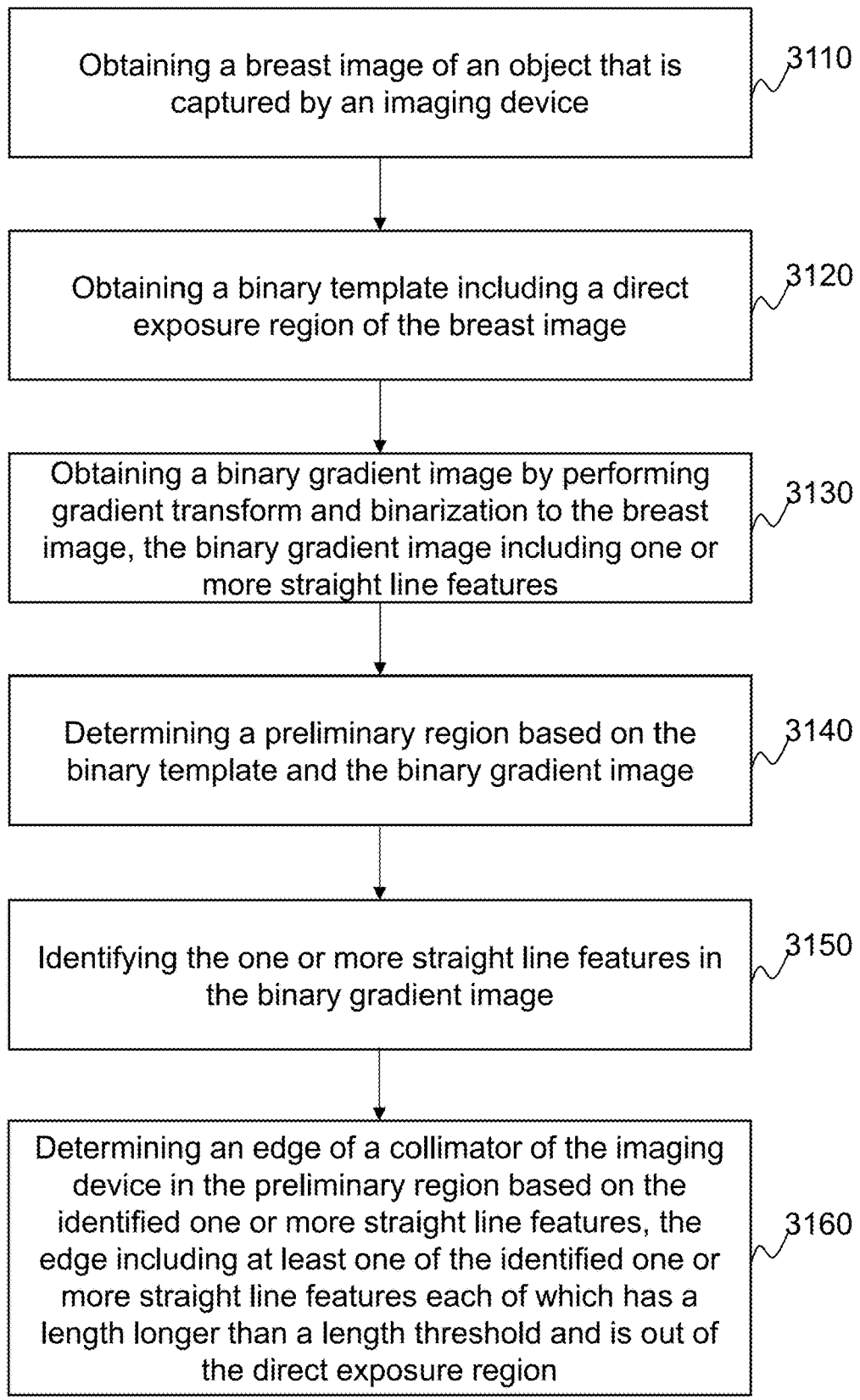
FIG. 31A is a flowchart illustrating an exemplary process for determining an edge of a collimator of an imaging device in a breast image according to some embodiments of the present disclosure.

FIG. 31A is a flowchart illustrating an exemplary process for determining an edge of a collimator of an imaging device in a breast image according to some embodiments of the present disclosure.

In some embodiments, the process 3100 may be implemented in the imaging system 100 illustrated in FIG. 1. For example, the process 3100 may be stored in a storage medium (e.g., the storage device 150, or the storage 220 of the processing device 140) as a form of instructions, and can be invoked and/or executed by the processing device 140 (e.g., the processor 210 of the processing device 140, or one or more modules in the processing device 140 illustrated in FIG. 30). The operations of the illustrated process 3100 presented below are intended to be illustrative. In some embodiments, the process 3100 may be accomplished with one or more additional operations not described, and/or without one or more of the operations discussed. Additionally, the order in which the operations of the process 3100 as illustrated in FIG. 31A and described below is not intended to be limiting.

In 3110, the processing device 140 (e.g., the obtaining module 3010) may obtain a breast image of an object that is acquired by an imaging device (e.g., the imaging device 110). In some embodiments, the imaging device 110 used here may be an X-ray device.

For example, the breast may be compressed by the compression pad of the imaging device 110. The compression pad may be a large compression pad, a small compression pad, a point compression pad, an axilla compression pad, or the like. The opening of the collimator of the imaging system 100 may be adjusted to match the type of the compression pad. Then the compressed breast may be scanned by the imaging device 110 to obtain the breast image.

In some embodiments, the processing device 140 may pre-process the breast image. For example, the processing device 140 may perform at least one of normalization, gray linearization, bilinear interpolation, and median filtering to the breast image. The subsequent operations (e.g., operations 3120-3160) may be performed based on the pre-processed breast image.

Taking normalization as an example, the breast image may be normalized such that the pixel values in the normalized breast image (e.g., the image in FIG. 33A) may be within a range of 0-1.

The normalization process may include: first obtaining a maximum pixel value $P_{max}$ and a minimum pixel value $P_{min}$ in the breast image; determining a first result by subtracting the minimum pixel value $P_{min}$ from the maximum pixel value $P_{max}$; determining a second result by subtracting the minimum pixel value $P_{min}$ from the pixel value $P_n$ (n is a positive integer) of a pixel; and determining a third result by dividing the second result by the first result. The third result may be the normalized pixel value $P_n'$ of the pixel, $P_n'=(P_n-P_{min})/(P_{max}-P_{min})$. In this way, each pixel value in the normalized breast image may be within the range of 0-1.

In some embodiments, the processing device 140 may perform gray linearization and median filtering to the breast image to improve the accuracy of the collimator region detection. For example, as shown in FIG. 31B, the breast image 11 may include a bad line 12 that may affect the detection of the straight line features. The processing device 140 may perform gray linearization and median filtering to the breast image 11 to remove the bad line 12 from the breast image 11, thereby obtaining the pre-processed breast image 13 in FIG. 31C without the bad line.

For example, the processing device 140 may subtract the global offset of the detector of the imaging device 110 from the gray values of the breast image 11 and set the results that are less than 0 as 0, thereby realizing the gray linearization performed on the breast image 11.

In some embodiments, the processing device 140 may shrink the breast image by a first shrinking scale (e.g., 10%) by performing bilinear interpolation to the breast image. Since the subsequent operations (e.g., operations 3120-3160) may be performed based on the shrunk breast image that is smaller than the original breast image, the required processing resource may be reduced and the processing speed may be improved. The edge of the collimator determined based on the shrunk breast image may be magnified by the first shrinking scale to obtain the actual edge of the collimator.

In some embodiments, if the processing device 140 shrinks the breast image by the first shrinking scale, the processing device 140 may also shrink the binary template by the first shrinking scale using, for example, nearest neighbor interpolation.

In 3120, the processing device 140 (e.g., the binary template obtaining module 3020) may obtain a binary template including a direct exposure region of the breast image.

In some embodiments, the direct exposure region may indicate that from the X-ray tube to a part of the detector corresponding to the direct exposure region, the X-rays do not go through the substance that attenuates the X-rays. For example, from the X-ray tube to the part of the detector corresponding to the direct exposure region, the X-rays may go through the compression pad and the breast-holder tray, without going through the object and the collimator. As a result, the direct exposure region may be brighter than one or more other regions in the breast image (e.g., a gray scale image). The processing device 140 may identify the direct exposure region based on pixel values (e.g., gray values) of pixels of the breast image. For example, the processing device 140 may determine that pixels with pixel values larger than a pixel threshold belong to the direct exposure region. The processing device 140 may obtain the binary template by designating the pixel values of pixels in the direct exposure region as 1 and designating the pixel values of pixels in the other region as 0.

Figure 36A:
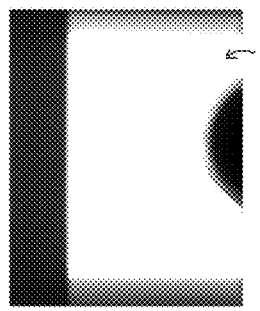
FIG. 36A is a schematic diagram of an exemplary breast image including overexposure according to some embodiments of the present disclosure.

If there is overexposure in the breast image, the overexposure may cause the direct exposure region to be too large, and even to cover the collimator region (e.g., the region 31 in FIG. 36A), which may cause the straight line features corresponding to the edge of the collimator detected based on line detection to be discarded.

In this case, the processing device 140 may perform erosion to the direct exposure region in the binary template using a first erosion kernel or a second erosion kernel. A size of the second erosion kernel may be larger than that of the first erosion kernel.

Figure 36B:
FIG. 36B is a schematic diagram of an exemplary binary template according to some embodiments of the present disclosure.
Figure 36C:
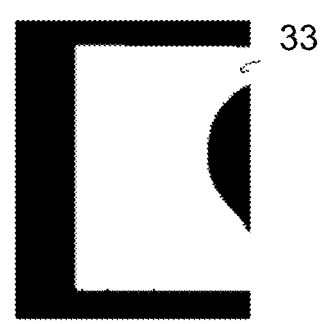
FIG. 36C is a schematic diagram of an exemplary high gray template according to some embodiments of the present disclosure.

The processing device 140 may obtain a high-gray template (e.g., the image in FIG. 36C) based on the breast image and a first gray threshold (e.g., 40000-60000). The high-gray template may include a first gray region (e.g., the region 33 in FIG. 36C) in which gray values of pixels are greater than or equal to the first gray threshold. The processing device 140 may determine whether a ratio of a size of the first gray region in the high-gray template to a size of the direct exposure region in the binary template (e.g., the region 32 in FIG. 36B) is greater than a ratio threshold. The processing device 140 may perform the erosion to the direct exposure region in the binary template based on a determination result.

In some embodiments, the determination result may include that the ratio of the size of the first gray region to the size of the direct exposure region is greater than the ratio threshold (e.g., 90%), which indicates that there is overexposure in the breast image. The processing device 140 may perform the erosion to the direct exposure region in the binary template using the second erosion kernel.

In some embodiments, the determination result may include that the ratio of the size of the first gray region to the size of the direct exposure region is less than the ratio threshold, which indicates that there is no overexposure in the breast image. The processing device 140 may perform the erosion to the direct exposure region in the binary template using the first erosion kernel or perform no erosion to the direct exposure region.

Among them, the "kernel" in the first erosion kernel and the second erosion kernel may be of any shape and size, and the kernel may have an anchor point. For example, the kernel K1 in the second erosion kernel may be a matrix of 5*5 and the kernel K2 in the first erosion kernel may be a matrix of 3*3.

In 3130, the processing device 140 (e.g., the gradient image obtaining module 3030) may obtain a binary gradient image by performing gradient transform and binarization to the breast image. The binary gradient image may include one or more straight line features.

In some embodiments, operation 3130 may be performed before, after, or simultaneously with operation 3120.

In some embodiments, since the collimator may not be applied on the side close to the patient's body during a breast scan, there may be no collimator on the side of the breast image close to the chest wall. The breast image may be a rectangle and have four sides. One of the four sides that is close to the chest wall in the breast image may be the chest-wall side. As a result, the breast image may include a chest-wall side (e.g., the right side of images shown in the figures of the present disclosure), a side opposite to the chest-wall side (e.g., the left side of images shown in the figures of the present disclosure), an upper side, and a lower side. It is necessary to identify the straight line features related to the upper side, the lower side, and the left side of the breast image.

In some embodiments, the binary gradient image may include a first sub-image, a second sub-image, a third sub-image, and a fourth sub-image.

In some embodiments, the processing device 140 may process the breast image by performing gradient transform and binarization to the breast image. The processing device 140 may obtain the first sub-image based on a first gradient threshold and the processing result. The first sub-image may represent a contour feature of the breast image. The processing device 140 may obtain the second sub-image associated with the upper side, the third sub-image associated with the lower side, and the third sub-image associated with the left side based on a second gradient threshold and the processing result. The first gradient threshold may be greater than the second gradient threshold.

FIG. 32A is a schematic diagram showing an exemplary edge of a collimator according to some embodiments of the present disclosure. FIG. 32B is a schematic diagram of an exemplary gray value feature curve related to the edge of the collimator in FIG. 32A according to some embodiments of the present disclosure. Here, for each point on the curve in FIG. 32B, a first coordinate on a first coordinate axis (e.g., the vertical coordinate axis in FIG. 32B) of the point represents a gray value of a pixel in the image in FIG. 32A, and a second coordinate on a second coordinate axis (e.g., the horizontal coordinate axis in FIG. 32B) of the point represents the distance from the pixel to the left side of the image in FIG. 32A. Referring to FIGS. 32A and 32B, in any straight line (e.g., line 3210) parallel to the upper side of the image in FIG. 32A, a relationship of the distance D between a pixel and the left side and the gray value G of the pixel may be shown in FIG. 32B. Referring to the shape of the curve L in FIG. 32B, the gray values G of pixels nearby the edge (e.g., edge 3220) of the collimator change in a sloping trend, of which the first derivative can be regarded as a constant. Therefore, a stepwise operator, for example, a Sobel operator or a Hough transform, may be used to obtain straight line features and detect the edge of the collimator.

In some embodiments, the Sobel operator may include a horizontal operator and a vertical operator. The processing device 140 may extract one or more straight line features in the horizontal and vertical directions based on the operator matrix, the horizontal direction Equation (1), the vertical direction Equation (2), and Equation (3) related to the whole gradient of the breast image below:

$$g_x = \partial f / \partial x = (z_7 + 2z_8 + z_9) - (z_1 + 2z_2 + z_3), \quad (1)$$

$$g_y = \partial f / \partial y = (z_3 + 2z_6 + z_9) - (z_1 + 2z_4 + z_7), \quad (2)$$

and $$M(x,y) \approx |g_x| + |g_y|, \quad (3)$$

Operator matrix diagram

| $z_1$ | $z_2$ | $z_3$ |
|---|---|---|
| $z_4$ | $z_5$ | $z_6$ |
| $z_7$ | $z_8$ | $z_9$ |

Operator matrix in the horizontal direction

| −1 | −2 | −1 |
|---|---|---|
| 0 | 0 | 0 |
| 1 | 2 | 1 |

Operator matrix in the vertical direction

| −1 | 0 | 1 |
|---|---|---|
| −2 | 0 | 2 |
| −1 | 0 | 1 |

In the horizontal straight line features extracted by Equation (1), the gradient value related to the upper edge of the collimator region may be a positive value, and the gradient value related to the lower edge of the collimator region may be a negative value. In the vertical straight line features extracted by Equation (2), the gradient value related to the left edge of the collimator region may be a positive value. The edge of the collimator region may be determined more accurately by extract the straight line features using the Sobel operator, which may reduce the complexity and difficulty of image processing, and improve the accuracy of the detection and positioning of the collimator region.

Figure 33A:
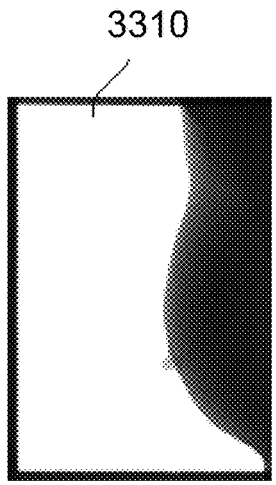
FIG. 33A is a schematic diagram of an exemplary pre-processed breast image according to some embodiments of the present disclosure.
Figure 33B:
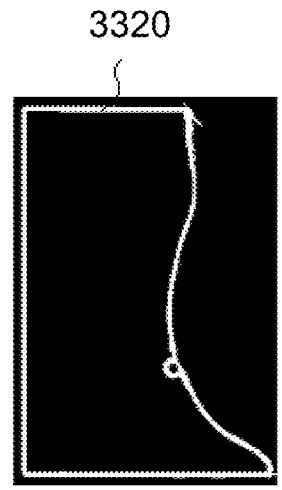
FIGS. 33B-33E are schematic diagrams of exemplary first sub-image, second sub-image, third sub-image, fourth sub-image, respectively, according to some embodiments of the present disclosure.
Figure 33C:
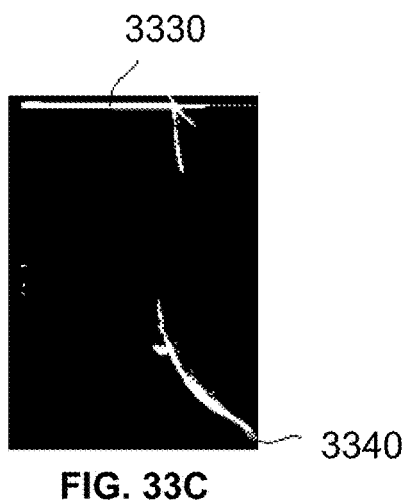
Figure 33D:
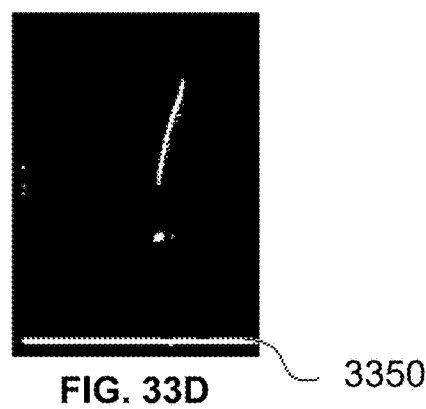
Figure 33E:
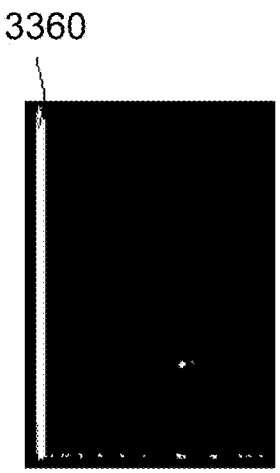

For example, the processing device 140 may obtain a binary gradient image in FIG. 33B (the first sub-image) by processing the breast image 3310 in FIG. 33A by performing gradient transform using Equation (3) based on a first gradient threshold (T1) and binarization to the breast image. The first sub-image may include the edge 3320 (e.g., the whole Sobel straight line features) of the collimator region. The processing device 140 may obtain a binary gradient image in FIG. 33C (the second sub-image) by processing the breast image in FIG. 33A by performing gradient transform using Equation (1) based on a second gradient threshold (T2) and binarization to the breast image. The second sub-image may include the straight line features related to the upper edge 3330 of the collimator region. The processing device 140 may obtain a binary gradient image in FIG. 33D (the third sub-image) by processing the breast image in FIG. 33A by performing gradient transform using Equation (1) based on the second gradient threshold (T2) and binarization to the breast image. The third sub-image may include the straight line features related to the lower edge 3350 of the collimator region. The processing device 140 may obtain a binary gradient image in FIG. 33E (the fourth sub-image) by processing the breast image in FIG. 33A by performing gradient transform using Equation (2) based on the second gradient threshold (T2) and binarization to the breast image. The fourth sub-image may include the straight line features related to the left edge 3360 of the collimator region. The first gradient threshold may be larger than the second gradient threshold (T1>T2). In some embodiments, there may be interfering features (e.g., 3340 and/or white points in FIG. 33C) in the binary gradient image.

In 3140, the processing device 140 (e.g., the region determination module 3040) may determine a preliminary region based on the binary template and the binary gradient image. In some embodiments, the preliminary region may include and be larger than the direct exposure region.

In some embodiments, the processing device 140 may determine the preliminary region in the breast image based on the binary template and the first sub-image.

In some embodiments, the processing device 140 may determine a fourth region corresponding to the direct exposure region in the binary template based on a first edge feature of the binary template. The processing device 140 may determine a fifth region corresponding to the direct exposure region in the binary gradient image (e.g., the first sub-image) based on a second edge feature of the binary gradient image. The processing device 140 may determine a union set of the fourth region and the fifth region as the preliminary region.

Figure 34A:
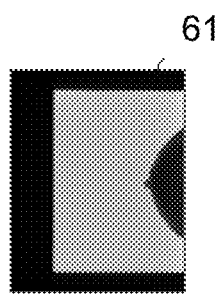
FIG. 34A is a schematic diagram of an exemplary pre-processed breast image according to some embodiments of the present disclosure.
Figure 34B:
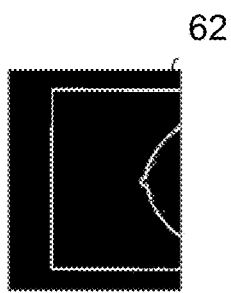
FIG. 34B is a schematic diagram of an exemplary first sub-image according to some embodiments of the present disclosure.
Figure 34C:
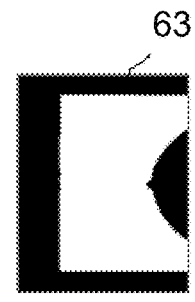
FIG. 34C is a schematic diagram of an exemplary binary template according to some embodiments of the present disclosure.
Figure 34D:
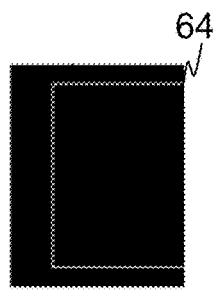
FIG. 34D is a schematic diagram of an exemplary preliminary region according to some embodiments of the present disclosure.

For example, the image 61 in FIG. 34A is a pre-processed breast image. The image in FIG. 34B may be the first sub-image obtained based on the image 61. The image in FIG. 34B may include the region 62 corresponding to the direct exposure region. The image in FIG. 34C may be the binary template obtained based on the image 61. The image in FIG. 34C may include the region 63 corresponding to the direct exposure region. The processing device 140 may determine the union set of the region 62 and the region 63 as the preliminary region 64 shown in FIG. 33D.

Figure 35A:
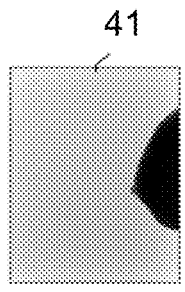
FIG. 35A is a schematic diagram of an exemplary pre-processed breast image according to some embodiments of the present disclosure.

In some embodiments, the processing device 140 may obtain a physical position of the collimator in the imaging device 110. The processing device 140 may project the collimator on the original breast image based on the physical position of the collimator. The processing device 140 may obtain the cropped breast image (e.g., the image 41 shown in FIG. 35A) by cropping the original breast image along the projection of the collimator.

Figure 35B:
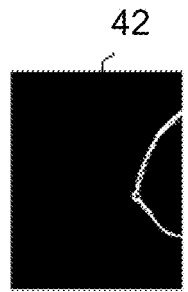
FIG. 35B is a schematic diagram of an exemplary first sub-image according to some embodiments of the present disclosure.
Figure 35C:
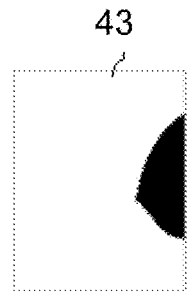
FIG. 35C is a schematic diagram of an exemplary binary template according to some embodiments of the present disclosure.
Figure 35D:
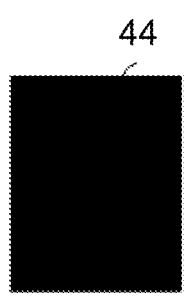
FIG. 35D is a schematic diagram of an exemplary preliminary region according to some embodiments of the present disclosure.

The image in FIG. 35B may be the first sub-image obtained based on the image 41. The image in FIG. 35B may include the region 42 corresponding to the direct exposure region. The image in FIG. 35C may be the binary template obtained based on the image 41. The image in FIG. 35C may include the region 43 corresponding to the direct exposure region. The processing device 140 may determine the union set of the region 42 and the region 43 as the preliminary region 44 shown in FIG. 35D.

In 3150, the processing device 140 (e.g., the feature identification module 3050) may identify the one or more straight line features in the binary gradient image. In some embodiments, the processing device 140 may identify the one or more straight line features in the binary gradient image using Hough transform. In some embodiments, the processing device 140 may identify the one or more straight line features in the binary gradient image by determining one or more row projection values and one or more column projection values. Each of the one or more row projection values may be a sum of pixel values of a row of pixels in the binary gradient image. Each of the one or more column projection values may be a sum of pixel values of a column of pixels in the binary gradient image. A row of pixels may be arranged along a direction perpendicular to the extension direction of the chest-wall side. A column of pixels may be arranged along the extension direction of the chest-wall side.

In 3160, the processing device 140 (e.g., the edge determination module 3060) may determine an edge of a collimator of the imaging device in the preliminary region based on the identified one or more straight line features. The edge may include at least one of the identified one or more straight line features each of which has a length longer than a length threshold and is out of the direct exposure region.

In some embodiments, the determined edge of the collimator in the breast image may include the identified straight line features including a row of pixels associated with the upper side, a row of pixels associated with the lower side, and a column of pixels associated with the left side. The row projection value of the row of pixels associated with the upper side may be a first projection value, the row projection value of the row of pixels associated with the lower side may be a second projection value, and the column projection value of the column of pixels associated with the side opposite to the chest-wall side may be a third projection value. The length threshold may include a first length threshold, a second length threshold, and a third length threshold. The first projection value may be greater than the first length threshold, the second projection value may be greater than the second length threshold, and the third projection value may be greater than the third length threshold.

In some embodiments, a ratio of the first length threshold to a length of an upper side or a lower side of the preliminary region may be equal to a first preset value (e.g., 90%, 80%, 70%, 60%, etc.), a ratio of the third length threshold to a length of an edge opposite to the chest-wall side of the preliminary region may be equal to a second preset value (e.g., 90%, 80%, 70%, 60%, etc.), and the first length threshold may be equal to the second length threshold. Further, the first preset value and/or the second preset value may be larger than 80%.

In some embodiments, the processing device 140 may determine the first projection value in the second sub-image. The first projection value may be a maximum row projection value in the second sub-image. The processing device 140 may determine the second projection value in the third sub-image. The second projection value may be a maximum row projection value in the third sub-image. The processing device 140 may determine the third projection value in the fourth sub-image. The third projection value may be a maximum column projection value in the fourth sub-image.

In some embodiments, the processing device 140 may determine a center point of the preliminary region. For the straight line feature with the first projection value related to the upper side, the processing device 140 may determine whether there is at least a portion of the direct exposure region in the side of the straight line feature away from the center point. In response to a determination that there is no direct exposure region in the side of the straight line feature away from the center point, the processing device 140 may determine the straight line feature as the upper edge of the collimator in the breast image. For the straight line feature with the second projection value related to the lower side, the processing device 140 may determine whether there is at least a portion of the direct exposure region in the side of the straight line feature away from the center point. In response to a determination that there is no direct exposure region in the side of the straight line feature away from the center point, the processing device 140 may determine the straight line feature as the lower edge of the collimator in the breast image. For the straight line feature with the third projection value related to the left side, the processing device 140 may determine whether there is at least a portion of the direct exposure region in the side of the straight line feature away from the center point. In response to a determination that there is no direct exposure region in the side of the straight line feature away from the center point, the processing device 140 may determine the straight line feature as the left edge of the collimator in the breast image.

In some embodiments, the processing device 140 may add a make-up part to at least one of the one or more straight line features in the preliminary region. The make-up part may be in a region (e.g., a low gray region) corresponding to tissue of the object with high X-ray attenuation.

Figure 37A:
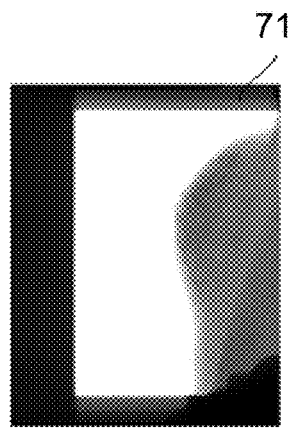
FIG. 37A is a schematic diagram of an exemplary breast image including a low gray region according to some embodiments of the present disclosure.
Figure 37B:
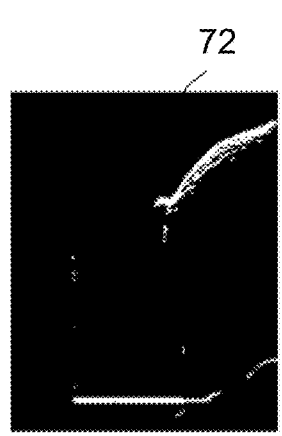
FIG. 37B is a schematic diagram of an exemplary third sub-image according to some embodiments of the present disclosure.
Figure 37C:
FIGS. 37C-37E are schematic diagrams of exemplary low gray templates according to some embodiments of the present disclosure.
Figure 37D:
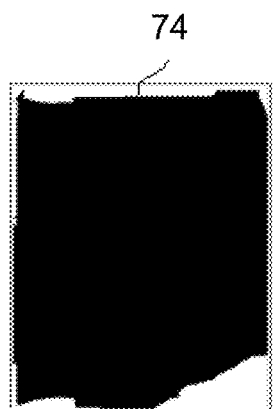
Figure 37E:
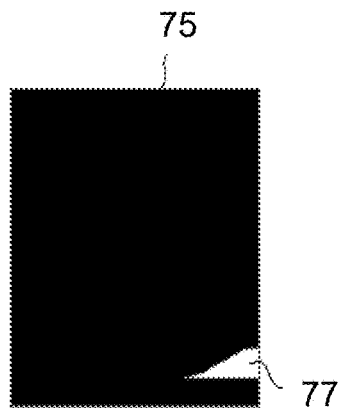
Figure 37F:
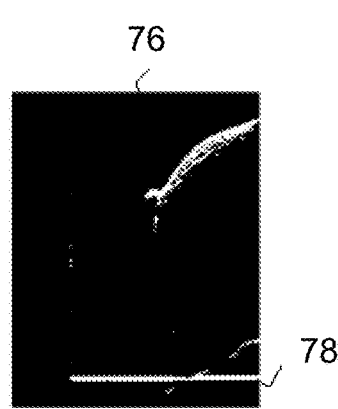

The processing device 140 may obtain a first low-gray template (e.g., the image 73 in FIG. 37C) based on the breast image (e.g., the image 71 in FIG. 37A) and a second gray threshold (e.g., 50-100). The first low-gray template may include a first region representing the tissue of the object with high X-ray attenuation. The processing device 140 may determine a second region by performing dilation to the first region using a dilation kernel to generate a second low-gray template (e.g., the image 74 in FIG. 37D). The second region may be larger than the first region. The processing device 140 may obtain a third low-gray template (e.g., the image 75 in FIG. 37E) by removing a region other than the preliminary region from the second low-gray template. The third low-gray template may include a third region (e.g., the region 77 in FIG. 37E) corresponding to the second region. The third region may be smaller than the second region. The processing device 140 may add the make-up part (e.g., the line 78 in FIG. 37F) to the at least one of the one or more straight line features (e.g., the straight line feature in the third sub-image 72 in FIG. 37B) in the preliminary region in the image 76 by extending the at least one of the one or more straight line features to the third region.

After the make-up operation, the processing device 140 may determine the edge of the collimator based on the straight line features.

In some embodiments, the processing device 140 may obtain a physical position of the collimator in the imaging device. The processing device 140 may project at least a part of the collimator on the breast image based on the physical position of the collimator. The processing device 140 may determine the edge of the collimator in the breast image based on the projection and the identified straight line features.

In some embodiments, the processing device 140 may crop the breast image along the determined edge of the collimator.

Figure 38:
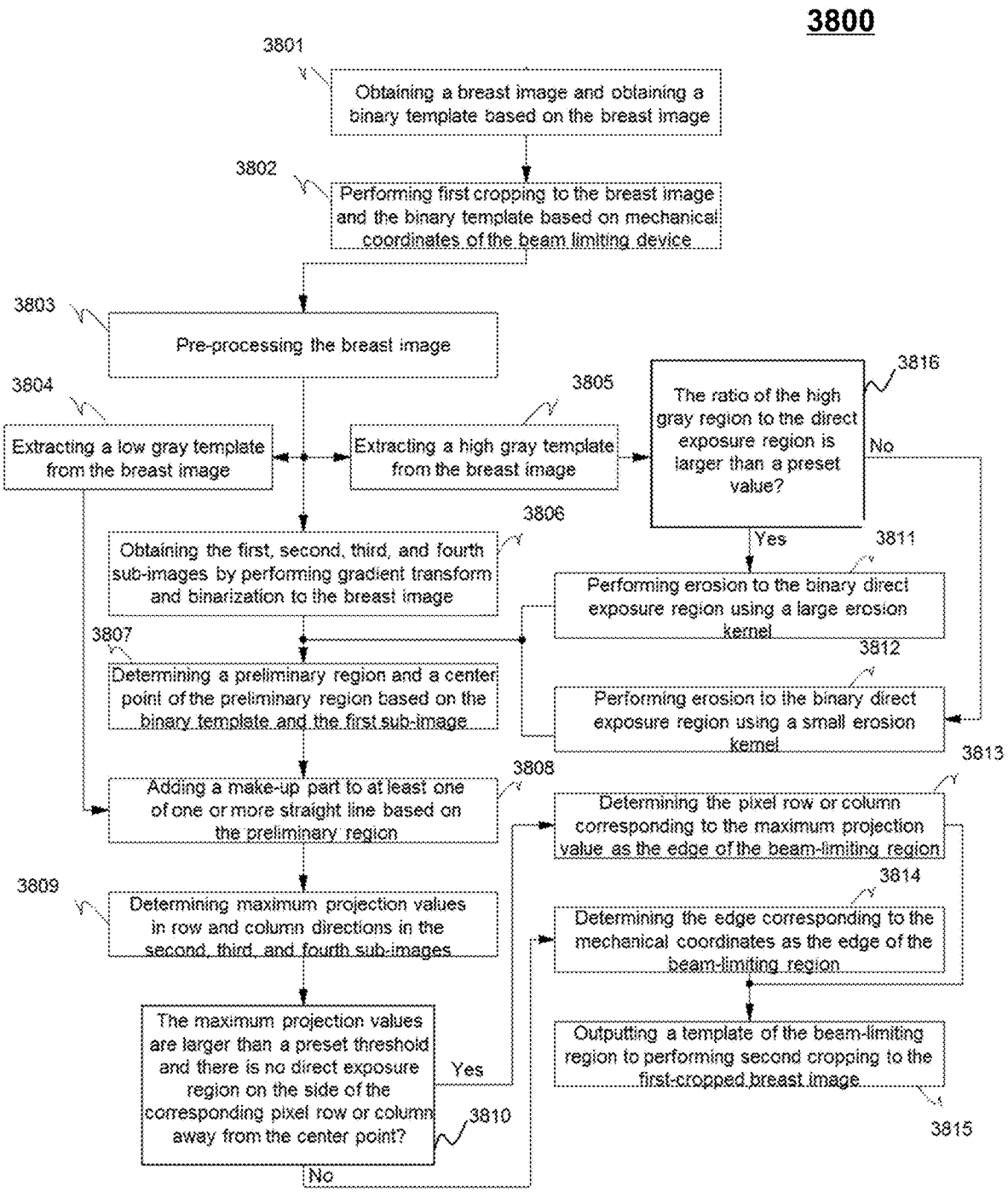
FIG. 38 is a flowchart illustrating an exemplary process for determining an edge of a collimator of an imaging device in a breast image according to some embodiments of the present disclosure.

FIG. 38 is a flowchart illustrating an exemplary process for determining an edge of a collimator of an imaging device in a breast image according to some embodiments of the present disclosure.

In some embodiments, the process 3800 may be implemented in the imaging system 100 illustrated in FIG. 1. For example, the process 3800 may be stored in a storage medium (e.g., the storage device 150, or the storage 220 of the processing device 140) as a form of instructions, and can be invoked and/or executed by the processing device 140 (e.g., the processor 210 of the processing device 140, or one or more modules in the processing device 140 illustrated in FIG. 30). The operations of the illustrated process 3800 presented below are intended to be illustrative. In some embodiments, the process 3800 may be accomplished with one or more additional operations not described, and/or without one or more of the operations discussed. Additionally, the order in which the operations of the process 3800 as illustrated in FIG. 38 and described below is not intended to be limiting.

In 3801, the processing device 140 may obtain a breast image and obtaining a binary template based on the breast image.

In 3802, the processing device 140 may perform first cropping to the breast image and the binary template based on mechanical coordinates of the collimator.

In 3803, the processing device 140 may pre-process the breast image.

In 3804, the processing device 140 may extract a low gray template from the breast image.

In 3805, the processing device 140 may extract a high gray template from the breast image.

In 3806, the processing device 140 may obtain the first, second, third, and fourth sub-images by performing gradient transform and binarization to the breast image.

In 3807, the processing device 140 may determine a preliminary region and a center point of the preliminary region based on the binary template and the first sub-image.

In 3808, the processing device 140 may add a make-up part to at least one of one or more straight line based on the preliminary region.

In 3809, the processing device 140 may determine maximum projection values in row and column directions in the second, third, and fourth sub-images.

In 3810, the processing device 140 may determine whether the maximum projection values are larger than a preset threshold and whether there is no direct exposure region on the side of the corresponding pixel row or column away from the center point. If yes, the processing device 140 may determine the pixel row or column corresponding to the maximum projection value as the edge of the collimator region. If no, the processing device 140 may determine the edge corresponding to the mechanical coordinates as the edge of the collimator region.

In 3816, the processing device 140 may determine whether the ratio of the high gray region to the direct exposure region is larger than a preset value. If yes, the processing device 140 may perform erosion to the binary direct exposure region using a large erosion kernel. If no, the processing device 140 may perform erosion to the binary direct exposure region using a small erosion kernel.

In 3815, the processing device 140 may output a template of the collimator region to performing second cropping to the first-cropped breast image.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

We claim:

1. A system for determining a breast region in a breast image comprising:
　at least one storage device including a set of instructions; and
　at least one processor in communication with the at least one storage device, wherein when executing the set of instructions, the at least one processor is directed to perform operations including:
　　obtaining the breast image of an object that is acquired by an imaging device;
　　dividing the breast image into a body region and a background region, the body region including a breast;
　　generating a binary image by designating pixel values of pixels in the body region as 1 and designating pixel values of pixels in the background region as 0;
　　determining a chest-wall side of the binary image; and
　　obtaining a projection curve by determining a plurality of sums each of which is a sum of pixel values of a row of pixels in the binary image, the row of pixels being arranged along a direction between the chest-wall side and a side of the binary image opposite to the chest-wall side;
　　determining a first valley point and a second valley point of the projection curve based on a shape of the projection curve;
　　determining a peak point of the projection curve between the first valley point and the second valley point of the projection curve;
　　determining a first valley location, a second valley location, and a peak location in the breast image based on the peak point, the first valley point, and the second valley point of the projection curve, wherein the first valley location, the second valley location, and the peak location in the breast image correspond to the first valley point, the second valley point, and the peak valley point in the curve projection, respectively; and
　　determining the breast region in the breast image by connecting the first valley location, the second valley location, and the peak location, wherein the determined breast region is configured to determine automatic exposure control (AEC) parameters for scanning a breast using the imaging device.

2. The system of claim 1, wherein for each point on the projection curve, a first coordinate on a first coordinate axis of the point represents a position of a row of pixels in the binary image, and a second coordinate on a second coordinate axis of the point represents a sum of pixel values of the corresponding row of pixels.

3. The system of claim 2, wherein the determining the first valley point and the second valley point of the projection curve includes:
　obtaining a preset distance between the first coordinates of the first valley point and the second valley point, and preset positions of the first valley point and the second valley point in the projection curve, the preset distance and the preset positions being set based on breast characteristics;
　determining whether there is any valley point or point whose second coordinate is 0 in the projection curve; and
　determining the first valley point and the second valley point in the projection curve based on the determination result, the preset distance, and the preset positions.

4. The system of claim 2, wherein the determining the first valley location, the second valley location, and the peak location in the breast image based on the peak point, the first valley point, and the second valley point of the projection curve includes:
　determining whether the second coordinate of the first valley point or the second valley point is greater than the second coordinate of the peak point;
　in response to determining that the second coordinate of the first valley point or the second valley point is greater than the second coordinate of the peak point, rotating the binary image so that a straight line connecting points in the rotated binary image corresponding to the first valley point and the second valley point is parallel to or coincides with the second coordinate axis;

determining a new projection curve based on the rotated binary image; and updating the first valley point, the second valley point, and the peak point based on the new projection curve; and determining the first valley location, the second valley location, and the peak location in the breast image based on the updated first valley point, the updated second valley point, and the updated peak point.

5. The system of claim 2, wherein the determining the first valley location, the second valley location, and the peak location in the breast image based on the peak point, the first valley point, and the second valley point of the projection curve includes:

determining whether there is no valley point in the projection curve and there is at least one point whose second coordinate is 0 on only one side of the peak point of the projection curve;

in response to determining that there is no valley point in the projection curve and there is at least one point whose second coordinate is 0 on only one side of the peak point of the projection curve, rotating the binary image so that a straight line connecting points in the rotated binary image corresponding to the first valley point and the second valley point is parallel to or coincides with the second coordinate axis;

determining a new projection curve based on the rotated binary image;

updating the first valley point, the second valley point, and the peak point based on the new projection curve; and determining the first valley location, the second valley location, and the peak location in the breast image based on the updated first valley point, the updated second valley point, and the updated peak point.

6. The system of claim 1, wherein the determining the breast region in the breast image by connecting the first valley location, the second valley location, and the peak location includes:

determining a first straight line from the peak location, the first straight line being perpendicular to a second straight line connecting the first valley location and the second valley location;

determining an intersection of the first straight line and a chest-wall side of the breast image; and determining the breast region in the breast image by connecting the first valley location, the second valley location, and intersection.

7. A method for determining a breast region in a breast image implemented on a machine having at least one storage device and at least one processor, comprising:

obtaining the breast image of an object that is acquired by an imaging device;

dividing the breast image into a body region and a background region, the body region including a breast;

generating a binary image by designating pixel values of pixels in the body region as 1 and designating pixel values of pixels in the background region as 0;

determining a chest-wall side of the binary image; and obtaining a projection curve by determining a plurality of sums each of which is a sum of pixel values of a row of pixels in the binary image, the row of pixels being arranged along a direction between the chest-wall side and a side of the binary image opposite to the chest-wall side;

determining a first valley point and a second valley point of the projection curve based on a shape of the projection curve;

determining a peak point of the projection curve between the first valley point and the second valley point of the projection curve;

determining a first valley location, a second valley location, and a peak location in the breast image based on the peak point, the first valley point, and the second valley point of the projection curve, wherein the first valley location, the second valley location, and the peak location in the breast image correspond to the first valley point, the second valley point, and the peak valley point in the curve projection, respectively; and determining the breast region in the breast image by connecting the first valley location, the second valley location, and the peak location, wherein the determined breast region is configured to determine automatic exposure control (AEC) parameters for scanning a breast using the imaging device.

8. The method of claim 7, wherein for each point on the projection curve, a first coordinate on a first coordinate axis of the point represents a position of a row of pixels in the binary image, and a second coordinate on a second coordinate axis of the point represents a sum of pixel values of the corresponding row of pixels.

9. The method of claim 8, wherein the determining the first valley point and the second valley point of the projection curve includes:

obtaining a preset distance between the first coordinates of the first valley point and the second valley point, and preset positions of the first valley point and the second valley point in the projection curve, the preset distance and the preset positions being set based on breast characteristics;

determining whether there is any valley point or point whose second coordinate is 0 in the projection curve; and determining the first valley point and the second valley point in the projection curve based on the determination result, the preset distance, and the preset positions.

10. The method of claim 8, wherein the determining first valley location, the second valley location, and the peak location in the breast image based on the peak point, the first valley point, and the second valley point of the projection curve includes:

determining whether the second coordinate of the first valley point or the second valley point is greater than the second coordinate of the peak point;

in response to determining that the second coordinate of the first valley point or the second valley point is greater than the second coordinate of the peak point, rotating the binary image so that a straight line connecting points in the rotated binary image corresponding to the first valley point and the second valley point is parallel to or coincides with the second coordinate axis;

determining a new projection curve based on the rotated binary image; and updating the first valley point, the second valley point, and the peak point based on the new projection curve; and determining the first valley location, the second valley location, and the peak location in the breast image based on the updated first valley point, the updated second valley point, and the updated peak point.

11. The method of claim 8, wherein the determining the first valley location, the second valley location, and the peak location in the breast image based on the peak point, the first valley point, and the second valley point of the projection curve includes:
   determining whether there is no valley point in the projection curve and there is at least one point whose second coordinate is 0 on only one side of the peak point of the projection curve;
   in response to determining that there is no valley point in the projection curve and there is at least one point whose second coordinate is 0 on only one side of the peak point of the projection curve, rotating the binary image so that a straight line connecting points in the rotated binary image corresponding to the first valley point and the second valley point is parallel to or coincides with the second coordinate axis;
   determining a new projection curve based on the rotated binary image;
   updating the first valley point, the second valley point, and the peak point based on the new projection curve; and
   determining the first valley location, the second valley location, and the peak location in the breast image based on the updated first valley point, the updated second valley point, and the updated peak point.

12. The method of claim 7, wherein the determining the breast region in the breast image by connecting the first valley location, the second valley location, and the peak location includes:
   determining a first straight line from the peak location, the first straight line being perpendicular to a second straight line connecting the first valley location and the second valley location;
   determining an intersection of the first straight line and a chest-wall side of the breast image; and
   determining the breast region in the breast image by connecting the first valley location, the second valley location, and intersection.

13. A method for obtaining automatic exposure control (AEC) parameters of an imaging device implemented on a machine having at least one storage device and at least one processor, comprising:
   obtaining a pre-exposure breast image of a breast of an object that is acquired by an imaging device;
   determining a breast region in the pre-exposure breast image by processing the pre-exposure breast image; and
   determining AEC parameters based on the breast region of the pre-exposure breast image, wherein the AEC parameters are configured to perform a formal scan using the imaging device to acquire a formal breast image of the breast,
   wherein the determining a breast region in the pre-exposure breast image by processing the pre-exposure breast image includes:
      dividing the pre-exposure breast image into a body region and a background region, the body region including a breast;
      generating a binary image by designating pixel values of pixels in the body region as 1 and designating pixel values of pixels in the background region as 0;
      determining a chest-wall side of the binary image;
      obtaining a projection curve by determining a plurality of sums each of which is a sum of pixel values of a row of pixels in the binary image, the row of pixels being arranged along a direction between the chest-wall side and a side of the binary image opposite to the chest-wall side;
      determining a first valley point and a second valley point of the projection curve based on a shape of the projection curve;
      determining a peak point of the projection curve between the first valley point and the second valley point of the projection curve;
      determining a first valley location, a second valley location, and a peak location in the pre-exposure breast image based on the peak point, the first valley point, and the second valley point of the projection curve, wherein the first valley location, the second valley location, and the peak location in the pre-exposure breast image correspond to the first valley point, the second valley point, and the peak valley point in the curve projection, respectively; and
      determining the breast region in the pre-exposure breast image by connecting the first valley location, the second valley location, and the peak location.

14. The method of claim 13, wherein the determining AEC parameters based on the breast region of the pre-exposure breast image includes:
   determining a gland region in the determined breast region;
   determining a gray level of the gland region;
   obtaining a pre-exposure X-ray dose and a compression thickness of the breast used to acquire the pre-exposure breast image;
   obtaining a preset relationship of the pre-exposure X-ray dose, the compression thickness of the breast, the gray level of the gland region, and the AEC parameters; and
   determining the AEC parameters based on the preset relationship, the pre-exposure X-ray dose, the compression thickness of the breast, and the gray level of the gland region.

15. The method of claim 13, wherein for each point on the projection curve, a first coordinate on a first coordinate axis of the point represents a position of a row of pixels in the binary image, and a second coordinate on a second coordinate axis of the point represents a sum of pixel values of the corresponding row of pixels.

16. The method of claim 15, wherein the determining the first valley point and the second valley point of the projection curve includes:
   obtaining a preset distance between the first coordinates of the first valley point and the second valley point, and preset positions of the first valley point and the second valley point in the projection curve, the preset distance and the preset positions being set based on breast characteristics;
   determining whether there is any valley point or point whose second coordinate is 0 in the projection curve; and
   determining the first valley point and the second valley point in the projection curve based on the determination result, the preset distance, and the preset positions.

17. The method of claim 15, wherein the determining the first valley location, the second valley location, and the peak location in the breast image based on the peak point, the first valley point, and the second valley point of the projection curve includes:
   determining whether the second coordinate of the first valley point or the second valley point is greater than the second coordinate of the peak point;

in response to determining that the second coordinate of the first valley point or the second valley point is greater than the second coordinate of the peak point, rotating the binary image so that a straight line connecting points in the rotated binary image corresponding to the first valley point and the second valley point is parallel to or coincides with the second coordinate axis;

determining a new projection curve based on the rotated binary image; and updating the first valley point, the second valley point, and the peak point based on the new projection curve; and determining the first valley location, the second valley location, and the peak location in the breast image based on the updated first valley point, the updated second valley point, and the updated peak point.

18. The method of claim 15, wherein the determining the first valley location, the second valley location, and the peak location in the breast image based on the peak point, the first valley point, and the second valley point of the projection curve includes:

determining whether there is no valley point in the projection curve and there is at least one point whose second coordinate is 0 on only one side of the peak point of the projection curve;

in response to determining that there is no valley point in the projection curve and there is at least one point whose second coordinate is 0 on only one side of the peak point of the projection curve, rotating the binary image so that a straight line connecting points in the rotated binary image corresponding to the first valley point and the second valley point is parallel to or coincides with the second coordinate axis;

determining a new projection curve based on the rotated binary image;

updating the first valley point, the second valley point, and the peak point based on the new projection curve; and determining the first valley location, the second valley location, and the peak location in the breast image based on the updated first valley point, the updated second valley point, and the updated peak point.

19. The method of claim 13, wherein the determining the breast region in the breast image by connecting the first valley location, the second valley location, and the peak location includes:

determining a first straight line from the peak location, the first straight line being perpendicular to a second straight line connecting the first valley location and the second valley location;

determining an intersection of the first straight line and a chest-wall side of the breast image; and determining the breast region in the breast image by connecting the first valley location, the second valley location, and intersection.

* * * * *